(12) United States Patent
Victor

(10) Patent No.: US 8,440,440 B2
(45) Date of Patent: May 14, 2013

(54) ULTRASONIC CAVITATION DERIVED STROMAL OR MESENCHYMAL VASCULAR EXTRACTS AND CELLS DERIVED THEREFROM OBTAINED FROM ADIPOSE TISSUE AND USE THEREOF

(75) Inventor: Steven Victor, New York, NY (US)

(73) Assignee: Intellicell Biosciences Inc., New York, NY (US)

( * ) Notice: Subject to any disclaimer, the term of this patent is extended or adjusted under 35 U.S.C. 154(b) by 0 days.

(21) Appl. No.: 13/323,030

(22) Filed: Dec. 12, 2011

(65) Prior Publication Data
US 2012/0164113 A1 Jun. 28, 2012

Related U.S. Application Data

(60) Provisional application No. 61/427,221, filed on Dec. 27, 2010.

(51) Int. Cl.
*C12N 13/00* (2006.01)
(52) U.S. Cl.
USPC ...................................................... 435/173.9
(58) Field of Classification Search .................. None
See application file for complete search history.

(56) References Cited

U.S. PATENT DOCUMENTS

| | | | |
|---|---|---|---|
| 5,478,739 A | 12/1995 | Slivka et al. | |
| 5,785,964 A | 7/1998 | Naughton et al. | |
| 5,842,477 A | 12/1998 | Naughton et al. | |
| 5,858,721 A | 1/1999 | Naughton et al. | |
| 5,902,741 A | 5/1999 | Purchio et al. | |
| 5,919,234 A | 7/1999 | Lemperle et al. | |
| 6,022,743 A | 2/2000 | Naughton et al. | |
| 6,082,364 A | 7/2000 | Balian et al. | |
| 6,086,863 A | 7/2000 | Ritter et al. | |
| 6,269,716 B1 | 8/2001 | Amis | |
| 6,284,284 B1 | 9/2001 | Naughton | |
| 6,287,340 B1 | 9/2001 | Altman et al. | |
| 6,391,297 B1 | 5/2002 | Halvorsen | |
| 6,429,013 B1 | 8/2002 | Halvorsen et al. | |
| 6,555,374 B1 | 4/2003 | Gimble et al. | |
| 6,626,854 B2 | 9/2003 | Friedman et al. | |
| 6,777,231 B1 | 8/2004 | Katz et al. | |
| 6,841,150 B2 | 1/2005 | Halvorsen | |
| 6,902,932 B2 | 6/2005 | Altman et al. | |
| 6,986,735 B2 | 1/2006 | Abraham et al. | |
| 6,991,787 B1 | 1/2006 | Greenberger et al. | |
| 7,011,328 B2 | 3/2006 | Rogers et al. | |
| 7,033,587 B2 | 4/2006 | Halvorsen et al. | |
| 7,078,230 B2 | 7/2006 | Wilkison et al. | |
| 7,078,232 B2 | 7/2006 | Konkle et al. | |
| 7,192,604 B2 | 3/2007 | Brown et al. | |
| 7,299,805 B2 | 11/2007 | Bonutti | |
| 7,316,822 B2 | 1/2008 | Binette et al. | |
| 7,452,532 B2 | 11/2008 | Alt | |
| 7,470,537 B2 | 12/2008 | Hedrick et al. | |
| 7,473,420 B2 | 1/2009 | Fraser et al. | |
| 7,501,115 B2 | 3/2009 | Fraser et al. | |
| 7,514,075 B2 | 4/2009 | Hedrick et al. | |
| 7,531,355 B2 | 5/2009 | Rodriguez et al. | |
| 7,585,670 B2 | 9/2009 | Hedrick et al. | |
| 7,625,581 B2 | 12/2009 | Laredo et al. | |
| 7,651,684 B2 | 1/2010 | Hedrick et al. | |
| 7,687,059 B2 | 3/2010 | Fraser et al. | |
| 7,767,452 B2 | 8/2010 | Kleinsek | |
| 7,771,716 B2 | 8/2010 | Hedrick et al. | |
| 7,807,461 B2 | 10/2010 | Kang et al. | |
| 7,875,276 B2 | 1/2011 | Kropp et al. | |
| 7,875,296 B2 | 1/2011 | Binette et al. | |
| 2002/0182211 A1 | 12/2002 | Peach et al. | |
| 2006/0051865 A1 * | 3/2006 | Higgins et al. | ................ 435/366 |
| 2007/0148766 A1 | 6/2007 | Yoshimura et al. | |

FOREIGN PATENT DOCUMENTS

WO    WO 2010026574 A2 *  3/2010

OTHER PUBLICATIONS

Zuk et al., "Human Adipose Tissue Is a Source of Multipotent Stem Cells," Molecular Biology of the Cell, vol. 13, pp. 4279-4295 (2002).*
Ashjian, et al. "In vitro Differentiation of Human Processed Lipoaspirate Cells Into Early Neural Progenitors" (2003) *Plast. Reconstr. Surg.* 111: Cells 1922-19231.
Athanasopoulous, et al. "Gene Therapy Vectors based on Adeno-associated Virus: Characteristics and Applications to Acquired and Inherited Diseases (Review)" (2000) *Int J Mol Med* 6(4): 363-75.
Awad, et al. "Effects of Tansforming on the Growth and Beta1 and Dexamethasone on the Growth and Chondrogenic Differentiation of Adipose-Derived Stromal Cells" (2003) *Tissue Engineering* 9: 1301-1312.
Awad, et al. "Chondrogenic Differentiation of Adipose-Derived Adult Stem Cells in Agarose, Alginate, and Gelatin Scaffolds" (2004) *Biomaterials* 25: 3211-3222.
Aust, et al. "Yield of Human Adipose-Derived Adult Stem Cells from Liposuction Aspirates" (2004) *Cytotherapy* 6: 1-8.
Blumenkrantz, et al. "Characterization of Collagen Hydroxylysyl Glyocosyltranferases As Mainjly Intramembranous Microsomal Enzymes" (1984) *J Biol Chem.* 259(2): 854-9.
Burris, et al. "A Novel Method for Analysis of Nuclear Receptor Function at Natural Promoters", (1999) *Mol Endocrinol* 13: 410-7.
Caplan & Bruder "Mesenchymal Stem Cells: Building for Molecular Medicine in the 21$^{st}$ Century" (2001) *Trends Mol Med* 7(6): 259-64.
Caplan & Goldberg "Principles of Tissue Engineered Regeneration of Skeletal Tissues" (1999) *Clin Orthop* 367 Suppl.: S12-6.

(Continued)

*Primary Examiner* — Sharmila G. Landau
*Assistant Examiner* — Paula D. Pyla
(74) *Attorney, Agent, or Firm* — Hunton & Williams LLP

(57) ABSTRACT

Methods of treating using adipose tissue using ultrasonic cavitation to dissociate the fat cells and blood vessels contained within adipose tissue and thereby obtain mesenchymal or stromal vascular fractions for use in human subjects are provided. These methods preferably do not include the use of any exogenous dissociating enzymes such as collagenase and result in increased numbers of the cells which constitute the mesenchymal or stromal vascular fractions (about 10-fold greater) than methods which use collagenase to isolate these cells.

16 Claims, 43 Drawing Sheets

OTHER PUBLICATIONS

Cousin, et al. "Reconstitution of Lethally Irradiated Mice by Cells Isolated from Adipose Tissue" (2003) *Biochem Biophys Res Commn.* 301: Isolated 1016-1022.

Erickson, et al. "Chondrogenic Potential of Adipose Tissue-Derived Stromal Cells in vitro and in vivo" (2002) *Biochem Biophys Res Commun.* 290: 763-769.

Fukuda "Development of Regenerative Cardiomyocytes from Mesenchymal Stem Cells for Cardiovascular Tissue Engineering" (2001) *Artf Organs* 25(3): 187-93.

Gimble, et al. "Bone Morphogenetic Proteins Inhibit Adipocyte Differentiation by Bone Marrow Stromal Cells" (1995) *J Cell Biochem* 58(3): 393-402.

Gross, et al. "Animal Collagenases: Specificity of Action, and Structures of the Substrate Cleavage Site" (1974) *Biochem Biophys Res. Commun.* 61: 605.

Gronthos, et al. "Surface Protein Characterization of Human Adipose Tissue-Derived Stromal Cells" (2001) *Journal of Cellular Physiology* 189: 54-63.

Hicok, et al. "Human Adipose-Derived Adult Stem Cells Produce Osteoid in vivo" (2004) *Tissue Eng.* 10: 371-380.

Halvorsen, et al. "Thiazolidinediones and Glucocorticoids Synergistically Induce Differentiation of Human Adipose Tissue Stromal Cells: Biochemical, Cellular, and Molecular Analysis" (2001) *Metabolism* 50: 407-413.

Halvorsen, et al. "Extracellular Matrix mineralization and Osteoblast Gene Expression by Human Adipose Tissue-Derived Stromal Cells" (2001) *Tissue Eng.* 7: 729-741.

Harp, et al. "Differential Expression of Signal Transducers and Activators of Transcription During Human Adipogenesis" (2001) *Biochem Biophys Res Commun.* 281:907-912.

Hendricks, et al. "Mesenchymal Stem Cells as Vehicles for Gene Delivery" (2000) *Clin Orthop* 279 Suppl: S71-90.

Hicok, et al. "Human Adipose-Derived Adult Stem Cells Osteoid in vivo" (2004) *Tissue Engineering* 10: 371-380.

Lennon, et al. "A Chemically Defined medium Supports in vitro Proleferation and Maintains The Osteochondral Potential of Rate Marrow-Derived Mesenchymal Stem Cells" (1995) *Exp Cell Res* 219(1): 211-22.

MacFarland "Preparation of Pure Cell Cultures by Cloning" (2000) *Methods in Cell Sci.* 22:63-66.

Majumdar, et al. "Phenotypic and Functional Comparison of Cultures of Marrow-Derived Mesenchymal Stem Cells (MSCs) and Stromal Cells" (1998) *J Cell Physiol.* 176(1): 57-66.

Mizuno, et al. "Myogenic Differentiation by Human Processed Lipoaspirate Cells" (2002) *Plast Reconstr. Surg.* 109: 199-209.

Miranville, et al. "Improvement of Postnatal Neovascularization by Human Adipose Tissue-Derived Stem Cells",(2004) *Circulation* 110: 349-355.

Mosca, et al. "Mesenchymal Stem Cells as Vehicles for Gene Delivery" (2000) *Clin Orthop* 379 Suppl.: S71-90.

Muramatsu, et al. "In vivo Electroporation: A Powerful and Convenient Means of Nonviral Gene Transfer to Tissues of Living Animals (Review)" (1998) *Int J Mol Med* 1(1): 55-62.

Ohgushi & Caplan "Stem Cell Technology and Bioceramics: From Cell to Gene Engineering" (1999) *J Biomed Mater Res* 48(6): 913-27.

Planat-Benard, et al. "Plasticity of Human Adipose Lineage Cells Toward Endothelial Cells . . . ", (2004) *Circulation* 109: 656-663.

Safford, et al. "Neurogenic Differentiation of Murine and Human Adipose-Derived Stromal Cells" (2002) *Biochem. Biophys. Res. Commun.* 294: 371-379.

Safford, et al. "Characterization of Neuronal/Glial Differentiation of Murine Adipose-Derived Adult Stromal Cells" (2004) *Experimental Neurology* 187: 319-328.

Saladin, et al. "Differential Regulation of Peroxisome Proliferator Activated Receptor $\gamma$1 (PPAR $\gamma$1) and PPAR $\gamma$2 Messenger RNA Expression in the Early Stages of Adipogenesis", (1999) *Cell Growth & Diff* 10: 43-48.

Sen et al. "Adipogenic Potential of Human Adipose Stromal cells from Multiple Donors is Heterogeneuous" (2001) *J. Cell. Biochem.* 81:312-319.

Walther & Stein "Viral Vectors for Gene Transfer: A Review of Their Use in the Treatment of Human Diseases" (2000) *Drugs* 60(2): 249-71.

Wickham, et al. "Multipotent Stromal Cells Derived from the Infrapatellar Fat Pad of the Knee" (2003) *Clin. Orthop.* 412: 196-212.

Winter, et al. "Cartilage-Like Gene Expression in Differentiated Human Stem Cell Spheroids", (2003) *Arthritis Rheum.* 48: 418-429.

Worster, et al. "Chondrocytic Differentiation of Mesenchymal Stem Cells Sequentially Exposed to Transforming Growth factor-Beta1 in Monolayer Insulin-Like Growth Factor-I in a Three-Dimensional Matrix" (2001) *J Orthop Rs* 19(4): 738-49.

Zhou, et al. "Analysis of the Pattern of Gene Expression during Human Adipogenics by DNA Microarray" (1999) *Biotechnol. Technologies* 13: 513-517.

Zuk (2002) "Human Adipose Tissue Is a Source of Multipotent Stem Cells", *Mol Biol Cell* 13: 4279-4295.

Zuk et al. "Multilineage Cells from Human Adipose Tissue: Implications for Cell-Based Therapies" (2001) *Tissue Eng*, 7: 211-228.

Ultrasonic cell disruption from London South Bank University (2004).

Traditional Methods of Cell Lysis from Thermo Scientific (2012).

Biyo Seikei Shujutsu Practice 2 (Beauty Surgical Operation Practice 2), ed. Masanari Ichida, Ryusaburo Tanino and Yoshiaki Hosaka published by Bunkodo, pp. 429-469 (2000) [Concise Explanation], only English explanation considered.

Birkedal-Hansen "Catabolism and Turnover of Collagens: Collagenases" (1987) *Methods Enzymol.* 144: 140-71.

Brown, et al. (2009) *Plastic and Reconstructive Surgery* 124(1): 92-101.

Bucco (2009) *Scientifica Acta* 3(2): 73-75.

Mookhtair & Van Wart *Clostridium histolyticum* Collegenases: A New Look at Some Old Enzymes Matrix Suppl. 1: 116 (1992).

Pittenger, et al. "Multilineage Potential of Adult Human Mesenchymal Stem Cells", (1999) *Science* 284(5411): 143-7.

Planat-Benard, et al. "Spontaneous Cardiomyocyte Differentiation From Adipose Tissue Stroma Cells", (2004) *Cir Res.* 94: 223-229.

Woolley, et al. "Action of Rheumatoid Synovial Collagenase on Cartilage Collagen", (1975) *Eur J Biochem* 50(2): 437-444.

\* cited by examiner

ULTRASONIC CAVITATION DERIVED STROMAL OR MESENCHYMAL VASCULAR EXTRACTS AND CELLS DERIVED THEREFROM OBTAINED FROM ADIPOSE TISSUE AND USE THEREOF

RELATED APPLICATIONS

This application claims priority to provisional U.S. Ser. No. 61/427,221 filed on Dec. 27, 2010 the contents of which are incorporated by reference in its entirety.

BACKGROUND OF THE INVENTION

Within the last 10 years, adipose tissues have attracted attention as a resource of multipotent stem cells (See Zuk P A, et al. Mol Biol Cell. 2002; 13: 4279-4295). Adipose tissue consists of mature adipocytes and adipose stromal cells, and the latter can be differentiated into a variety of cell lineages (Zuk P A, et al. Tissue Eng. 2001; 7: 211-228; Hicok K C, et al. Tissue Eng. 2004; 10: 371-380; Erickson G R, et al. Biochem Biophys Res Commun. 2002; 290: 763-769; Cousin B, et al. Biochem Biophys Res Commun. 2003; 301: 1016-1022; Safford K M, et al. Biochem Biophys Res Commun. 2002; 294: 371-379; Miranville A, et al. Circulation. 2004; 110: 349-355; Planat-Benard V, et al. Circ Res. 2004; 94: 223-229; and Planat-Benard V, et al. Circulation. 2004; 109: 656-663) The adipose stromal cells are adhesive and can proliferate in culture. Therefore, a large amount of adipose stromal cells can be readily obtained from a small piece of adipose tissue by means of culture.

Presently in order to produce stromal vascular fraction from adipose tissue an enzyme such as collagenase is typically used. The collagenase dissolves the bonds in the collagen that hold together the tissue. (See e.g., Zuk P A, et al. Mol Biol Cell. 2002; 13: 4279-4295; Zuk P A, et al. Tissue Eng. 2001; 7: 211-228; et al. and the above-cited references).

Collagenases are endopeptidases that digest native collagen in the triple helix region. Collagens are the major fibrous component of animal extracellular connective tissue. Collagenases are present in different organisms including vertebrates and bacteria. Bacterial collagenases have a broad substrate specificity than vertebrate collagenases (See Blumenkrantz et al., J Biol Chem. 1984 Jan. 25; 259(2):854-9; Birkedal-Hansen Methods Enzymol. 1987; 144:140-71. 1987). In addition unlike bacterial derived collagenases split collagen into its native triple helix conformation (See Wooley et al. Eur J Biochem 50(2):437-444, 1975; Gross et al., Animal Collagenases: Specificity of Action, and Structures of the Substrate Cleavage Site, Biochem. Biophys. Res. Commun. 61, 605, 1974). Bacterial collagenases are distinct in that they are capable of breaking down both water-insoluble native collagens and water-soluble denatured collagens. Bacterial collagenases is capable of breaking down almost all types of collagen and can effect multiple cleavages within the triple helical regions (see Mookhtiar and Van Wart *Clostridium histolyticum* Collagenases: A New Look at some Old Enzymes, Matrix Suppl. 1, 116, 1992).

A recent patent application 20070148766, published Jun. 28, 2007, by Yoshimura; Kotaro; (Shibuya-ku, JP); Matsumoto; Daisuke and assigned to Biomaster Inc., teaches the isolation of stem cells from liposuction-derived aspirates.

BRIEF DESCRIPTION OF THE INVENTION

The invention provides a novel method of obtaining a mesenchymal or stromal vascular fraction from adipose tissue that does not include the use of collagenase or other enzymes to digest the collagen bonds that hold together the tissue. While collagenase works well for this purpose, and indeed is conventionally used by those skilled in the art to degrade collagen and separate the tissue into discrete cells, the use of this enzyme may be disadvantageous for cellular products that are to be used in humans, e.g., cells or cell fractions which are to be used in tissue reconstruction or regeneration, e.g., breast reconstruction procedures, cosmetic skin rejuvenation or usage in cosmetic tissue fillers that are used during plastic surgery. Particularly the FDA may consider that the use of this enzyme (to derive desired cells) results in a "maximally manipulated" cellular product. This is disadvantageous as the use of collagenase would potentially place stromal or mesenchymal vascular cells derived from adipose tissue in a category that requires drug approval, even if the cell fraction is to be used cosmetically and not clinically.

Also, the use of enzymes such as collagenase is further disfavored as these enzymes result in more cell death, thereby reducing the number of the desired cells which are isolatable, and further this results in more cellular debris, thereby resulting in a less useful cell product, especially if the cells are to be used therapeutically. Accordingly it would be desirable to provide alternative methods, e.g., mechanical methods, that produce a stromal or mesenchymal vascular fraction (containing mesenchymal or stromal stem cells, endothelial cells, and other cells found in adipose tissues) which is suitable for administration to patients via local or systemic administration such as via injection, infusion, topical administration, or which is administered in association with implants, matrices, tissue fillers, wherein the adipose tissue derived composition does not include collagenase and is not "maximally manipulated" according to the FDA.

As discussed supra the present inventor has discovered that adipose tissues, e.g., derived from surgical excision or aspirated via liposuction may be treated ex vivo by ultrasonic cavitation for a sufficient amount of time to explode or lyse the fat cells and the blood vessels contained therein thereby releasing the stromal vascular fraction cells contained within the outer layer of blood vessel walls contained in the adipose tissue including stromal and mesenchymal stem cells, endothelial precursor cells, and other cell types which constitute the "mesenchymal vascular fraction" or the "stromal vascular fraction". The present inventor has found that the treatment of adipose tissue by use of ultrasonic cavitation under appropriate conditions such as exemplified in the working examples, not only explodes or lyses the fat cells, but further explodes or lyses the blood vessels contained therein, without adversely affecting the viability of stromal and mesenchymal stem cells, thereby releasing high numbers of viable stromal and mesenchymal stem cells, endothelial precursor cells, and other cell types which constitute the "mesenchymal vascular fraction" or the "stromal vascular fraction" which stromal and mesenchymal stem cells may be recovered and used in desired cosmetic or therapeutic methods wherein these cells are of beneficial value.

To the best of the inventor's knowledge the successful use of this mechanical means in the absence of protease in order to derive a mesenchymal or stromal vascular fraction from adipose tissue suitable for administration to human subjects has not previously been successfully used. Whereas published patent application US20060051865 (abandoned prior to substantive examination) purports to describe the use of ultrasonic methods to release adult stem cells from adipose tissue, especially in Example 2, when the present inventor reproduced their methods and disclosed operating conditions they were ineffective, i.e., they yielded few stromal vascular fraction cells. By contrast, the present invention reproducibly results in very high numbers of viable stromal vascular fraction cells, which are well suited for use in cell therapy or cosmetic procedures.

By contrast, the use of ultrasonic cavitation or lipocavitation is well known as a non invasive treatment which helps in the reduction of localized fat deposits. This method is used for people who are dissatisfied with a certain area of fatty deposits but who do not want to undergo any invasive surgical treatment like liposuction. It is performed as a walk in, walk out treatment and there is no lengthy recovery period as with surgical fat removal.

A good candidate for lipocavitation is someone looking for fat removal from a specific area such as the hips, thighs, buttocks, stomach or arms. The treatment does not generally result in overall weight loss, but an improved contour in the localized treatment area.

In the treatment the handpiece delivers low frequency ultrasound waves down into the subcutaneous or fatty layer of the skin, targeting the adipocytes or fat cells. The minute vibrations produce tiny bubbles within the fat cells which disturb the outer membrane and allow tiny collections of fat to be expelled into the surrounding area, which then is removed via the body's natural energy and waste removal processes. This selective destruction of fat cells does not interfere with adjacent structures such as blood vessels and nerves and is therefore a very safe treatment. Lipocavitation is a painless procedure, though for some people there may be a little discomfort associated with the noise during treatment which ceases when the handpiece is no longer in contact with the skin.

By contrast, in the present invention ultrasonic cavitation is used to mechanically treat adipose tissue ex vivo in the absence of collagenase to lyse fat cells and the blood cells contained therein and the resultant sonically treated composition (from which the fat is removed) is then used to obtain a mesenchymal or stromal vascular fraction which can be infused directly in patients in need thereof or it can be further processed to purify (and expand in culture if desired) desired cell types such as mesenchymal or stromal stem cells, endothelial cells, and other cells found in adipose tissue. These fractions and cells may be used in patients such as for tissue reconstruction, tissue regeneration, wound healing, breast augmentation or reconstruction, in tissue fillers for plumping areas that have lost fullness, such as via aging or because of disease such as the face, lips, the buttocks, and the like. In particular, contemplated uses of these cells include use with or in lieu of tissue fillers, e.g., for treating gum recession, loss of bone, including e.g., the jaw, treatment of orthopedic problems, treatment of arthritis, treatment of migraine, treatment of multiple sclerosis, treatment of autism, treatment of diabetes, treatment of wounds, treatment of ulcers, treatment of COPD, treatment of plantar fascitis, treatment of rotator cuff, and treatment of tennis elbow.

OBJECTS OF THE INVENTION

Figure 1A:
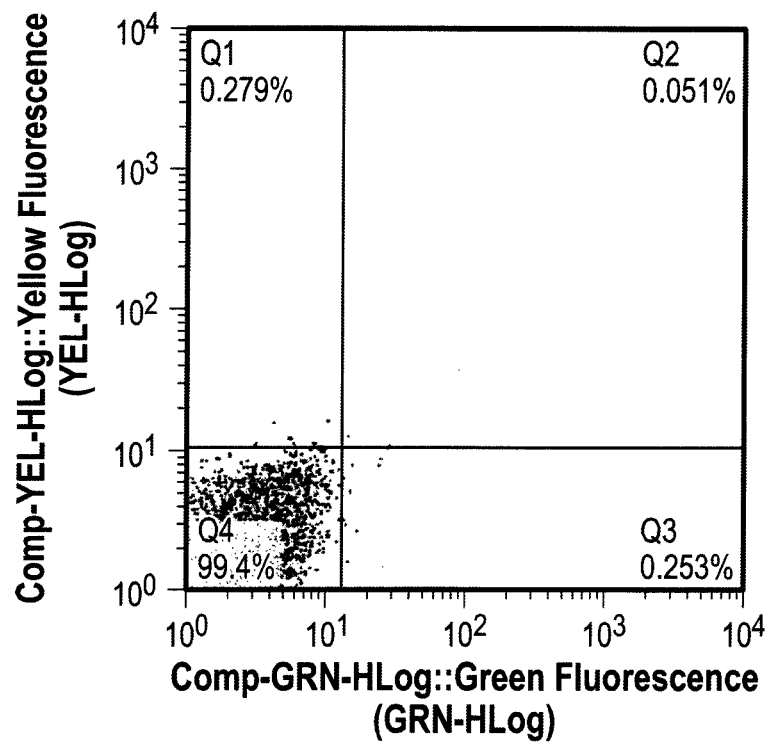
FIGS. 1A-E, 2A-E, 3A-E, 4A-E and 5A-E contain the results of Milipore studies that compare the stromal vascular fraction cells isolated according to the inventive ultrasonication methods vis-à-vis methods that use collagenase. The results therein show that the subject ultrasonication protocol results in about 10-fold more viable cells than comparable adipose samples (same amount of adipose tissue) which were treated with an enzyme that breaks down collagen (collagenase). The results therein further show that the inventive methods result in the same cell population and cell types as collagenase isolation procedures, suggesting that the inventive methods preserve the integrity of all the desired stromal vascular fraction cells, and especially the cell types identified in the Figures.
Figure 1A:
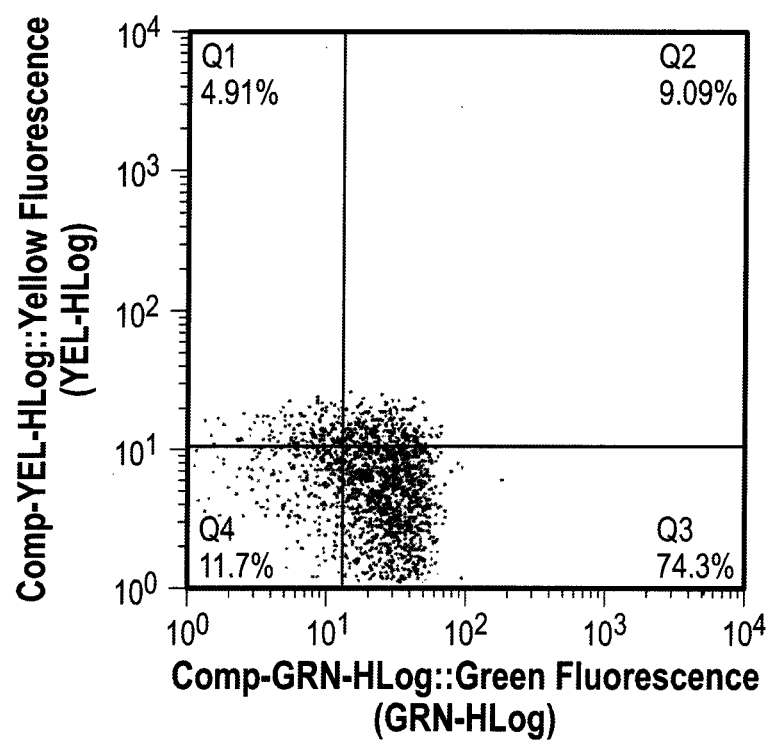
Figure 1A:
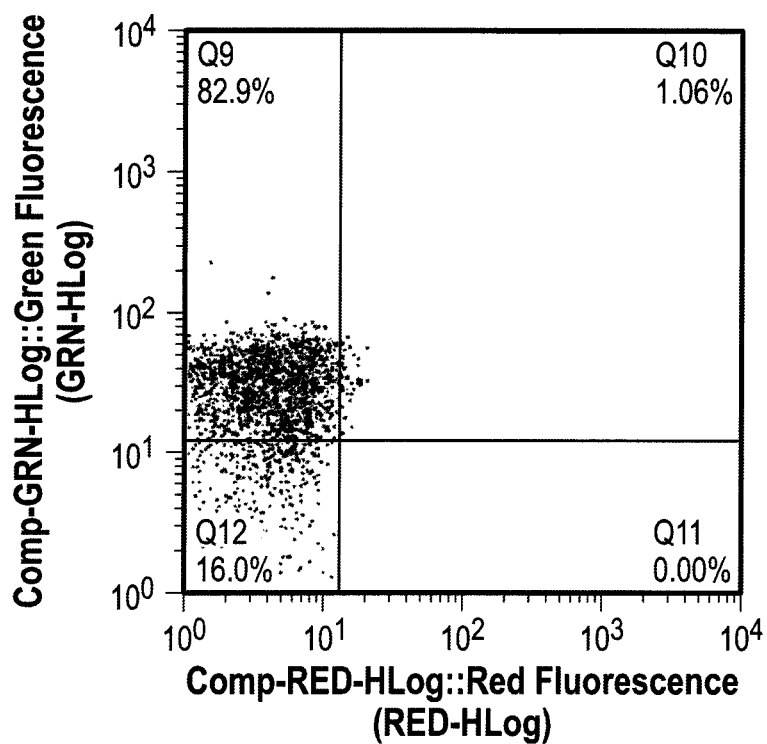
Figure 1A:
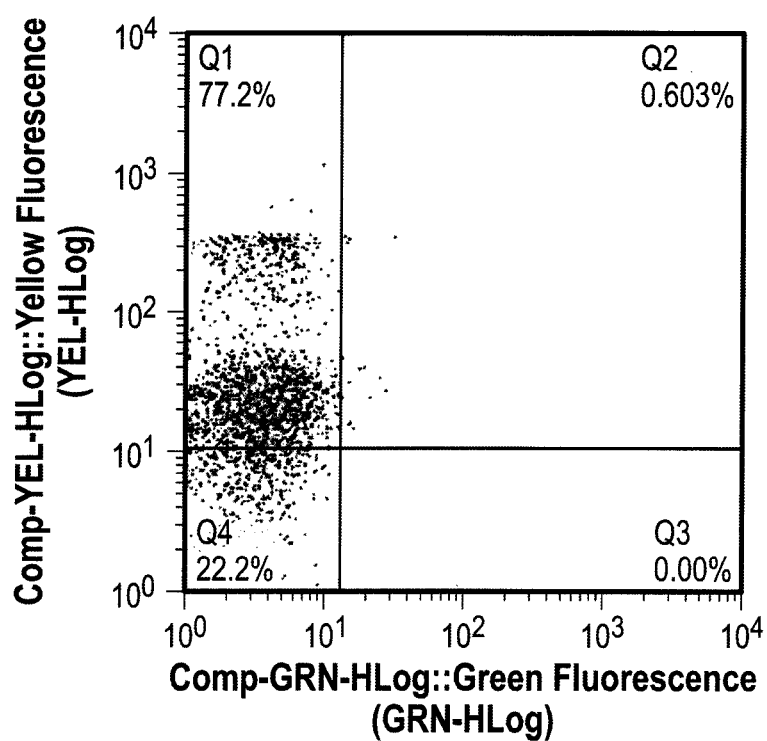
Figure 1A:
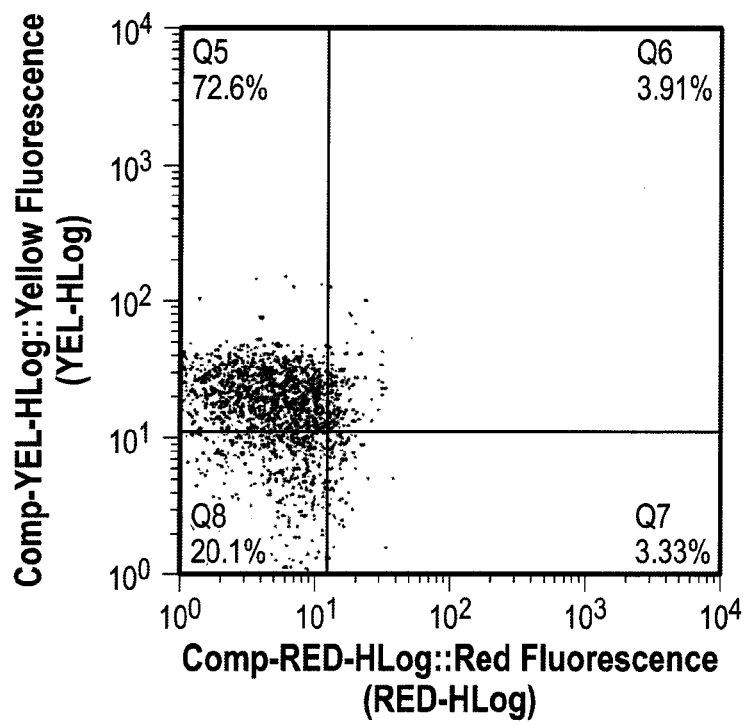
Figure 1A:
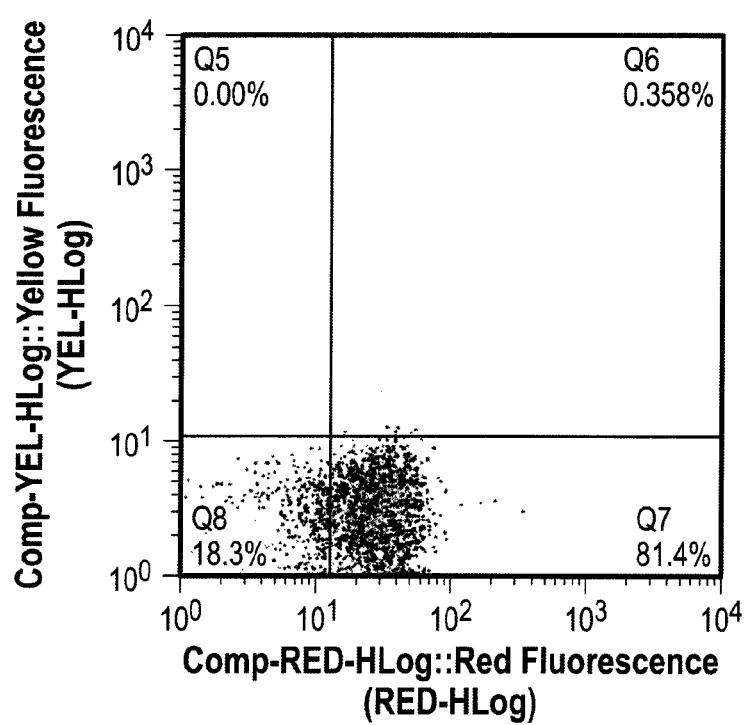
Figure 1A:
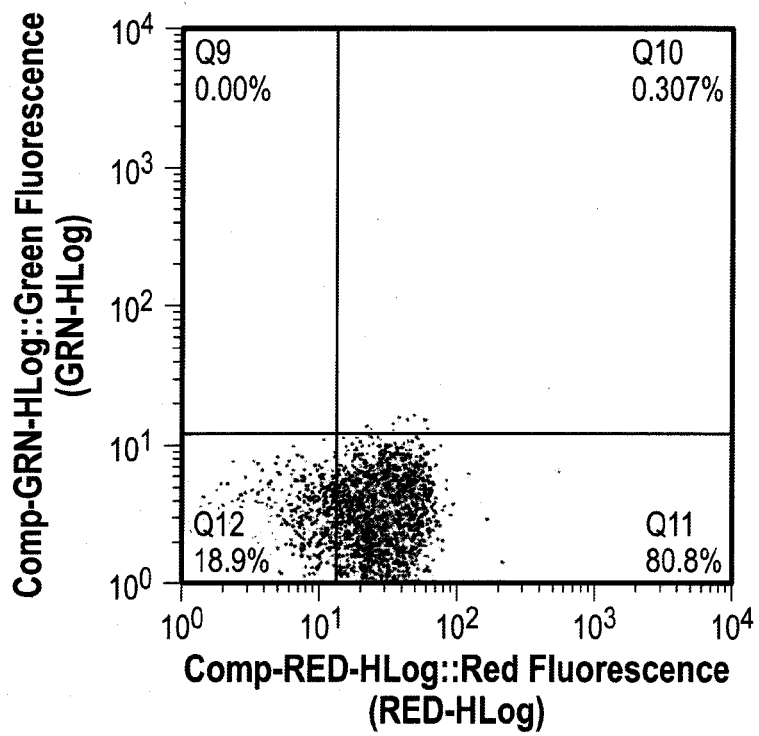

It is an object of the invention to produce a mesenchymal or stromal vascular fraction from vascular tissues contained in adipose tissue which contains vascular tissue-derived stem cells and other cells found in the walls of blood vessels without the use of collagenase or another enzyme that cleaves collagen bonds.

It is a specific object of the invention to produce a mesenchymal or stromal vascular fraction from adipose tissue, which method comprises treating adipose tissue with ultrasonic cavitation under conditions whereby that the fat cells in the sample are exploded or lysed, and in addition under ultrasonication conditions whereby the blood vessels found in the fat are further lysed without adversely affecting the viability of stromal and mesenchymal stem cells contained therein. It has been found that by the judicious optimization of ultrasonication conditions as described herein, that ultrasonication methods may be used in the absence of protease treatment to release the desired stromal vascular or mesenchymal vascular cells from the blood vessels found in the adipose tissue without adversely affecting the stromal and mesenchymal stem cells substantial lysis or degradation of the stromal and mesenchymal stem cells. Preferably, the methods will not include the addition of an enzyme that breaks down collagen such as a collagenase or other endopeptidase.

It is a more specific object of the invention to produce a mesenchymal or stromal vascular fraction and specific cell types contained therein from adipose tissue surgically obtained from the stromal or mesenchymal compartment of the body of a donor or derived from a liposuction derived aspirate.

In a preferred embodiment the method will includes the use of an ultrasonic cavitation device having a probe that is placed into contact with the adipose tissue and wherein the contact is sufficient (e.g., 1 minute to about 8 hrs, more preferably about 5 minutes to about 1 hour) so as to explode or lyse most of the fat cells in the adipose tissue and blood cells under conditions that release the stromal vascular fraction containing stromal and mesenchymal stem cells, endothelial precursors and other cell types contained therein without adversely affecting the viability and number of these cells from different samples. In fact, as disclosed herein the present invention results in the recovery of increased numbers of viable stromal and mesenchymal stem cells (about ten-fold more) from adipose samples relative to prior art methods using collagenase or other enzymes.

In another preferred embodiment after ultrasonic cavitation the exploded fat (at the top of the composition) will be removed and the remaining fraction further purified or assayed (such as by flow cytometry) for the presence of desired cell types including stem and endothelial precursor cells, immune cells, osteoclasts, hematopoietic stem cells, and other cell types disclosed herein.

In another preferred embodiment after ultrasonic cavitation the mesenchymal or stromal stem cells are isolated from the sample such as by flow cytometry or may be fractionated into different cell types using fluorescence activated call sorting (FACS) based on cell surface antigens which are specific to adipose-derived stem cells or other cell lineages contained in adipose tissue.

In another preferred embodiment after ultrasonic cavitation the isolated mesenchymal or stromal stem cells or other cells are derived therefrom are infused or administered into a patient for a specific cosmetic or therapeutic procedure.

In another preferred embodiment the isolated mesenchymal or stromal stem cells or other cells are derived therefrom are used to promote wound healing, breast augmentation or reconstruction, tissue engineering, or other applications.

In another preferred embodiment the invention provides a stromal or mesenchymal vascular fraction derived from adipose tissue that does not comprise any exogenous collagenase.

In another preferred embodiment the vascular fraction will comprise stem and other cells that express at least one protein selected from the group consisting of CD13, CD14, CD29, CD31, CD34, CD36, CD44, CD45. CD49d, CD54, CD58, CD71, CD73, CD90, CD105, CD106, CD151 and SH3, or CD13, CD29, CD34, CD36, CD44, CD49d, CD54, CD58, CD71, CD73, CD90, CD105, CD106, CD151 and SH3 and/or CD31, CD45, CD117 and CD146 and do not express CD56.

In another preferred embodiment the vascular fraction will comprise stem and other cells that express at least one protein selected from the group consisting of CD3, CD4, CD14, CD15, CD16, CD19, CD33, CD38, CD56, CD61, CD62e, CD62p, CD69, CD104, CD135 and CD144, and does not express CD3, CD4, CD14, CD15, CD16, CD19, CD33, CD38, CD56, CD61, CD62e, CD62p, CD69, CD104, CD135 and CD144 or expresses CD49d and do not express CD56.

DETAILED DESCRIPTION OF THE INVENTION

Before describing the invention in detail the following abbreviations and definitions for words used throughout this application are provided.

ASC or ADSC, Adipose-Derived Stem Cell; Herein this refers to mesenchymal stem cells derived from blood vessels found in adipose tissue, e.g., CD34 expressing hematopoietic stem cells.

BMI, Body Mass Index.

The articles "a" and "an" are used herein to refer to one or to more than one (i.e., to at least one) of the grammatical object of the article. By way of example, "an element" means one element or more than one element.

The term "about" will be understood by persons of ordinary skill in the art and will vary to some extent based on the context in which it is used.

The term "adipose tissue-derived cell" herein refers to a cell that originates from adipose tissue, preferably from the blood vessels contained therein. The initial cell population isolated from adipose tissue is a heterogeneous cell population including, but not limited to stromal or mesenchymal vascular fraction (SVF) or (MVF) cell.

"Adipose" refers to any fat tissue. The adipose tissue may be brown or white adipose tissue. The adipose may be mesenchymal or stromal. Preferably, the adipose tissue is subcutaneous white adipose tissue. The adipose tissue may be from any organism having fat tissue. Preferably the adipose tissue is mammalian, most preferably the adipose tissue is human. A convenient source of human adipose tissue is that derived from liposuction surgery or other surgery. However, the source of adipose tissue or the method of isolation of adipose tissue is not critical to the invention.

As used herein, the term "adipose-derived stem cell (ADSC or ASC)" refers to stromal or mesenchymal cells that originate from blood vessels found in adipose tissue which can serve as stem cell-like precursors to a variety of different cell types such as but not limited to adipocytes, osteocytes, chondrocytes, muscle and neuronal/glial cell lineages. Adipose-derived stem cells make up a subset population derived from adipose tissue which can be separated from other components of the adipose tissue using standard culturing procedures or other methods disclosed herein. In addition, adipose-derived adult stem cells can be isolated from a mixture of cells using the cell surface markers disclosed herein.

As used herein, the term "adipose cell" is used to refer to any type of adipose tissue, including an undifferentiated adipose-derived adult stem cell and a differentiated adipose-derived adult stem cell.

As used herein the phrase "Mesenchymal or stromal vascular fraction" refers to a cell fraction derived from blood vessels found in adipose tissue that comprises different cell types including by way of example mesenchymal stem cells, hematopoietic cells, hematopoietic stem cells, platelets, Kupffer cells, osteoclasts, megakaryocytes, granulocytes, NK cells, endothelial precursor or progenitor cells, CD34+ cells or mesenchymal stem cells, (typically found in umbilical cord), CD29+ cells, CD166+ cells, Thy-1+ or CD90+ stem cells, CD44+ cells, immune cells such as monocytes, leukocytes, lymphocytes, B and T cells, NK cells, macrophages, neutrophil leukocytes, neutrophils, neutrophil granulocytes, and the like including immune and other cells that express one or more of the following markers: CD3, CD14 (macrophage marker), CD19, CD20 (B cell marker), CD29 (integrin unit), CD31 (endothelial, platelet, macrophage, Kupffer cell, dendritic cell, granulocyte, T/NK cells, lymphocytes, megakaryocytes, osteoclasts, neutrophils, et al.), CD44 (Hyaluronic acid receptor), CD45 (B and T cell marker), C56, CD73 (lymphocyte differentiation marker), CD105 et al. Also, it includes cells expressing any of the markers or any combination thereof disclosed in this application.

As used herein, the term "allogeneic" is meant to refer to any material derived from a different mammal of the same species.

As used herein, the term "autologous" is meant to refer to any material derived from the same individual to which it is later to be re-introduced.

As used herein, the term "phenotypic characteristics" should be construed to mean at least one of the following characteristics: morphological appearance, the expression of a specific protein, a staining pattern or the ability to be stained with a substance.

By the term "applicator," as the term is used herein, is meant any device including, but not limited to, a hypodermic syringe, a pipette, and the like, for administering the compounds and compositions of the invention.

As used herein, "central nervous system" should be construed to include brain and/or the spinal cord of a mammal. The term may also include the eye and optic nerve in some instances.

"Differentiated" is used herein to refer to a cell that has achieved a terminal state of maturation such that the cell has developed fully and demonstrates biological specialization and/or adaptation to a specific environment and/or function. Typically, a differentiated cell is characterized by expression of genes that encode differentiation-associated proteins in that cell. For example expression of GALC in a leukocyte is a typical example of a terminally differentiated leukocyte.

"Differentiation medium" is used herein to refer to a cell growth medium comprising an additive or a lack of an additive such that a stem cell, adipose tissue derived stromal cell, embryonic stem cell, ES-like cell, MSCs, neurosphere, NSC or other such progenitor cell, that is not fully differentiated when incubated in the medium, develops into a cell with some or all of the characteristics of a differentiated cell.

When a cell is said to be "differentiating," as that term is used herein, the cell is in the process of being differentiated.

A "differentiated adipose-derived adult stem cell" is an adipose-derived adult stem cell isolated from any adipose tissue that has differentiated as defined herein.

An "undifferentiated adipose-derived adult stem cell" is a cell isolated from adipose tissue and cultured to promote proliferation, but has no detectably expressed proteins or other phenotypic characteristics indicative of biological specialization and/or adaptation.

A "disease" is a state of health of an animal wherein the animal cannot maintain homeostasis, and wherein if the disease is not ameliorated, then the animal's health continues to deteriorate. In contrast, a "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

As used herein, the term "disease, disorder or condition of the central nervous system" is meant to refer to a disease, disorder or a condition which is caused by a genetic mutation in a gene that is expressed by cells of the central nervous system or cells that affect the central nervous system such that one of the effects of such a mutation is manifested by abnormal structure and/or function of the central nervous system, such as, for example, defective myelin. Such genetic defects may be the result of a mutated, non-functional or under-expressed gene in a cell of the central nervous system.

As used herein "endogenous" refers to any material from or produced inside an organism, cell or system.

"Exogenous" refers to any material introduced from or produced outside an organism, cell, or system. In particular exogenous may refer to a material that is not present in the treated adipose tissue.

An "isolated cell" refers to a cell which has been separated from other components and/or cells which naturally accompany the isolated cell in a tissue or mammal.

As used herein, a "graft" refers to a cell, tissue or organ that is implanted into an individual, typically to replace, correct or otherwise overcome a defect. A graft may further comprise a scaffold. The tissue or organ may consist of cells that originate from the same individual; this graft is referred to herein by the following interchangeable terms: "autograft", "autologous transplant", "autologous implant" and "autologous graft". A graft comprising cells from a genetically different individual of the same species is referred to herein by the following interchangeable terms: "allograft", "allogeneic transplant", "allogeneic implant" and "allogeneic graft". A graft from an individual to his identical twin is referred to herein as an "isograft", a "syngeneic transplant", a "syngeneic implant" or a "syngeneic graft". A "xenograft", "xenogeneic transplant" or "xenogeneic implant" refers to a graft from one individual to another of a different species.

"Immunophenotype" of a cell is used herein to refer to the phenotype of a cell in terms of the surface protein profile of a cell.

"Polypeptide" refers to a polymer composed of amino acid residues, related naturally occurring structural variants, and synthetic non-naturally occurring analogs thereof linked via peptide bonds, related naturally occurring structural variants, and synthetic non-naturally occurring analogs thereof. Synthetic polypeptides can be synthesized, for example, using an automated polypeptide synthesizer.

The terms "precursor cell," "progenitor cell," and "stem cell" are used interchangeably in the art and herein and refer either to a pluripotent, or lineage-uncommitted, progenitor cell, which is potentially capable of an unlimited number of mitotic divisions to either renew itself or to produce progeny cells which will differentiate into the desired cell type. In contrast to pluripotent stem cells, lineage-committed progenitor cells are generally considered to be incapable of giving rise to numerous cell types that phenotypically differ from each other. Instead, progenitor cells give rise to one or possibly two lineage-committed cell types.

As used herein, the term "multipotential" or "multipotentiality" is meant to refer to the capability of a stem cell to differentiate into more than one type of cell.

As used herein, the term "late passaged adipose tissue-derived stromal cell," refers to a cell exhibiting a less immunogenic characteristic when compared to an earlier passaged cell. The immunogenicity of an adipose tissue-derived stromal cell corresponds to the number of passages. Preferably, the cell has been passaged up to at least the second passage, more preferably, the cell has been passaged up to at least the third passage, and most preferably, the cell has been passaged up to at least the fourth passage.

The term "protein" typically refers to large polypeptides, typically over 100 amino acids.

The term "peptide" typically refers to short polypeptides, typically under 100 amino acids.

A "therapeutic" treatment is a treatment administered to a patient who exhibits signs of pathology for the purpose of diminishing or eliminating those signs and/or decreasing or diminishing the frequency, duration and intensity of the signs.

A "therapeutically effective amount" of a compound is that amount of compound or cells which is sufficient to provide a beneficial effect to the subject to which the compound is administered. Also, as used herein, a "therapeutically effective amount" is the amount of cells which is sufficient to provide a beneficial effect to the subject to which the cells are administered.

A "cosmetically or aesthetically effective amount" of a compound or cells is that amount of compound or cells which is sufficient to provide a cosmetically or aesthetically beneficial effect to the subject to which the compound or cells are administered such as skin rejuvenation, enhancement in plumpness or volume or appearance of treated tissue such as the cheeks, lips, buttocks, or breast tissue. Also, as used herein, a "cosmetically effective amount" is the amount of cells which is sufficient to provide a beneficial effect to the subject to which the cells are administered.

To "treat" a disease as the term is used herein, means to reduce the frequency of the disease or disorder reducing the frequency with which a symptom of the one or more symptoms disease or disorder is experienced by an animal.

"Xenogeneic" refers to any material derived from a mammal of a different species.

The invention provides a novel method of obtaining a stromal vascular fraction from adipose tissue that preferably does not include or require the use of collagenase or other enzymes to digest the collagen bonds that hold together the tissue. While collagenase works well for this purpose, and indeed is conventionally used by those skilled in the art to degrade collagen and separate the tissue into discrete cells, the use of this enzyme may be disadvantageous for cellular products that are to be used in humans, e.g., cells or cell fractions which are to be used in tissue reconstruction or tissue regeneration, e.g., breast reconstruction procedures such as for skin rejuvenation or in cosmetic tissue fillers that are conventionally used during plastic surgery. As noted previously the FDA may consider that the use of this enzyme to derive desired cells results in a "maximally manipulated" product. This is disadvantageous as the use of collagenase would potentially place stromal vascular cells derived from adipose tissue in a category that requires drug approval, even if the cell fraction is used cosmetically and not clinically. Also, such enzymes result in more cell death and cell debris. Accordingly it would be desirable to provide alternative methods, e.g., mechanical methods, that produce a stromal vascular fraction (containing mesenchymal or stromal stem cells, endothelial cells, and other cells found in blood vessels in adipose tissues) suitable for administration to patients via local or systemic administration such as via injection, infusion, topical, or in association with implants, matrices, tissue fillers, wherein the adipose cell derived composition does not include collagenase and which compositions are not "maximally manipulated" according to the FDA.

As further discussed supra the present inventor has discovered that adipose tissues, e.g., derived from surgical excision or aspirated via liposuction may be treated by ultrasonic cavitation for a sufficient amount of time to explode or lyse the fat cells and the blood vessels contained therein and thereby release stromal vascular fraction cells contained within the blood vessels in the adipose tissue including stromal and mesenchymal stem cells, endothelial precursor cells, and other cell types which constitute the mesenchymal or stromal vascular fraction.

In the present invention ultrasonic cavitation is used to mechanically treat adipose tissue ex vivo preferably in the absence of exogenous collagenase to lyse fat cells and the resultant sonically treated composition (from which the fat is removed) is then used to obtain a mesenchymal or stromal vascular fraction which can be infused directly in patients in need thereof or it can be further processed to purify (and expand in culture if desired) desired cell types such as mesenchymal or stromal stem cells, endothelial cells, and other cells found in adipose tissue. These fractions and cells may be used in patients such as for tissue reconstruction, tissue regeneration, wound healing, breast augmentation or reconstruction, in tissue fillers for plumping areas that have lost fullness, such as via aging or because of disease such as the face, lips, the buttocks, and the like.

In general the invention produces a mesenchymal or stromal vascular fraction from adipose tissue by treating adipose tissue with ultrasonic cavitation under conditions whereby that the fat cells in the sample are exploded or lysed thereby releasing the stromal vascular or mesenchymal vascular cells from the adipose tissue and which preferably does not include the addition of an enzyme that breaks down collagen such as a collagenase or other endopeptidase. The adipose tissue may be derived from any mammal but preferably is from a living or non-living donor. The adipose tissue may be obtained via liposuction surgery, aspiration of fat after these procedures or isolated by other surgical methods. The donor will preferably be the same patient who is to be treated with the stromal or mesenchymal vascular fraction or cells derived therefrom or will be an allogeneic donor that is immune compatible with the treated individual.

In a preferred embodiment the method uses an ultrasonic cavitation device having a probe that is placed into contact with the adipose tissue and wherein the contact is for a sufficient time (e.g., 1 minute to about 8 hrs, more preferably about 5 minutes to about 1 hour.) so as to explode or lyse most of the fat cells in the adipose tissue and release the stromal vascular fraction containing stromal and mesenchymal stem cells, endothelial precursors and other cell types.

The particular ultrasonic cavitation device used is not critical to the invention. One suitable selection is the Vibra-Cell™ device which is a technologically advanced high intensity ultrasonic processor. This device can safely process a wide range of organic and inorganic materials—from microliters to liters. Other devices which may be used include HIELSCHLER SONIC 200, and SONIC 200.

After the adipose tissue containing blood vessels is treated using the ultrasonic cavitation device the exploded fat (at the top of the composition) is preferably removed and the remaining stromal or mesenchymal vascular fraction from the lysed or exploded blood vessels may be further purified or assayed (such as by flow cytometry) for the presence of desired cell types including stem and endothelial precursor cells. This may be effected by known methods including flow cytometry or fractionation into different cell types using fluorescence activated call sorting (FACS), e.g., based on cell surface antigens which are specific to adipose-derived stem cells or other cell lineages contained in adipose tissue. Suitable antigens and markers are disclosed herein. Cell contained therein and markers isolatable from adipose tissue according to the invention include by way of example mesenchymal stem cells, hematopoietic cells, hematopoietic stem cells, platelets, Kupffer cells, osteoclasts, megakaryocytes, granulocytes, NK cells, endothelial precursor or progenitor cells, CD34+ cells or mesenchymal stem cells, (typically found in umbilical cord), CD29+ cells, CD166+ cells, Thy-1+ or CD90+ stem cells, CD44+ cells, immune cells such as monocytes, leukocytes, lymphocytes, B and T cells, NK cells, macrophages, neutrophil leukocytes, neutrophils, neutrophil granulocytes, and the like including immune and other cells that express one or more of the following markers: CD3, CD14 (macrophage marker), CD19, CD20 (B cell marker), CD29 (integrin unit) CD31 (endothelial, platelet, macrophage, Kupffer cell, granulocyte, T/NK cells, lymphocytes, megakaryocytes, osteoclasts, neutrophils, et al.), CD44 (Hyaluronic acid receptor) CD45 (B and T cell marker), C56, CD73 (lymphocyte differentiation marker), CD105 et al. Also, it includes cells expressing any of the markers disclosed in this application or any combination of these markers.

The isolated stromal or mesenchymal vascular fraction or isolated cells are preferably administered into a patient in need thereof. For example the stem cells are used to promote wound healing, breast augmentation or reconstruction, tissue engineering, or other applications.

This fraction will preferably comprise adipose-derived stem cells that express at least one protein selected from the group consisting of CD13, CD29, CD34, CD36, CD44, CD49d, CD54, CD58, CD71, CD73, CD90, CD105, CD106, CD151 and SH3, or CD13, CD29, CD34, CD36, CD44, CD49d, CD54, CD58, CD71, CD73, CD90, CD105, CD106, CD151 and SH3 and/or CD31, CD45, CD117 and CD146 and will not express CD56.

In another preferred embodiment the vascular fraction will comprise stem cells that express at least one protein selected from the group consisting of CD3, CD4, CD14, CD15, CD16, CD19, CD33, CD38, CD56, CD61, CD62e, CD62p, CD69, CD104, CD135 and CD144, and does not express CD3, CD4, CD14, CD15, CD16, CD19, CD33, CD38, CD56, CD61, CD62e, CD62p, CD69, CD104, CD135 and CD144 or expresses CD49d and does not express CD56.

While the vascular fraction or isolated cells derived from adipose tissue may be used directly for treatment, alternatively the cells may be expanded in culture such that a single milliliter of tissue yields over 400,000 cells (Aust, et al., 2004, Cytotherapy 6: 1-8). Undifferentiated human adipocyte cells express a distinct immunophenotype based on flow cytometric analyses and, following induction, produce additional adipocyte specific proteins (Aust, et al., 2004, Cytotherapy 6: 1-8; 2001, J. Cell Physiol., 189: 54-63; Halvorsen, et al., 2001, Metabolism 50: 407-413; Sen, 2001, J. Cell. Biochem. 81: 312-319; Zuk, et al., 2002, Mol. Biol. Cell. 13: 4279-4295). Human adipose-derived adult stem cells (huASCs) display multipotentiality, with the capability of differentiating along the adipocyte, chondrocyte, myogenic, neuronal, and osteoblast lineages Aust, et al., 2004, Cytotherapy 6: 1-8; 2001, J. Cell Physiol., 189: 54-63; Halvorsen, et al., 2001, Metabolism 50: 407-413; Sen, 2001, J. Cell. Biochem. 81: 312-319; Zuk, et al., 2002, Mol. Biol. Cell. 13: 4279-4295; Ashjian, et al., 2003, Plast. Reconstr. Surg., 111: 1922-19231; Awad, et al., 2003, Tissue Engineering, 9: 1301-1312; Awad, et al., 2004, Biomaterials 25: 3211-3222; Halvorsen, et al., 2001, Tissue Eng., 7: 729-741; Hicok, et al., 2004, Tissue Engineering 10: 371-380; Mizuno, et al., 2002, Plast. Reconstr. Surg. 109: 199-209; Safford, et al., 2002, Biochem. Biophys. Res. Commun., 294: 371-379; Safford, et al., 2004, Experimental Neurology, 187: 319-328; Wickham, et al., 2003, Clin. Orthop., 412: 196-212; Winter, et al., 2003, Arthritis Rheum., 48: 418-429; Zuk, et al., 2001, Tissue Eng. 7: 211-28). In the presence of dexamethasone, insulin, isobutylmethylxanthine and a thiazolidinedione, the undifferentiated human adipocyte cells undergo adipogenesis as evidenced by the fact that between 30% to 80% of the cells, based on flow cytometric methods, accumulate lipid vacuoles, which can be stained for neutral lipid with Oil Red O dye (Halvorsen, et al., 2001, Metabolism 50: 407-413; Sen, et al., 2001, J. Cell. Biochem., 81: 312-319).

In some embodiments, somatic tissue stem cells can be isolated from the subject stromal or mesenchymal vascular fraction by fractionation using fluorescence activated call sorting (FACS) with unique cell surface antigens to isolate specific subtypes of stem cells (such as adipose derived stem cells) for injection into recipients following expansion in vitro, as described above. As stated above, cells may be derived from the individual to be treated or a matched donor. Those having ordinary skill in the art can readily identify matched donors using standard techniques and criteria.

Methods to isolate and expand SVFC's are known in the art and described, for example in U.S. Pat. Nos. 6,391,297B1; 6,777,231B1; Burris et al. (1999) Mol Endocrinol 13:410-7; Erickson et al. (2002) Biochem Biophys Res Commun. Jan. 18, 2002; 290(2):763-9; Gronthos et al. (2001) Journal of Cellular Physiology, 189:54-63; Halvorsen et al. (2001) Metabolism 50:407-413; Halvorsen et al. (2001) Tissue Eng. 7(6):729-41; Harp et al. (2001) Biochem Biophys Res Commun 281:907-912; Saladin et al. (1999) Cell Growth & Diff 10:43-48; Sen et al. (2001) Journal of Cellular Biochemistry 81:312-319; Zhou et al. (1999) Biotechnol. Techniques 13: 513-517; Erickson et al. (2002) Biochem Biophys Res Commun. Jan. 18, 2002; 290(2):763-9; Gronthos et al. (2001) Journal of Cellular Physiology, 189:54-63; Halvorsen et al. (2001) Metabolism 50:407-413; Halvorsen et al. (2001) Tissue Eng. Dec. 7, 2001; (6):729-41; Harp et al. (2001) Biochem Biophys Res Commun 281:907-912; Saladin et al. (1999) Cell Growth & Diff 10:43-48; Sen et al. (2001) Journal of Cellular Biochemistry 81:312-319; Zhou et al. (1999) Biotechnol. Techniques 13:513-517; Zuk et al. (2001) Tissue Eng. 7: 211-228.

SVFC's can be obtained from any animal (alive or dead) so long as adipose stromal cells within the animal are viable. Suitable tissue sources of SVFC's include, but are not limited to any fat-containing tissue, e.g., brown or white adipose tissue such as subcutaneous white adipose tissue. Typically, human adipose tissue is obtained from a living donor using surgical excision or suction lumpectomy. In some embodiments, the fat tissue is obtained from a pre-selected region on the subject, i.e., inguinal, retroperitoneal and gonadal, or any combination thereof.

The separated ADSC-containing tissue optionally can be washed with any suitable physiologically-compatible solution, such as phosphate buffer saline (PBS) or normal saline. Using the exemplified methods, washing is not required, i.e., we simply can place sonication rod into adipose sample or lipoaspirate and turn on the sonication device thereby processing the sample with the ultrasonic cavitation device. After treatment three layers form after settlement of the dissociated adipose tissue. The top layer is a free lipid (fat) layer. The middle layer includes the lattice and adipocyte aggregates. The bottom layer or cell pellet which is produced after the treated composition is allowed to settle or is centrifuged and contains the stromal vascular fraction cells (SVFC's).

The cellular fraction of the bottom layer may be infused into a subject or may be further concentrated into a pellet by any suitable method, e.g., centrifugation, and retained for further processing. If desired the stromal vascular fraction (SVF) may be resuspended and can be further washed in physiologically compatible buffer, centrifuged, and resuspended one or more successive times to achieve greater purity. The cells of the washed and resuspended pellet may also be plated.

Morphological, biochemical or molecular-based methods may be used to identify or isolate the cells in the stromal vascular fraction (SVF). In one aspect, SVFC's are isolated based on cell size and granularity since SVFC's are small and agranular. Alternatively, because stem cells tend to have longer telomeres than differentiated cells, SVFC's can be isolated by assaying the length of the telomere or by assaying for telomerase activity.

Alternatively, SVFC's can be separated from the other cells of the pellet immunohistochemically by selecting for ADSC-specific cell markers using suitable materials and methods, e.g., panning, using magnetic beads, or affinity chromatography. Suitable markers include any of the markers disclosed in this application or any combination thereof.

In one embodiment, the stem cells may be cultured without differentiation using standard cell culture media, referred to herein as control medium. (e.g., DMEM, typically supplemented with 5-15% serum (e.g., fetal bovine serum, horse serum, etc.). The stem cells can be passaged at least five times or even more than twenty times in this or similar medium without differentiating to obtain a substantially homogeneous population of SVFC's. The SVFC's can be identified by phenotypic identification. To phenotypically separate the SVFC's, the cells are plated at any suitable density which may be anywhere from between about 100 cells/cm2 to about 100,000 cells/cm2 (such as about 500 cells/cm2 to about 50,000 cells/cm2, or, more particularly, between about 1,000 cells/cm2 to about 20,000 cells/cm2).

After passaging for several days, SVFC's initially plated at lower densities (at less than 500 cells/cm2, or alternatively, less than about 300 cells/cm2 or alternatively, at less than 100 cells/cm2) can be used to obtain a clonal population of SVFC's by any suitable method such as by physically picking and seeding cells into separate plates (such as the well of a multi-well plate). Alternatively, the stem cells can be subcloned into a multi-well plate at a statistical ratio for facilitating placing a single cell into each well (e.g., from about 0.1 to about 1 cell/well or even about 0.25 to about 0.5 cells/well, such as 0.5 cells/well). Cloning can be facilitated by the use of cloning rings. See MacFarland, D. C. (2000) Methods in Cell Sci. 22:63-66. Alternatively, where an irradiation source is available, clones can be obtained by permitting the cells to grow into a monolayer and then shielding one and irradiating the rest of the cells within the monolayer. The surviving cell then will grow into a clonal population. Alternatively, plated cells can be diluted to a density of 10 cells/ml and plated on Nunclon 96-well plates (Nalge Nunc International). Only wells that contain a single cell at the outset of the culture period are assayed for colony formation. Clones are detectable by microscopy after 4 to 5 days.

An exemplary culture condition for cloning stem cells comprises about 213 F12 medium+20% serum (preferably fetal bovine serum) and about 113 standard medium that has been conditioned with stromal cells or 15% FBS, 1% antibiotic/antimycotic in F-12/DMEM [1:1]) (e.g., cells from the stromal vascular fraction of liposuction aspirate, the relative proportions can be determined volumetrically).

Applications of the Inventive Stromal or Mesenchymal Adipose Tissue Derived Fractions and Cells Contained Therein The stromal and mesenchymal vascular fractions and cells derived therefrom which are produced according to the invention have numerous applications including use in reconstructive and aesthetic plastic surgery, and therapies, especially indications wherein stem cells and differentiated cells derived therefrom have clinical or aesthetic efficacy. Because the subject methods avoid the use of collagenase or other substances which are undesired for infusion in humans the subject vascular fractions and cells contained therein may be directly infused into patients in need thereof. The patient may be autologous, i.e., derived from the same donor or the cells may be infused into a compatible donor. Methods of HLA tissue matching cells for infusion into patients are well known in the art.

For example the vascular cell fractions may be administered alone or in combination with tissue fillers (such as Juvederm) or scaffolds or matrices used to promote tissue regeneration or reconstruction, e.g., breast or other cancer reconstructive surgeries, foot surgery, breast augmentation, penile implants, facial fillers, joint or cartilage surgery, neck surgery, and the like.

In addition, the subject vascular cell fractions and stem cells derived therefrom may be used in cosmetic compositions used for topical application to the skin to effect rejuvenation and promote radiance, reduce wrinkling, and the like.

Alternatively the mesenchymal or stromal vascular fraction produced according to the invention may be purified into desired cell types, e.g., a pure population of mesenchymal or stromal stem cells and these cells propagated in vitro using cell culture methods well known to those skilled in the art. As discussed herein those skilled in the art conventionally separate stem cells from other cells by FACS and other cell sorting methods based on the expression of characteristic markers.

The resultant purified stem cells may be injected into desired organs to effect tissue repair, e.g. into heart muscle to effect repair of the heart muscle, after a heart attack, into brain or spinal fluid to effect neural or nerve regeneration, such as Parkinson's or Alzheimer's patients, into the bone or cartilage of individuals in need thereof such as individuals suffering from age, exertion, or disease related bone or cartilage loss.

These purified stem cells may alternatively be cultured under conditions that give rise to desired cell lineages. For example mesenchymal and stromal stem cells comprised in the subject fraction s may be differentiated into desired cell types including fibroblasts, neural cells, hematopoietic cells, myocytes, chondrocytes, and other cell types. In addition these cell types, e.g., fibroblast populations may be seeded on a scaffold, which may be used in wound healing.

In another embodiment, the present invention may include an automated system for separating and concentrating clinically safe regenerative cells from adipose tissue that are suitable for re-infusion into a subject. A system for separating and concentrating cells from adipose tissue in accordance with the invention may include one or more of a collection chamber, a processing chamber, a waste chamber, an output chamber and a sample chamber. The various chambers are coupled together via one or more conduits such that fluids containing biological material may pass from one chamber to another in a closed, or functionally closed, sterile fluid/tissue pathway which minimizes exposure of tissue, cells, biologic and non-biologic materials with contaminants. In certain embodiments, the waste chamber, the output chamber and the sample chamber are optional. In a preferred embodiment, the system contains clinically irrelevant quantities of endotoxin. The system also includes a plurality of filters. The filters are effective to separate the stem cells and/or progenitor cells from, among other things, collagen, free lipids, adipocyte, that may be present in the solution after ultrasonication cavitation of the adipose tissue sample. In one embodiment, the a filter assembly may include a hollow fiber filtration device. In another embodiment, a filter assembly includes a percolative filtration device, which may or may not be used with a sedimentation process. In another embodiment, the filter assembly may comprise a centrifugation device, which may or may not be used with an elutriation device and process. In yet another embodiment, the system may comprise a combination of these filtering devices. The filtration functions can be two-fold, with some filters removing things from the final concentration such as collagen, free lipid, free adipocytes, and with other filters being used to concentrate the final product.

In other embodiments, one or more components of the system are automated and include an internal processing device and associated software programs which control many of the processing functions. Components of the system may be disposable, such that portions of the system can be disposed of after a single use. Such a system also comprises a re-usable component which includes the processing device (computer and associated software programs) and other components such as motors, pumps, etc.

In one embodiment, a method of treating a patient includes steps of: a) providing a tissue removal system; b) removing adipose tissue from a patient using the tissue removal system, the adipose tissue having a concentration of stem cells; c) processing at least a part of the adipose tissue by use of ultrasonic sonication for a time sufficient to explode all or most of the fat cells and release the mesenchymal and stromal vascular cells into a suitable fluid medium, e.g. phosphate buffered saline solution, d) allowing the treated solution to settle such that the fat rises to the top of the solution and the fat is removed in order to obtain a concentrated mesenchymal or stromal vascular fraction containing regenerative cells other than the concentration of regenerative cells of the adipose tissue before processing, wherein the processing occurs within a sterile, closed or functionally closed system; and e) administering the concentrated regenerative cells to a patient, to thereby treat the patient.

In certain embodiments, the active cell population is administered directly into the patient. In other words, the active cell population (e.g., the stem cells and/or endothelial precursor cells contained in the mesenchymal or stromal vascular fraction) are administered to the patient without being removed from the system or exposed to the external environment of the system before being administered to the patient. Providing a closed system reduces the possibility of contamination of the material being administered to the patient. Thus, processing the adipose tissue in a closed system provides advantages because the active cell population is more likely to be sterile. In such an embodiment, the only time the stem cells and/or endothelial precursor cells are exposed to the external environment, or removed from the system, is when the cells are being withdrawn into an application device and being administered to the patient. In one embodiment, the application device can also be part of the closed system. Thus, the cells used in these embodiments are not processed for culturing, or cryopreserved.

The active cells that have been concentrated, as described above, may be administered to a patient without further processing, or may be administered to a patient after being mixed with other tissues or cells. In certain embodiments, the concentrated active cells (e.g., stem cells or endothelial precursor cells) are mixed with one or more units of adipose tissue that has not been similarly processed. Thus, by practicing the methods of the invention, a composition comprising adipose tissue with an enhanced concentration of active cells may be administered to the patient. The volumes of the various units of adipose tissue may be different. For example, one volume may be at least 25% greater than the volume of another unit of adipose tissue. Furthermore, one volume may be at least 50%, such as at least 100%, and even 150% or more greater than the volume of another unit of adipose tissue. In addition, the desired composition may be obtained by mixing a first unit of adipose tissue with the concentrated active cell population, which may be a cell pellet containing the active cells, with one or more other units of adipose tissue. In certain embodiments, these other units will not have an increased concentration of stem cells, or in other words, will have an active cell concentration less than that contained in the first unit of adipose tissue. In other embodiments, one of the units is cryopreserved material that contains, for example, an increased concentration of active cells.

In other embodiments, at least a portion of the active cell population is stored for later implantation/infusion. The population may be divided into more than one aliquot or unit such that part of the population of stem cells and/or endothelial precursor cells is retained for later application while part is applied immediately to the patient. Moderate to long-term storage of all or part of the cells in a cell bank is also within the scope of this invention. In such an embodiment, the cells may be mixed with one or more units of fresh or preserved adipose tissue to provide a composition containing the stem cells at a higher concentration than a unit of adipose tissue prior to processing.

At the end of processing, the concentrated cells may be loaded into a delivery device, such as a syringe, for placement into the recipient by either subcutaneous, intravenous, intramuscular, or intraperitoneal techniques. In other words, cells may be placed into the patient by any means known to persons of ordinary skill in the art, for example, they may be injected into blood vessels for systemic or local delivery, into tissue (e.g., cardiac muscle, or skeletal muscle), into the dermis (subcutaneous), into tissue space (e.g., pericardium or peritoneum), or into tissues (e.g., periurethral emplacement), or other location. Preferred embodiments include placement by needle or catheter, or by direct surgical implantation in association with additives such as a preformed matrix.

The active cell population may be applied alone or in combination with other cells, tissue, tissue fragments, demineralized bone, growth factors such as insulin or drugs such as members of the thiaglitazone family, biologically active or inert compounds, resorbable plastic scaffolds, or other additive intended to enhance the delivery, efficacy, tolerability, or function of the population. The cell population may also be modified by insertion of DNA or by placement in cell culture in such a way as to change, enhance, or supplement the function of the cells for derivation of a cosmetic, structural, or therapeutic purpose. For example, gene transfer techniques for stem cells are known by persons of ordinary skill in the art, as disclosed in Mosca, J. D., J. K. Hendricks, et al. (2000). "Mesenchymal stem cells as vehicles for gene delivery." Clin Orthop (379 Suppl): S71-90, and may include viral transfection techniques, and more specifically, adeno-associated virus gene transfer techniques, as disclosed in Walther, W. and U. Stein (2000). "Viral vectors for gene transfer: a review of their use in the treatment of human diseases." Drugs 60(2): 249-71, and Athanasopoulos, T., S. Fabb, et al. (2000). "Gene therapy vectors based on adeno-associated virus: characteristics and applications to acquired and inherited diseases (review)." Int J Mol Med 6(4): 363-75. Non-viral based techniques may also be performed as disclosed in Muramatsu, T., A. Nakamura, et al. (1998). "In vivo electroporation: a powerful and convenient means of nonviral gene transfer to tissues of living animals (Review)." Int J Mol Med 1(1): 55-62.

In one aspect, the cells could be mixed with unprocessed fragments of adipose tissue and placed back into the recipient using a very large gauge needle or liposuction cannula. Transfer of autologous fat without supplementation with processed cells is a common procedure in plastic and reconstructive surgery. However, results can be unpredictable as the transferred material tends to rapidly reabsorb resulting in an unstable graft. Adipose tissue-derived cells of the invention that are, for example, substantially depleted of mature adipocytes may provide an environment that supports prolonged survival and function of the graft.

In another aspect, the cell population could be placed into the recipient and surrounded by a resorbable plastic sheath such as that manufactured by MacroPore Biosurgery, Inc. (U.S. Pat. Nos. 6,269,716 and 5,919,234). In this setting the sheath would prevent prolapse of muscle and other soft tissue into the area of a bone fracture thereby allowing the emplaced processed adipose tissue-derived cells to promote repair of the fracture. In this aspect, the beneficial effect might be enhanced by supplementation with additional components such as pro-osteogenic protein growth factors or biological or artificial scaffolds.

In another aspect, the cells could be combined with a gene encoding a pro-osteogenic growth factor which would allow cells to act as their own source of growth factor during bone healing or fusion. Addition of the gene could be by any technology known in the art including but not limited to adenoviral transduction, "gene guns," liposome-mediated transduction, and retrovirus or Lentivirus-mediated transduction.

Particularly when the cells and/or tissue containing the cells are administered to a patient other than the patient from which the cells and/or tissue were obtained, one or more immunosuppressive agents may be administered to the patient receiving the cells and/or tissue to reduce, and preferably prevent, rejection of the transplant. Examples of immunosuppressive agents suitable with the methods disclosed herein include agents that inhibit T-cell/B-cell costimulation pathways, such as agents that interfere with the coupling of T-cells and B-cells via the CTLA4 and B7 pathways, as disclosed in U.S. patent Pub. No. 20020182211. Other examples include cyclosporin, myophenylate mofetil, rapamicin, and anti-thymocyte globulin.

In certain embodiments of the invention, the cells are administered to a patient with one or more cellular differentiation agents, such as cytokines and growth factors.

Examples of various cell differentiation agents are disclosed in Gimble, J. M., C. Morgan, et al. (1995). "Bone morphogenetic proteins inhibit adipocyte differentiation by bone marrow stromal cells." J Cell Biochem 58(3): 393-402; Lennon, D. P., S. E. Haynesworth, et al. (1995). "A chemically defined medium supports in vitro proliferation and maintains the osteochondral potential of rat marrow-derived mesenchymal stem cells." Exp Cell Res 219(1): 211-22; Majumdar, M. K., M. A. Thiede, et al. (1998). "Phenotypic and functional comparison of cultures of marrow-derived mesenchymal stem cells (MSCs) and stromal cells." J Cell Physiol 176(1): 57-66; Caplan, A. I. and V. M. Goldberg (1999). "Principles of tissue engineered regeneration of skeletal tissues." Clin Orthop (367 Suppl): S12-6; Ohgushi, H. and A. I. Caplan (1999). "Stem cell technology and bioceramics: from cell to gene engineering." J Biomed Mater Res 48(6): 913-27; Pittenger, M. F., A. M. Mackay, et al. (1999). "Multilineage potential of adult human mesenchymal stem cells." Science 284(5411): 143-7; Caplan, A. I. and S. P. Bruder (2001). "Mesenchymal stem cells: building blocks for molecular medicine in the 21st century." Trends Mol Med 7(6): 259-64; Fukuda, K. (2001). "Development of regenerative cardiomyocytes from mesenchymal stem cells for cardiovascular tissue engineering." Artif Organs 25(3): 187-93; Worster, A. A., B. D. Brower-Toland, et al. (2001). "Chondrocytic differentiation of mesenchymal stem cells sequentially exposed to transforming growth factor-beta1 in monolayer and insulin-like growth factor-I in a three-dimensional matrix." J Orthop Res 19(4): 738-49; Zuk, P. A., M. Zhu, et al. (2001). "Multilineage cells from human adipose tissue: implications for cell-based therapies." Tissue Eng 7(2): 211-28; and Mizuno, H., P. A. Zuk, et al. (2002). "Myogenic differentiation by human processed lipoaspirate cells." Plast Reconstr Surg 109(1): 199-209; discussion 210-1.

By administering the stem cells and/or endothelial precursor cells to a patient, one can treat numerous diseases, including, and not limited to, bone-related disorders, diseases, or injuries, including slow/non-union fractures, osteoporosis (age-related or chemotherapy-induced), inherited diseases of bone (osteogenesis imperfecta); adipose related disorders or diseases; liver related diseases, disorders, or injuries, including liver failure, hepatitis B, and hepatitis C; myocardial infarctions, including heart attack or chronic heart failures; renal diseases or kidney damage; retinal diseases or damage or necrosis; wound healing (e.g., from surgery or diabetic ulcers); skeletal muscle disorders both traumatic and inherited; cartilage and joint repair both traumatic and autoimmune; lung injuries; diabetes; intestinal disorders; nervous system disorders, diseases, or injuries, such as central nervous systems disorders, diseases, or injuries, including spinal cord injuries, Parkinson's disease, Alzheimer's disease, and stroke.

The cells or composition containing may in addition further contain an additional pharmaceutical or agent, or alternatively a polynucleotide that encodes for a therapeutic agent or for an inhibiting nucleic acid. Examples of nuclear acids include, a ribozyme, an antisense oligonucleotide, a double stranded RNA, a double-stranded interfering RNA (iRNA), a triplex RNA, an RNA aptamer, and at least a portion of an antibody molecule that binds to the gene product and inhibits its activity.

The present invention contemplates any known usage of the subject adipose derived stromal or mesenchymal vascular fraction or stem and endothelial precursor cells purified or derived therefrom such as by induced differentiation. In particular the following usages of cells according to the invention as described in the patent references discussed below are contemplated.

For example U.S. Pat. No. 7,875,296 by Binette et al teaches conformable tissue implant for use in repairing or augmenting a tissue defect or injury site that may contain stem cells. The tissue implant contains a tissue carrier matrix comprising a plurality of biocompatible, bioresorbable granules and at least one tissue fragment in association with the granules.

U.S. Pat. No. 7,875,276 by Kropp teaches the use of stromal cells for repairing a damaged urinary tract tissue of a subject.

U.S. Pat. No. 7,625,581 teaches the use of stem and endothelial precursor cells in tissue scaffolds suitable for use in repair and/or regeneration of musculoskeletal tissue when implanted in a body.

U.S. Pat. No. 7,316,822 by Binette also teaches a tissue repair implant comprising: a tissue carrier matrix comprising a plurality of biocompatible, bioresorbable granules and at least one tissue fragment in association with the tissue carrier matrix, the at least one tissue fragment having an effective amount of viable cells that can migrate out of the tissue fragment and populate the tissue carrier matrix, wherein the tissue carrier matrix is in the form of an injectable suspension, and wherein an average maximum outer diameter of the granules is in a range of about 150 to about 600 um.

U.S. Pat. No. 7,299,805 by Benutti et al teaches a method of implanting stem or endothelial precursor cells into a body of a patient, said method comprising the steps of: providing a support structure, harvesting a polysaccharide-based modified biofilm from bacteria, attaching viable cells for implantation to the support structure with the polysaccharide-based modified biofilm, and connecting one portion of a blood vessel in the patient's body with a first portion of the support structure, and connecting another portion of a blood vessel in the patient's body with a second portion of the support structure.

U.S. Pat. No. 7,192,604 by Brown et al and assigned to Ethicon teaches an implantable biodegradable device containing a fibrous matrix, the fibrous matrix being constructed from fibers A and fibers B, wherein fibers A biodegrade faster than fibers B, fibers A and fibers B are present in relative amounts and are organized such that the fibrous matrix is provided with properties useful in repair and/or regeneration of mammalian tissue, and which may contain mesenchymal or stromal stem or endothelial precursor cells.

U.S. Pat. No. 7,078,230 by Wilkinson et al assigned to Artecel, Inc teaches the use of pluripotent stem cells generated from adipose tissue-derived stromal cells that have been induced to express at least one phenotypic characteristic of a neuronal, astroglial, hematopoietic progenitor, or hepatic cell and the use thereof in therapy or tissue reconstruction.

U.S. Pat. Nos. 7,033,587, 6,841,150, and 6,429,013 by Halvorsen and assigned to Artecel, Inc teach methods and compositions for directing adipose-derived stromal cells cultivated in vitro to differentiate into cells of the chondrocyte lineage. They also teach the use of the differentiated chondrocytes for the therapeutic treatment of a number of human conditions and diseases including repair of cartilage in vivo is disclosed.

U.S. Pat. No. 6,986,735 by Abraham et al and assigned to Organogenesis teaches methods of making bioremodelable graft prostheses prepared from cleaned tissue material derived from animal sources. The bioengineered graft prostheses of the invention are prepared using methods that preserve cell compatibility, strength, and bioremodelability of the processed tissue matrix. The bioengineered graft prostheses are used for implantation, repair, or use in a mammalian host. These prostheses may contain mesenchymal or stromal stem or endothelial precursor cells.

Still further, U.S. Pat. No. 6,991,787 by Greenberger teaches the use of stromal cells for use in gene therapy.

U.S. Pat. No. 7,011,328 by Barofsky teaches a method of effecting repair or replacement or supporting a section of a body tissue using tropoelastin, preferably crosslinked tropoelastin and specifically to provide a tropoelastin biomaterial suitable for use as a stent, for example, a vascular stent, or as conduit replacement, as an artery, vein or a ureter replacement. The tropoelastin biomaterial itself can also be used as a stent or conduit covering or coating or lining and may comprise mesenchymal or stromal stem or endothelial precursor cells.

U.S. Pat. No. 6,902,932 by Altman et al, assigned to Tissue Regeneration, Inc. and the Trustees of Tufts College describes provides a novel silk-fiber-based matrix having a wire-rope geometry for use in producing a ligament or tendon, particularly an anterior cruciate ligament, ex vivo for implantation into a recipient in need thereof. which may seeded with pluripotent cells that proliferate and differentiate on the matrix to form a ligament or tendon ex vivo. Also disclosed is a bioengineered ligament comprising the silk-fiber-based matrix seeded with pluripotent cells that proliferate and differentiate on the matrix to form the ligament or tendon.

U.S. Pat. No. 6,555,374 by Gimble et al, assigned to Artecel Sciences, Inc. teaches compositions for the differentiation of stromal cells from adipose tissue into hematopoietic supporting stromal cells and myocytes of both the skeletal and smooth muscle type. The cells produced by the methods are useful in providing a source of fully differentiated and functional cells for transplantation and development of tissue engineering products for the treatment of human diseases and traumatic tissue injury repair.

U.S. Pat. No. 6,287,340 by Altman et al teaches anterior cruciate ligament ex vivo produced by seeding pluripotent stem cells in a three dimensional matrix, anchoring the seeded matrix by attachment to two anchors, and culturing the cells within the matrix under conditions appropriate for cell growth and regeneration, while subjecting the matrix to one or more mechanical forces via movement of one or both of the attached anchors.

U.S. Pat. No. 6,284,284 by Naughton teaches compositions containing natural human extracellular matrices which may contain adipose derived cells for the repair of skin defects using natural human extracellular matrix by injection.

U.S. Pat. No. 6,086,863 by Ritter et al, and assigned to Polyheal Ltd. teaches therapeutic compositions of microspheres for application to wounds and/or lesions for accelerating wound healing and muscle regeneration that may comprise adipose derived pluripotent cells.

U.S. Pat. No. 6,082,364 by Balian et al, and assigned to Musculoskeletal Development Enterprises teaches the use of adipose derived pluripotent stem-like cells for systemic administration to treat osteoporosis, osteolysis, improve bone implant adherence, augment bone growth or bone repair, augment cartilage repair, and augment fat production for, e.g., breast augmentation, and the like.

U.S. Pat. Nos. 6,022,743, 5,858,721, 5,842,477 and 5,785,964, all by Naughton et al and assigned to Advanced Tissue Sciences, Inc. teach a stromal cell-based three-dimensional cell culture system which can be used to culture a variety of different cells and tissues in vitro for prolonged periods of time. They teach the use of this three-dimensional culture to form tubular tissue structures, like those of the gastrointestinal and genitourinary tracts, as well as blood vessels; tissues for hernia repair and/or tendons and ligaments; etc.

U.S. Pat. No. 5,902,741 by Purchio et al relates to a method of stimulating the proliferation and appropriate cell maturation of a variety of different cells and tissues in three-dimensional cultures in vitro using TGF-beta. in a culture medium containing stromal cells, including, but not limited to, chondrocytes, chondrocyte-progenitors, fibroblasts, fibroblast-like cells inoculated and grown on a three-dimensional framework in the presence of TGF-.beta. This three-dimensional system, allows for the proliferating cells mature and segregate properly to form components of adult tissues analogous to counterparts in vivo.

U.S. Pat. No. 5,478,739 by Slivka et al also describes a three-dimensional cell culture system in which stromal cells are grown on a three-dimensional matrix while cycling the cultures between metabolically favorable and metabolically unfavorable (but noncytotoxic) conditions and produces an overall structure that more closely resembles naturally occurring tissue.

U.S. Pat. No. 7,807,461 by Kang et al relates to human adipose tissue-derived multipotent adult stem cells. which can be maintained in an undifferentiated state for a long period of time by forming spheres and have high proliferation rates, as well as methods for isolating and maintaining the adult stem cells, and methods for differentiating the multipotent adult stem cells into nerve cells, fat cells, cartilage cells, osteogenic cells and insulin-releasing pancreatic beta-cells. Also, they teach the use thereof for treating osteoarthritis, osteoporosis and diabetes and for forming breast tissue, which contain the differentiated cells or the adult stem cells.

U.S. Pat. Nos. 7,771,716 7,651,684 7,585,670 7,514,075, and 7,470,537, all by Hedrick et al and assigned to Cytori Therapeutics, Inc. describe the use of regenerative cells present in adipose tissue to treat patients, including patients with musculoskeletal diseases or disorders. Methods of treating patients include processing adipose tissue to deliver a concentrated amount of regenerative cells obtained from the adipose tissue to a patient. The methods are practiced in a closed system so that the stem cells are not exposed to an external environment prior to being administered to a patient.

U.S. Pat. Nos. 7,687,059 7,501,115 and 7,473,420, all by Fraser et al and assigned to Cytori Therapeutics, Inc. teaches the use of stem and other cells present in processed lipoaspirate tissue to treat patients. Methods of treating patients including processing adipose tissue to deliver a concentrated amount of stem cells obtained from the adipose tissue to a patient are disclosed.

U.S. Pat. No. 7,531,355 by Rodriguez et al and assigned to The Regents of the University of California describes a purified or isolated population of adipose derived stem cells (SVFC'S) that can differentiate into a cell of the leiomyogenic lineage, e.g., smooth muscle or skeletal muscle or into a lineage selected from the group consisting of osteogenic, adipogenic, chondrogenic, myogenic and neurons. They describe use of an effective amount of the cells being applied to the area or tissue requiring therapy, e.g., bladder. In addition, for total tissue substitution, three dimensional scaffolds are taught using PLGA, PCL, or other materials. These scaffolds can be seeded with SVFC'S or smooth muscle differentiated SVFC'S or PCL cells and tissues reconstructed.

U.S. Pat. No. 7,452,532 by Alt and assigned to SciCoTec GmbH teaches a method for repairing tissue of a selected organ from among heart, brain, liver, pancreas, kidney, glands, and muscles in a patient's body. using stem cells that are intraluminally applied through a designated natural body vessel.

U.S. Pat. No. 7,078,232 by Konkle et al. teaches cells, methods and compositions based upon the use of adipose tissue-derived adult stem cells in the repair of articular cartilage fractures or defects and specifically treatment of articular cartilage fractures in a clinical setting.

U.S. Pat. No. 6,777,231 by Katz et al. describes adipose-derived stem cells and lattices. In one aspect, they provides a lipo-derived stem cell substantially free of adipocytes and red blood cells and clonal populations of connective tissue stem cells.

In particular the invention provides a lipo-derived stem cell substantially free of adipocytes and include treatment of use with or in lieu of tissue fillers, as a gum recession, loss of bone, including the jaw, treatment of orthopedic problems, treatment of arthritis, treatment of migraine, treatment of multiple sclerosis, treatment of autism, treatment of diabetes, treatment of wounds, treatment of ulcers, treatment of COPD, treatment of plantar fascitis, treatment of rotator cuff, and treatment of tennis elbow.

The invention is further described by the following examples.

Materials and Methods

Figure 1B:
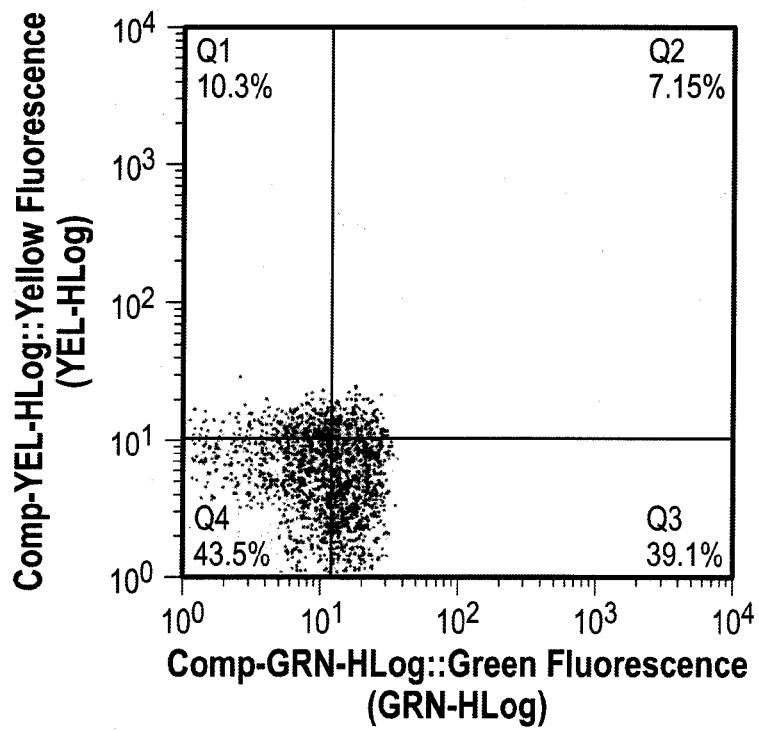
Figure 1B:
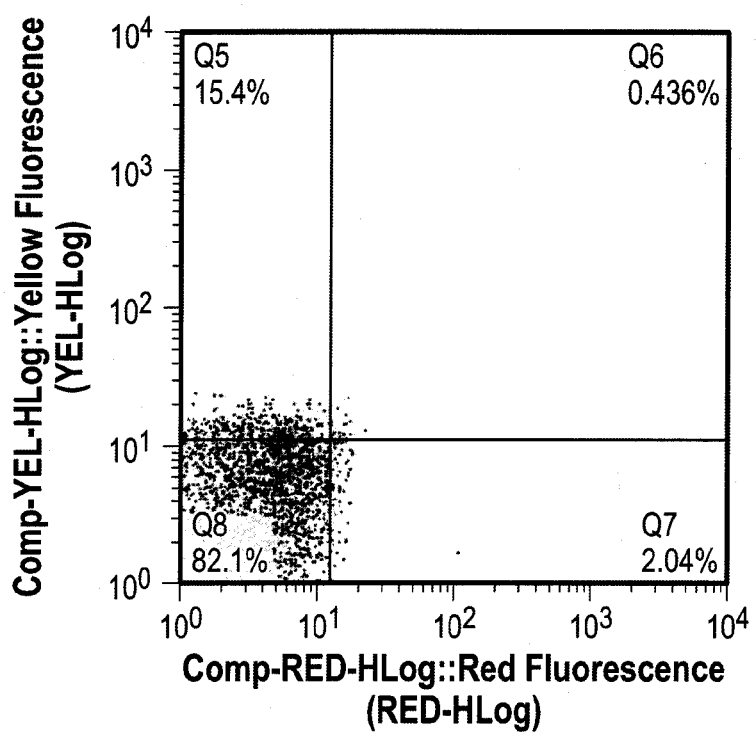
Figure 1B:
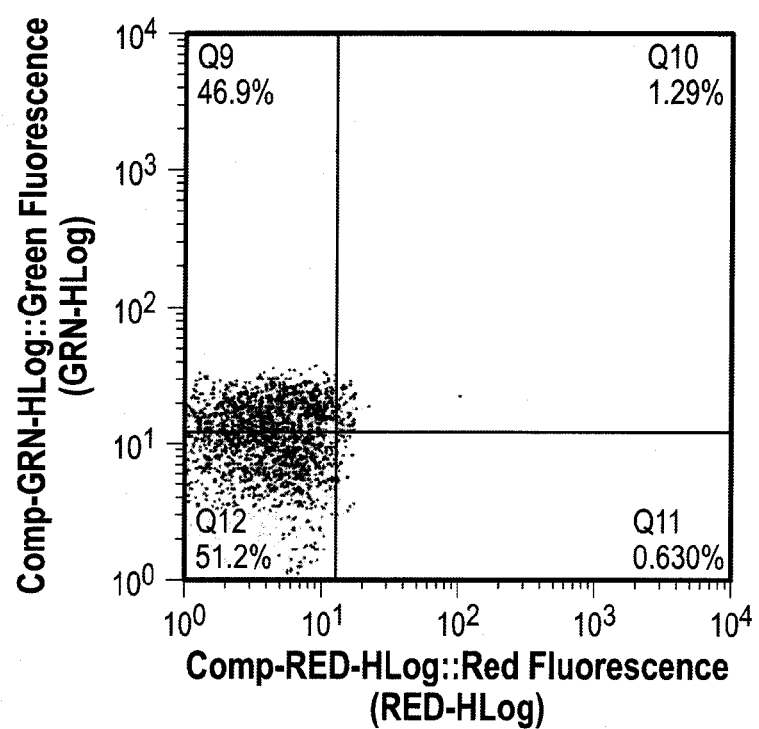
Figure 1C:
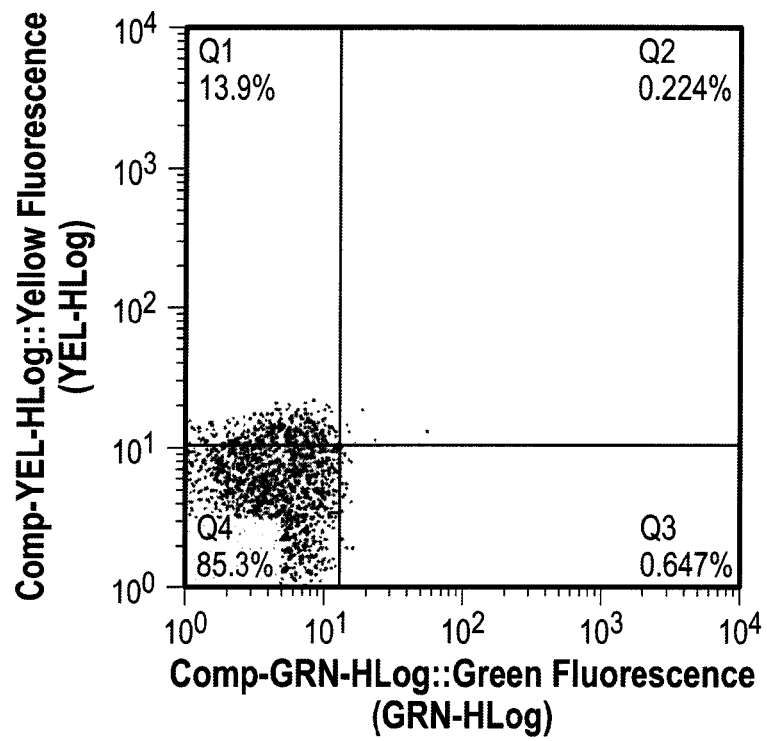
Figure 1C:
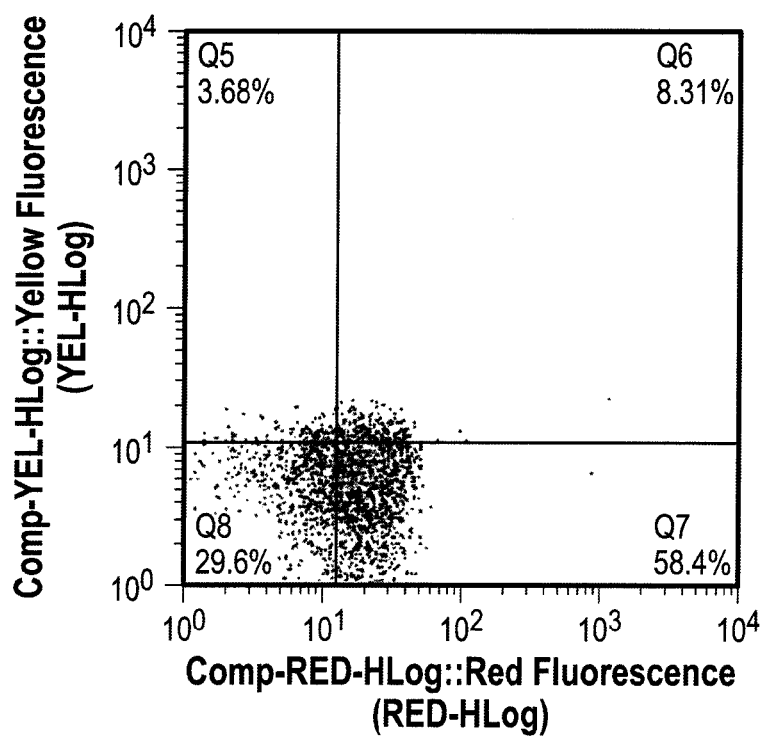
Figure 1C:
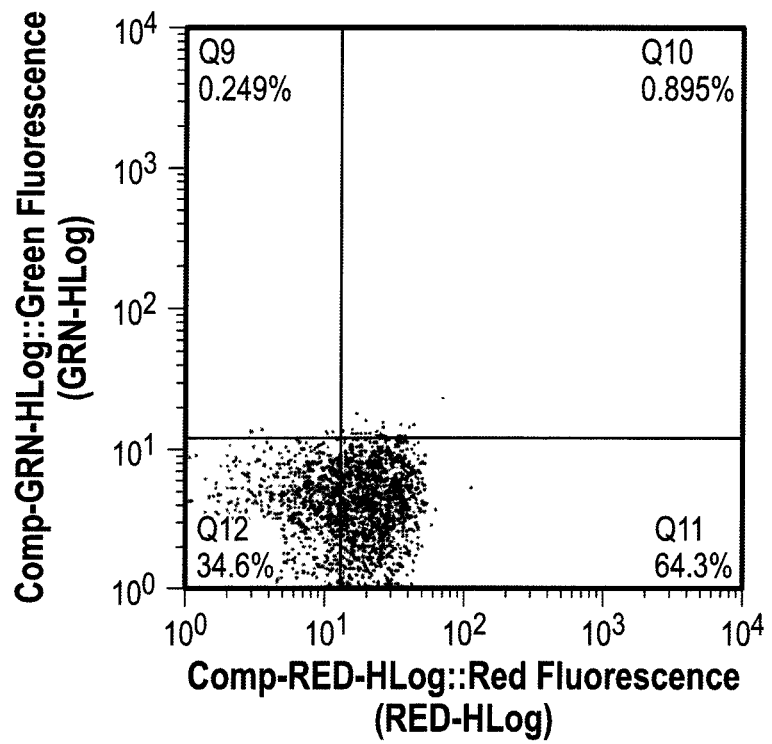
Figure 1D:
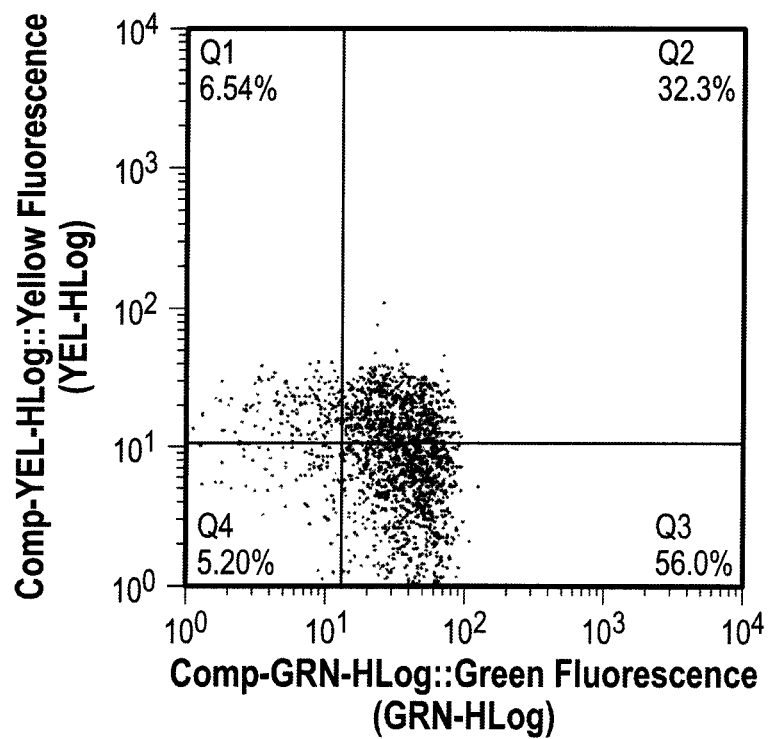
Figure 1D:
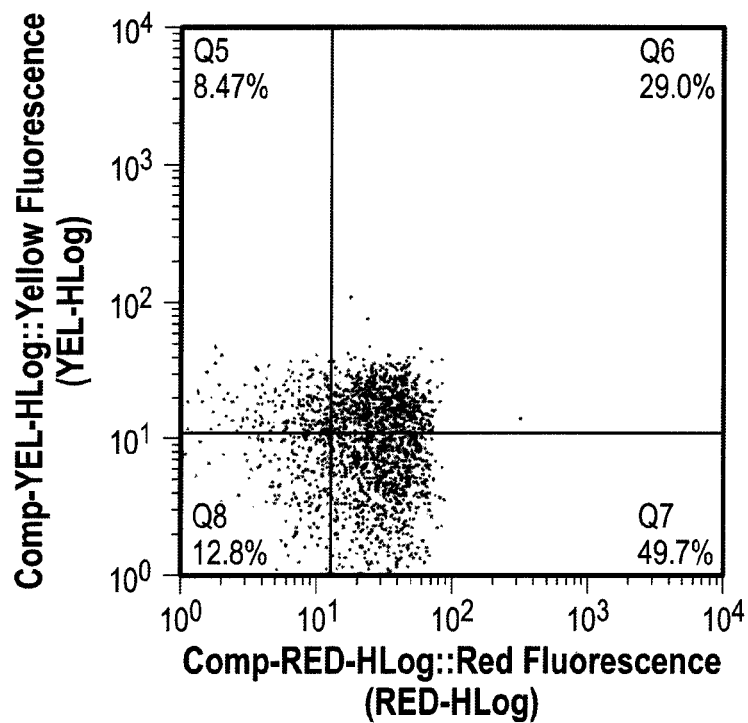
Figure 1D:
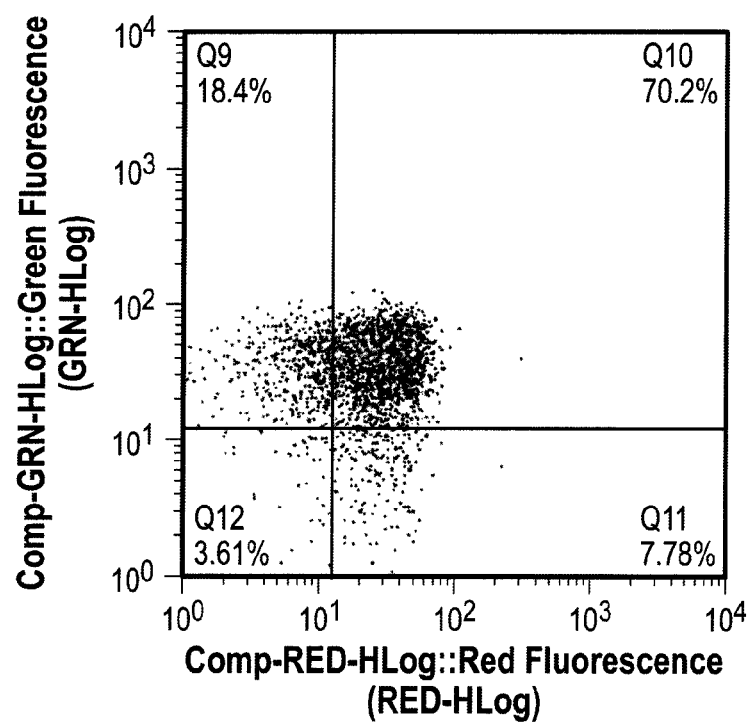
Figure 1E:
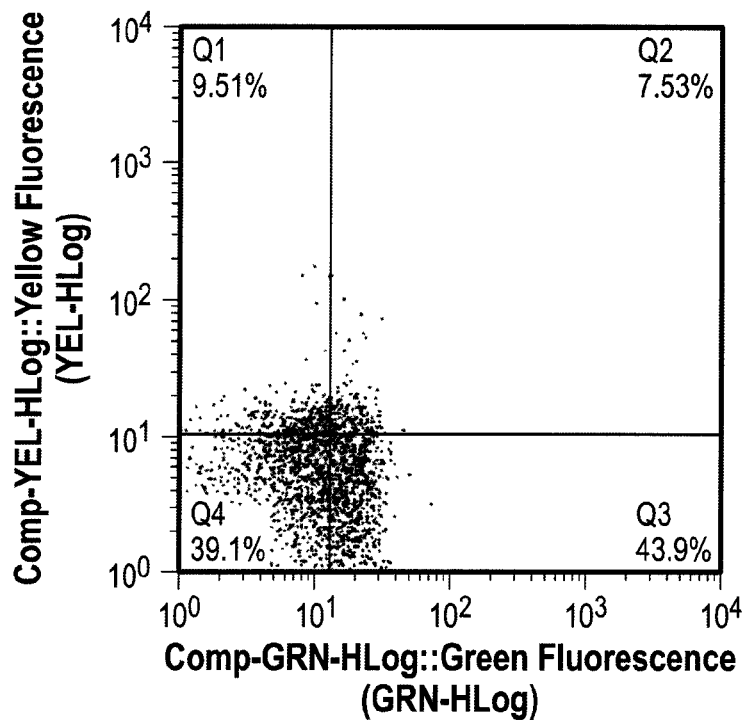
Figure 2A:
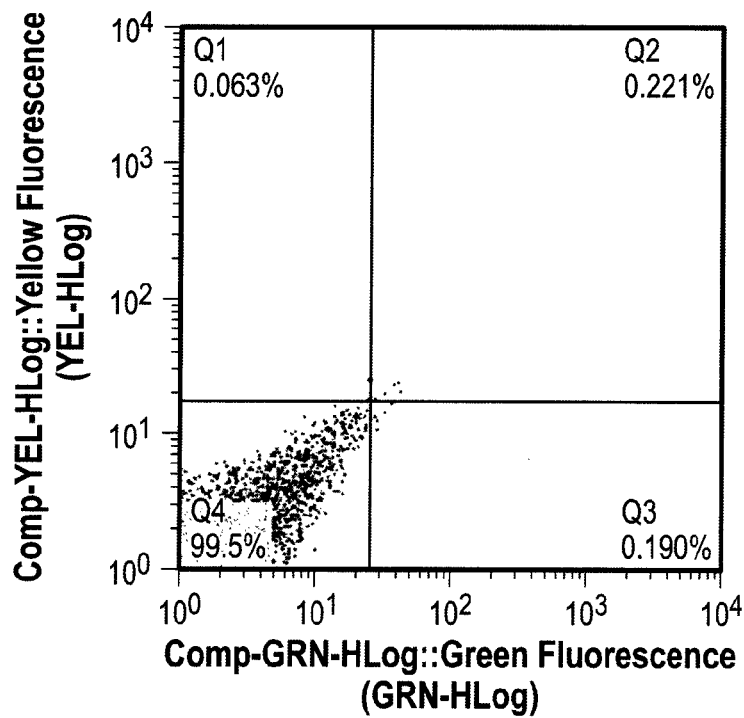
Figure 2A:
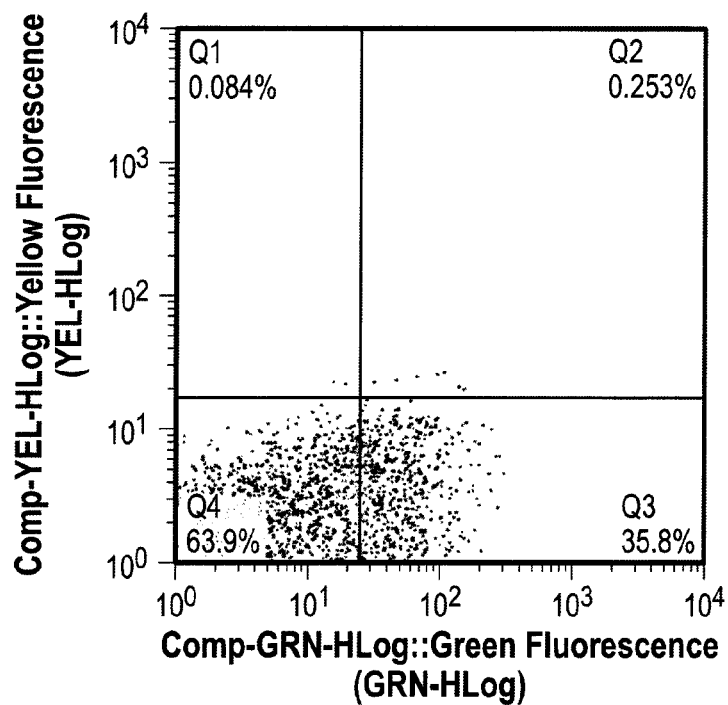
Figure 2A:
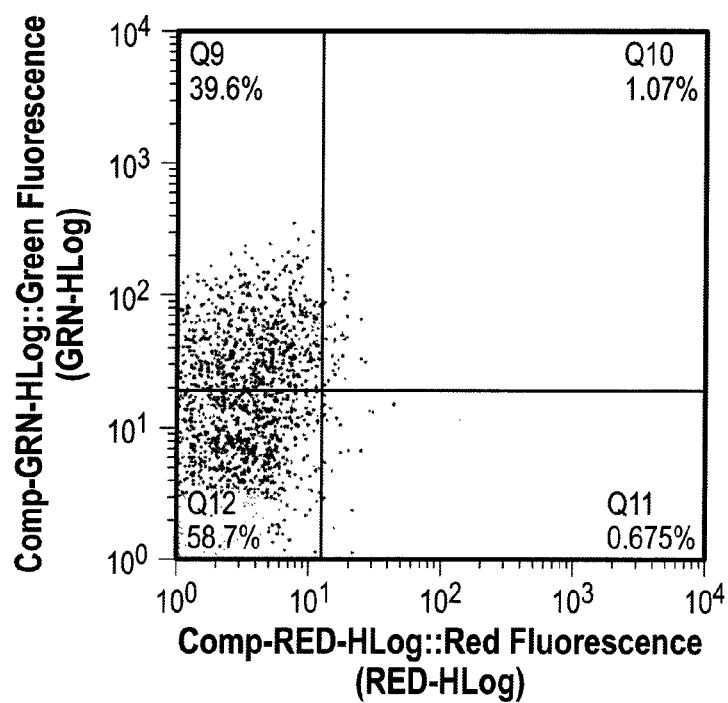
Figure 2A:
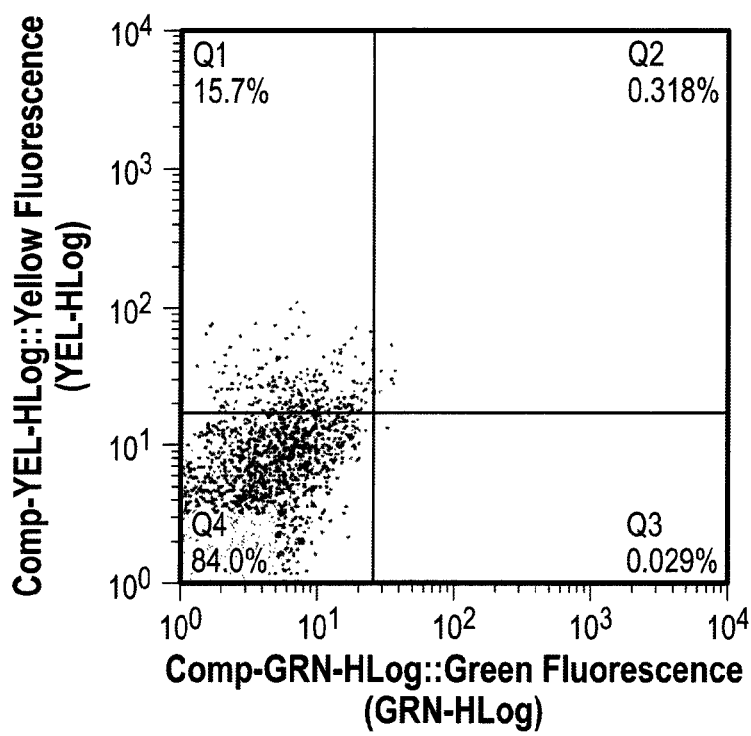
Figure 2A:
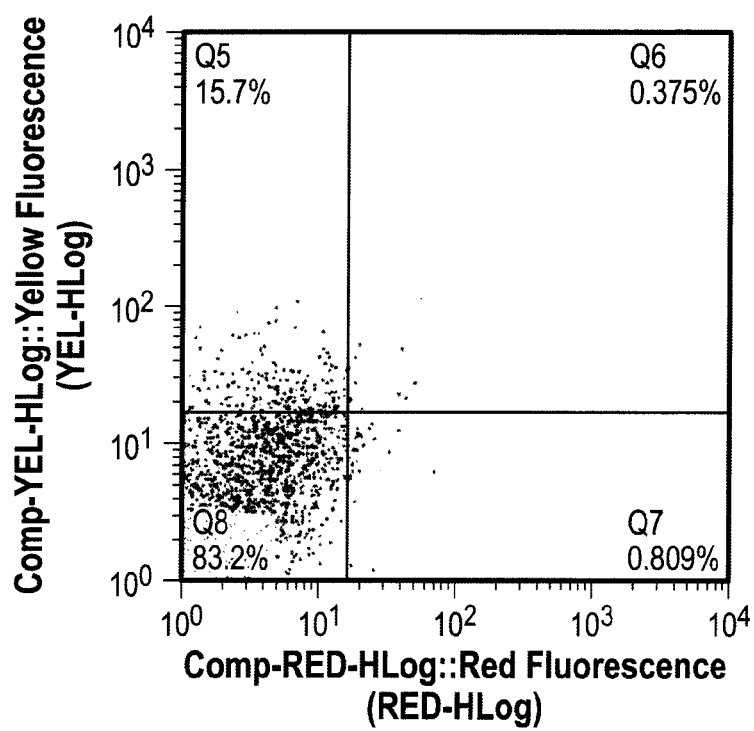
Figure 2A:
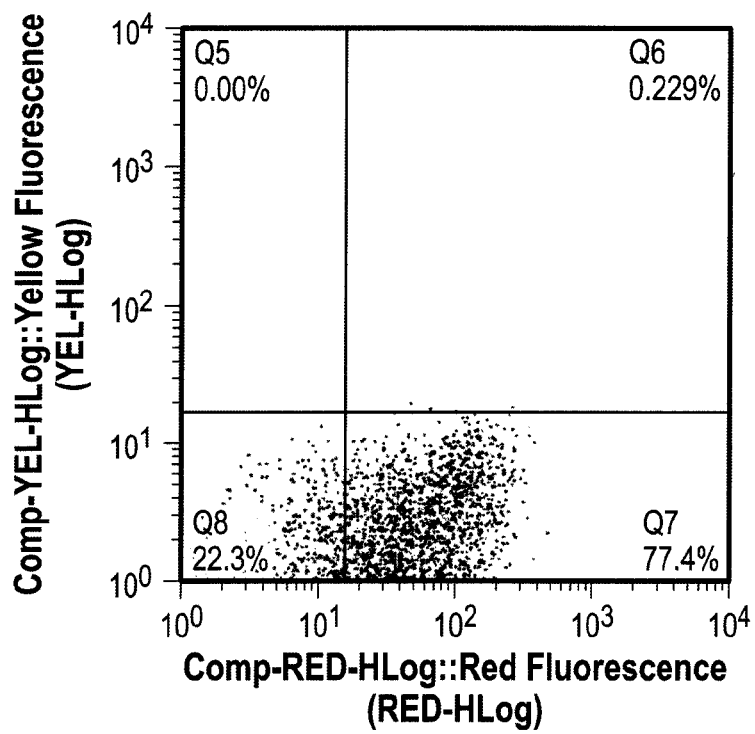
Figure 2A:
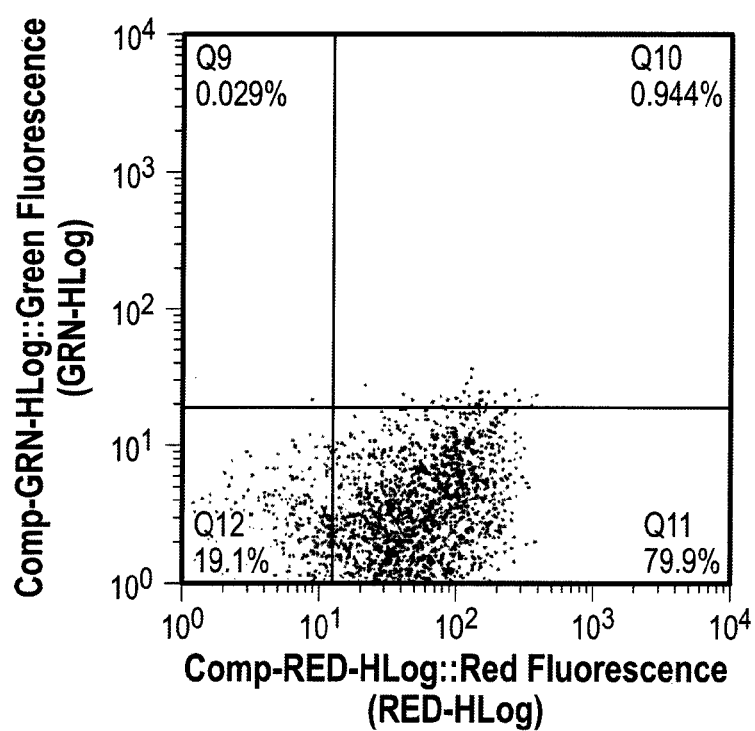
Figure 2B:
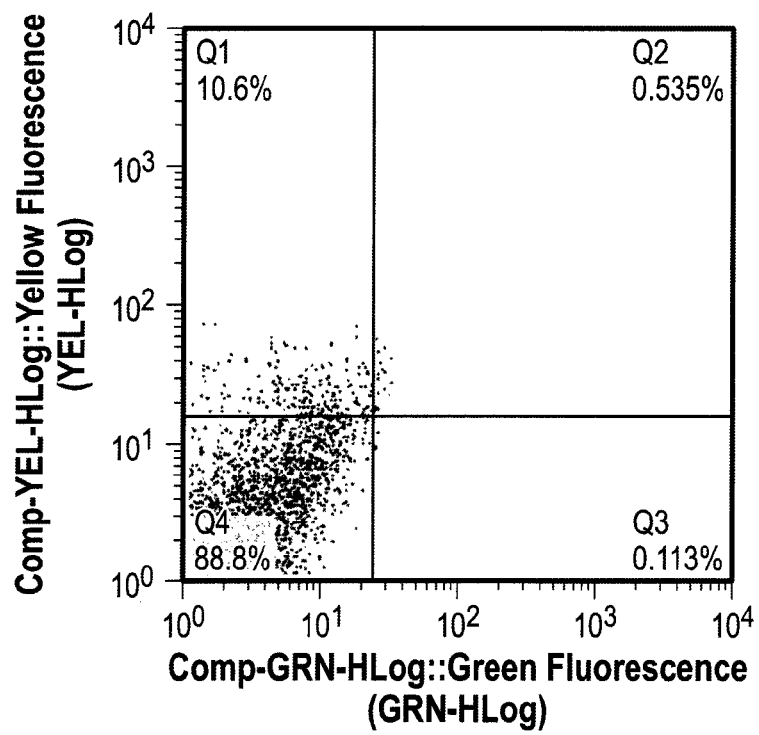
Figure 2B:
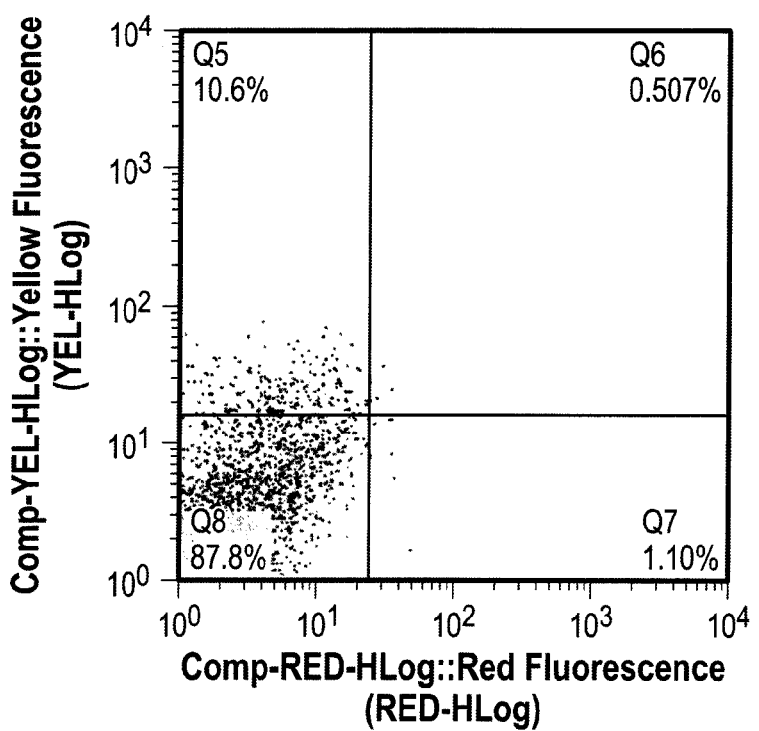
Figure 2B:
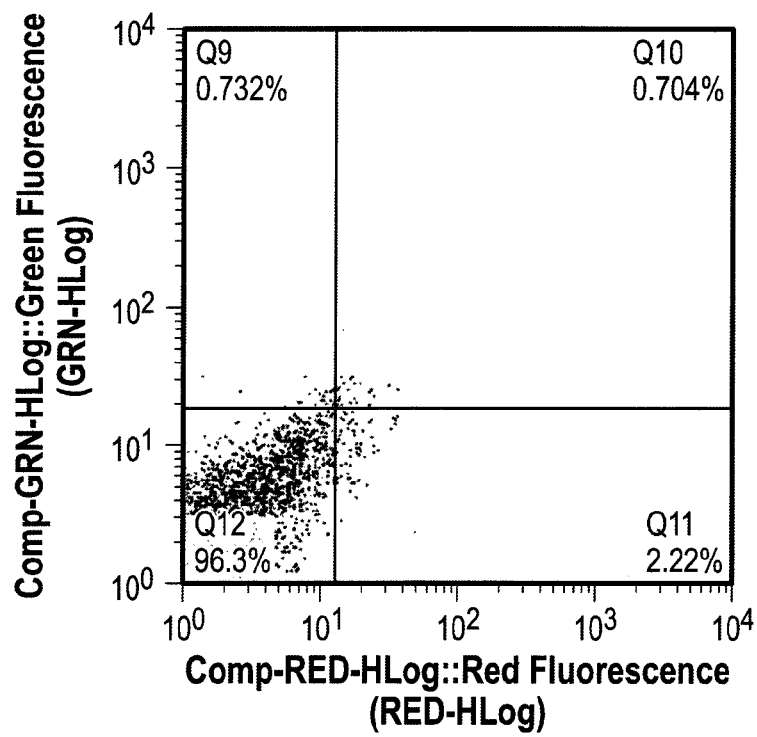
Figure 2C:
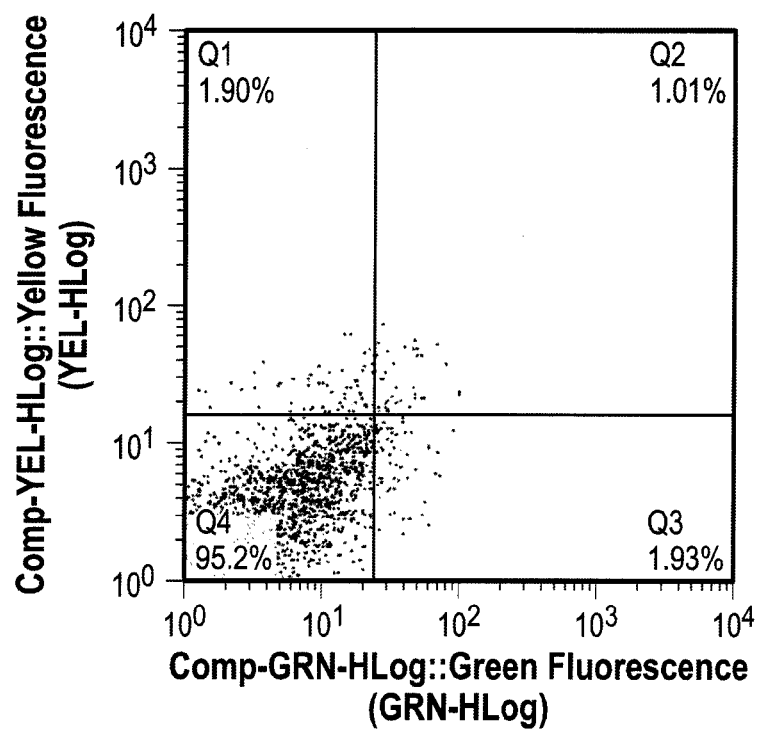
Figure 2C:
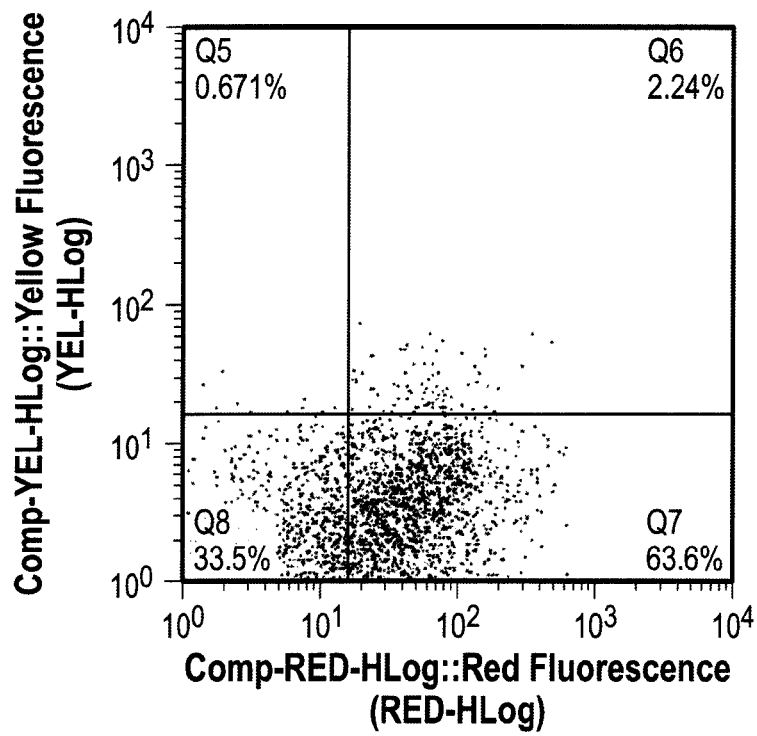
Figure 2C:
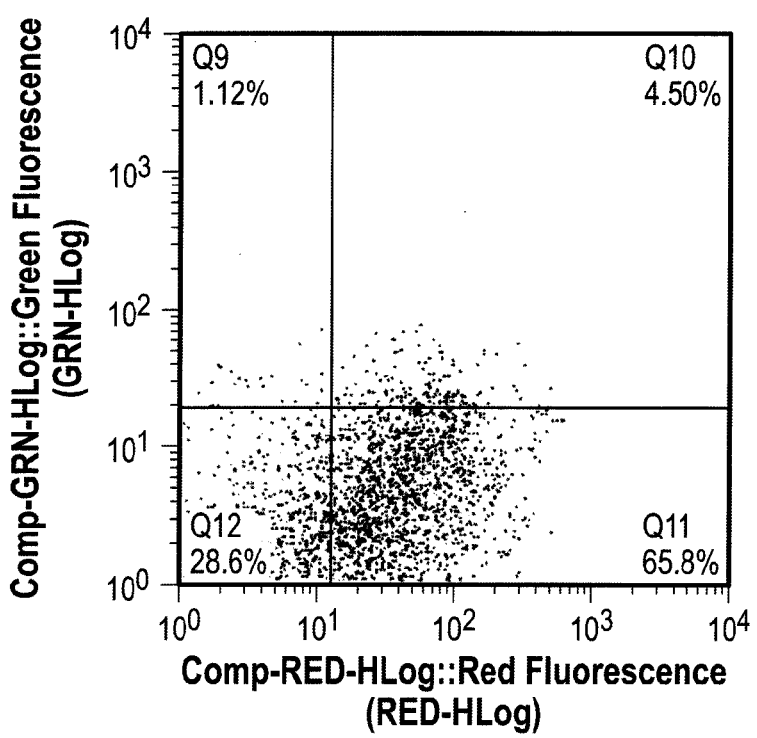
Figure 2D:
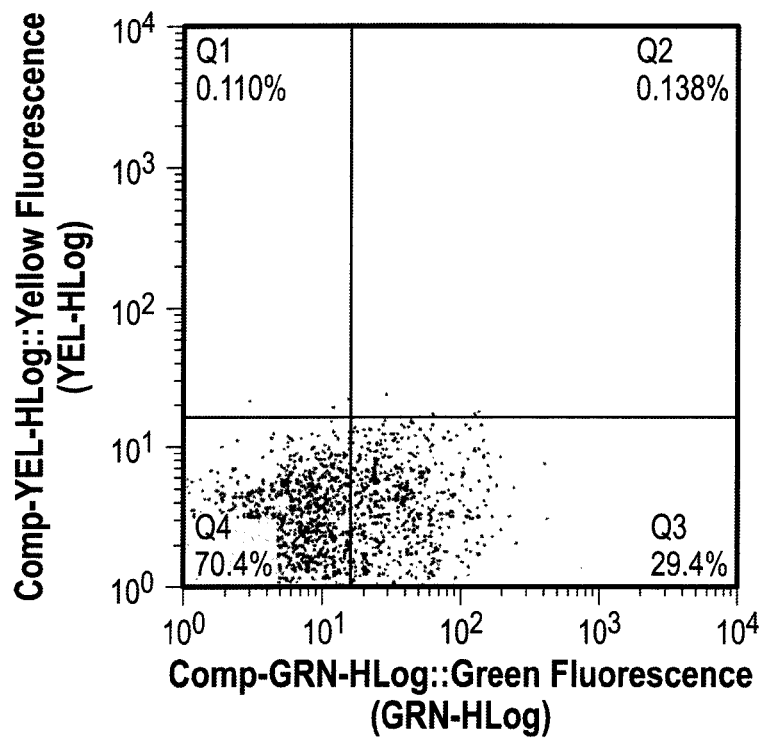
Figure 2D:
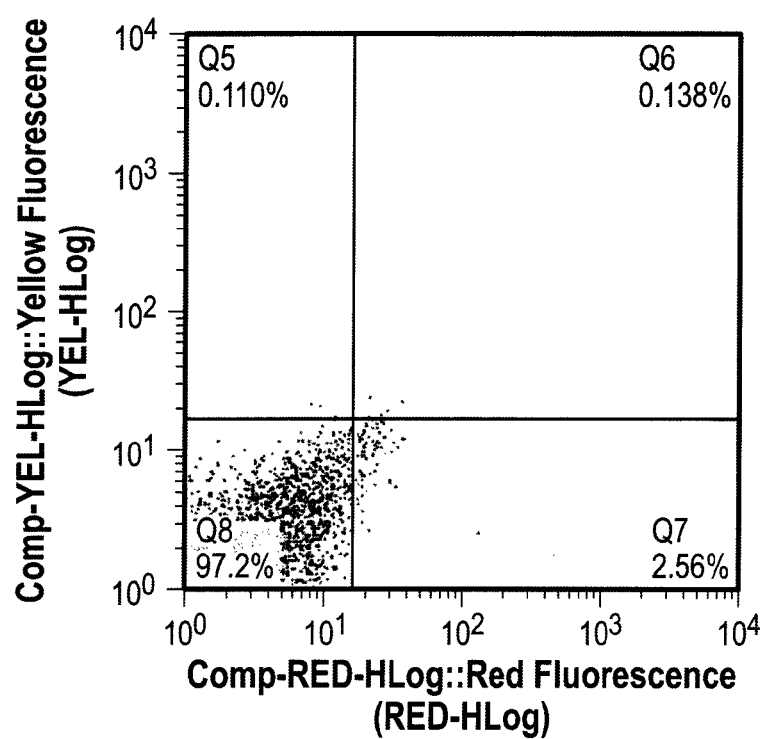
Figure 2D:
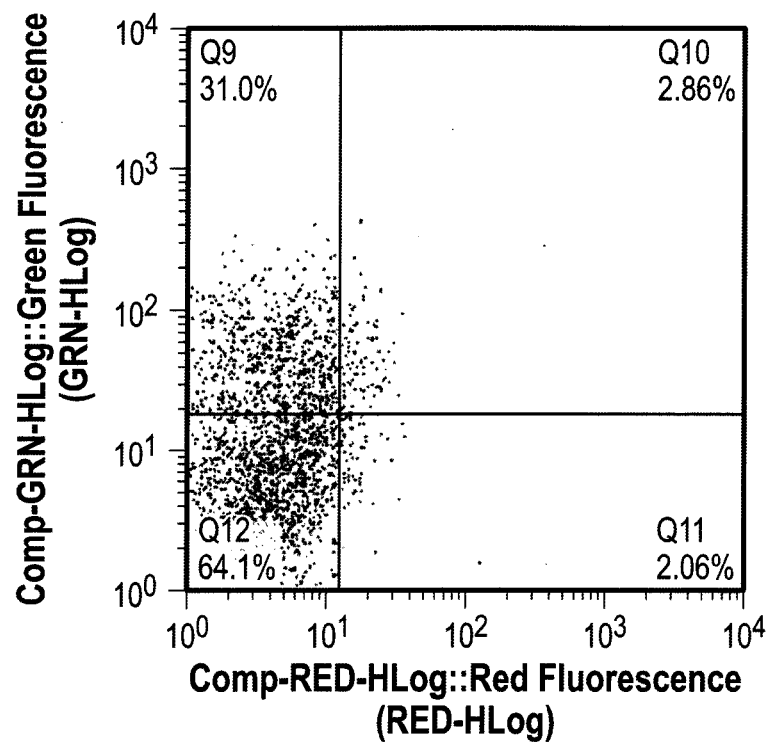
Figure 2E:
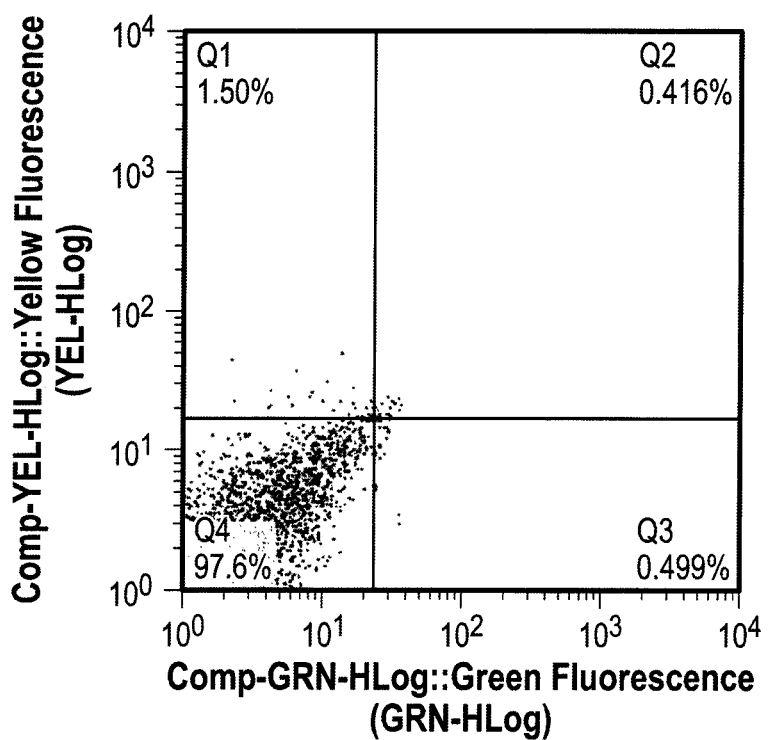
Figure 3A:
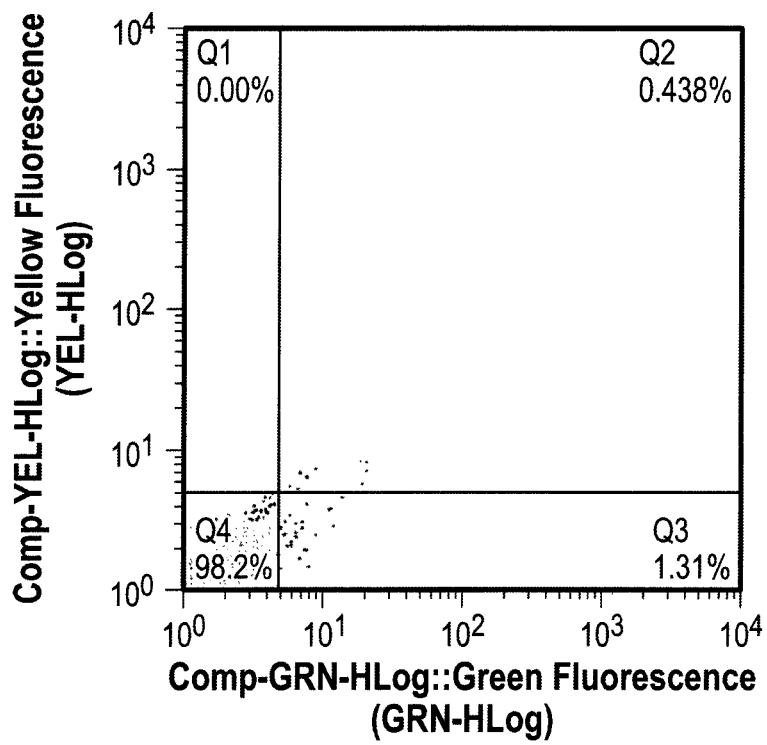
Figure 3A:
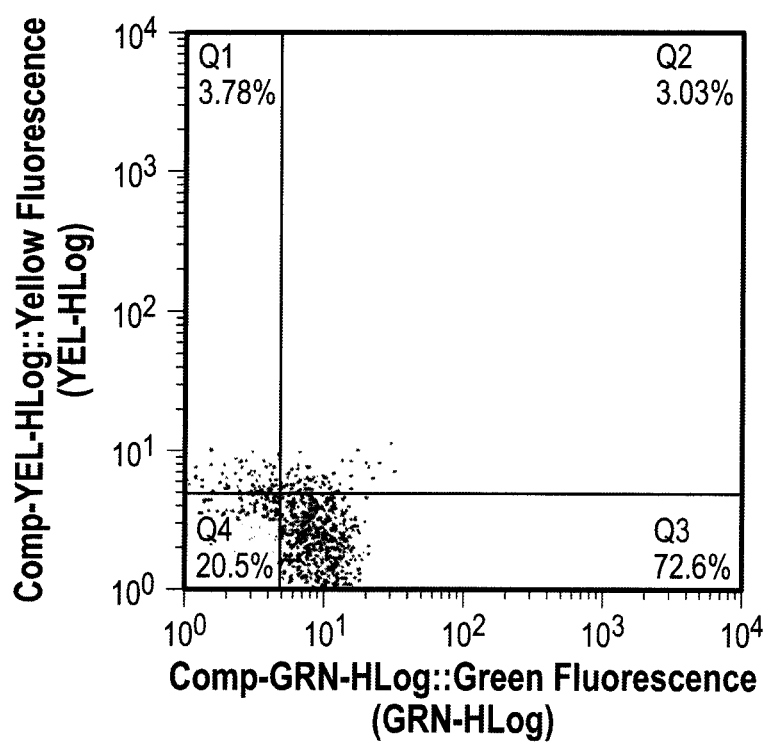
Figure 3A:
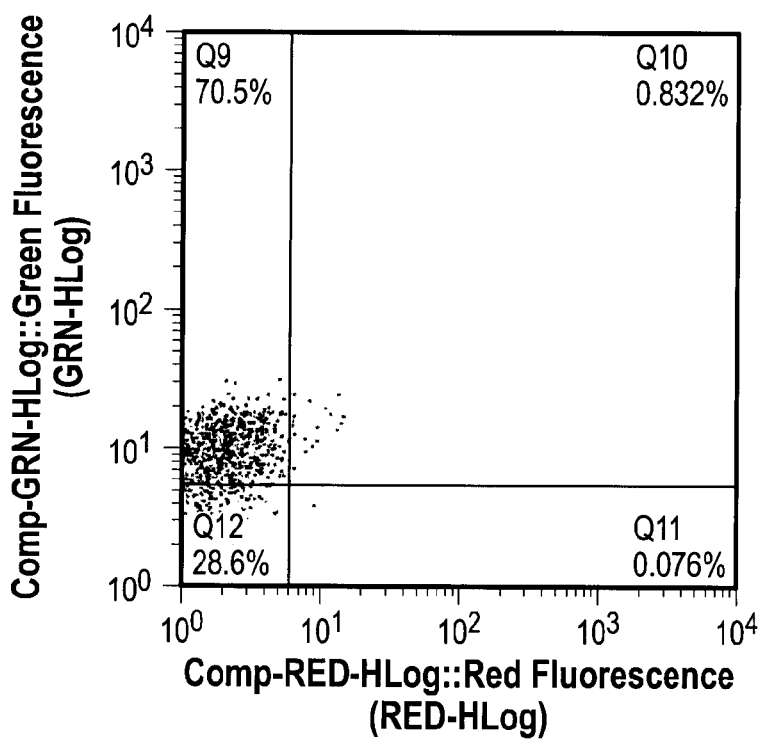
Figure 3A:
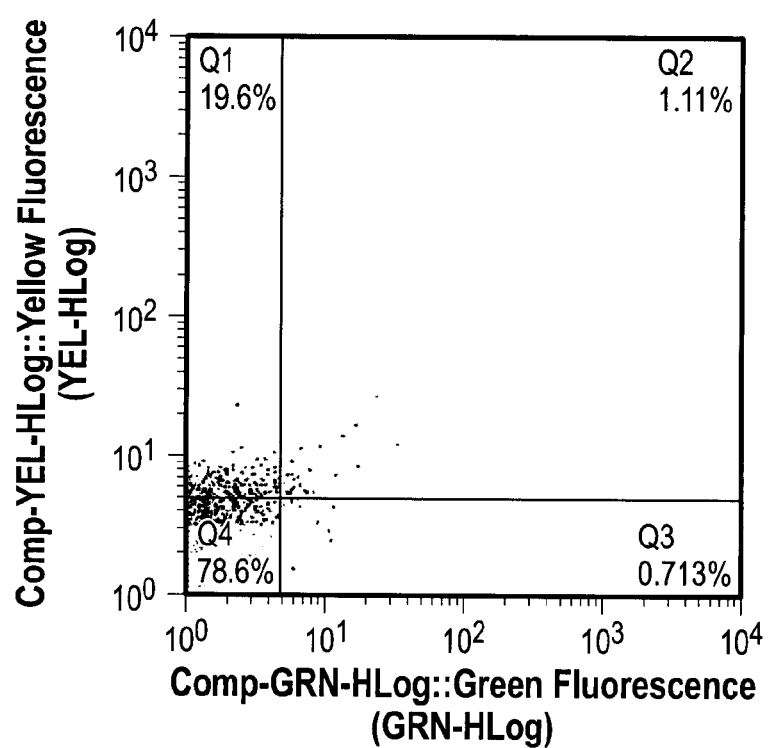
Figure 3A:
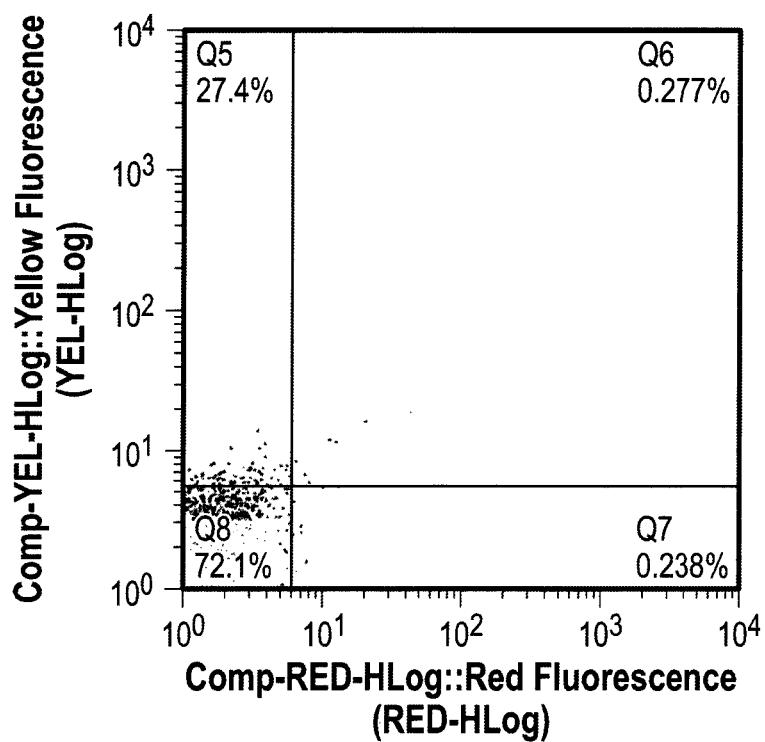
Figure 3A:
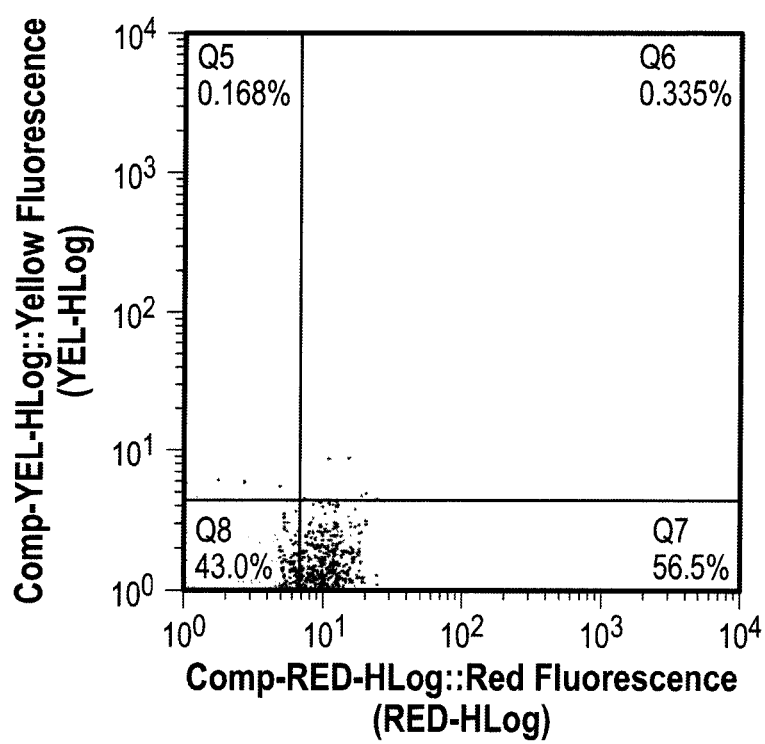
Figure 3A:
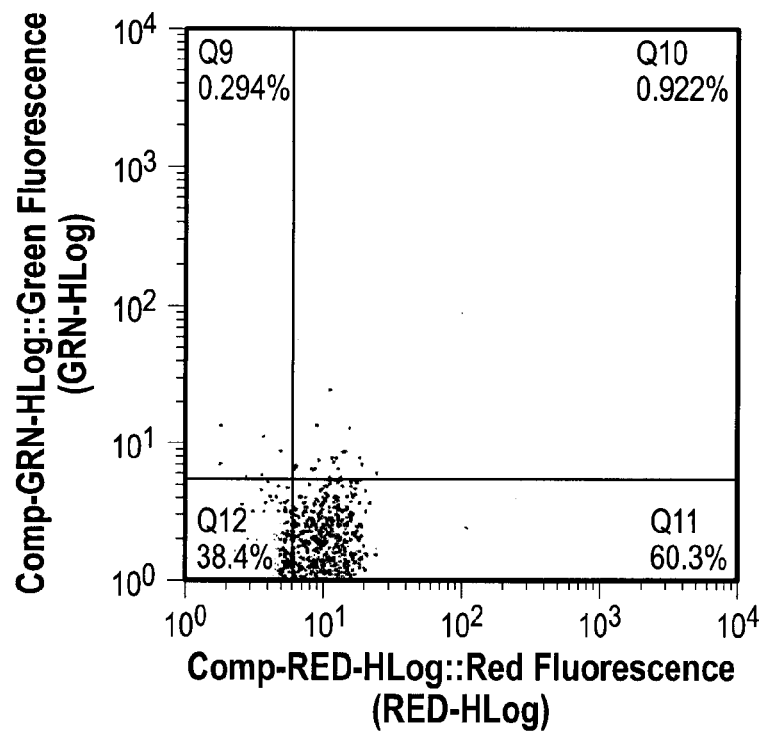
Figure 3B:
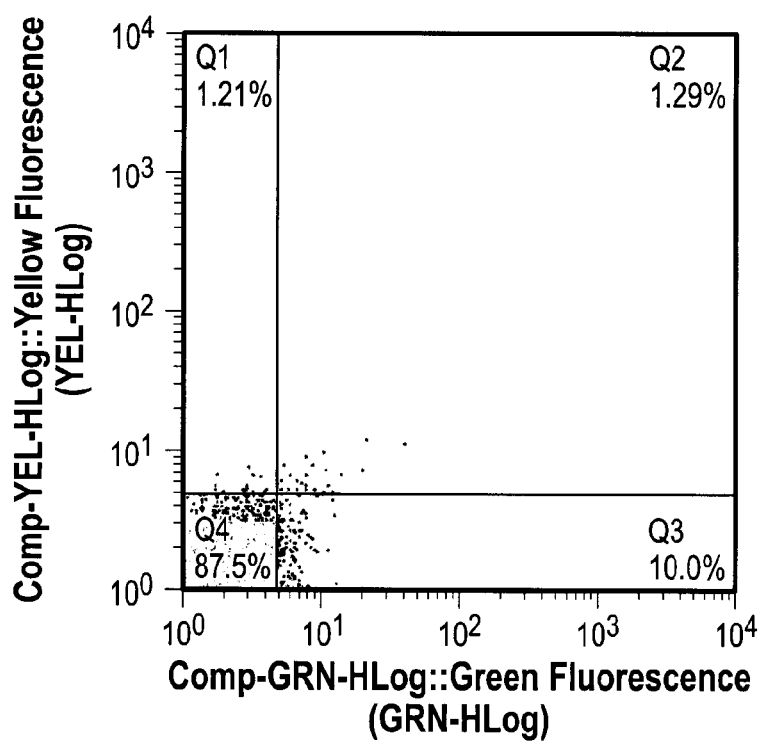
Figure 3B:
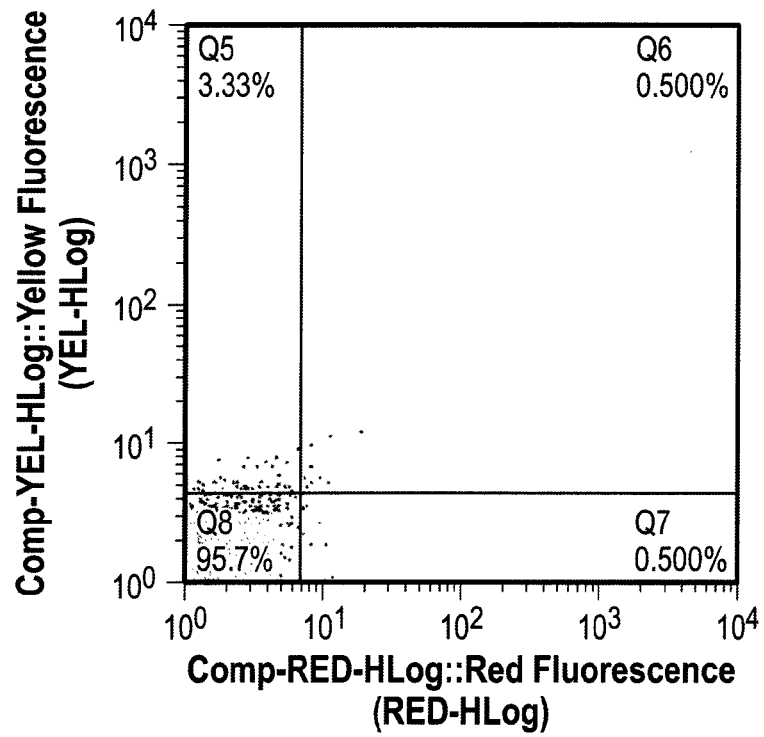
Figure 3B:
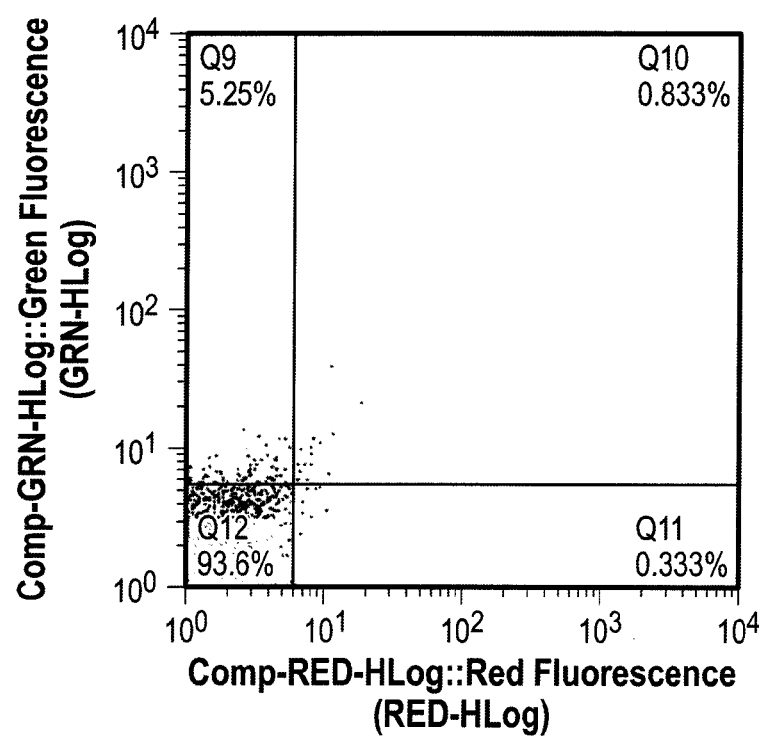
Figure 3C:
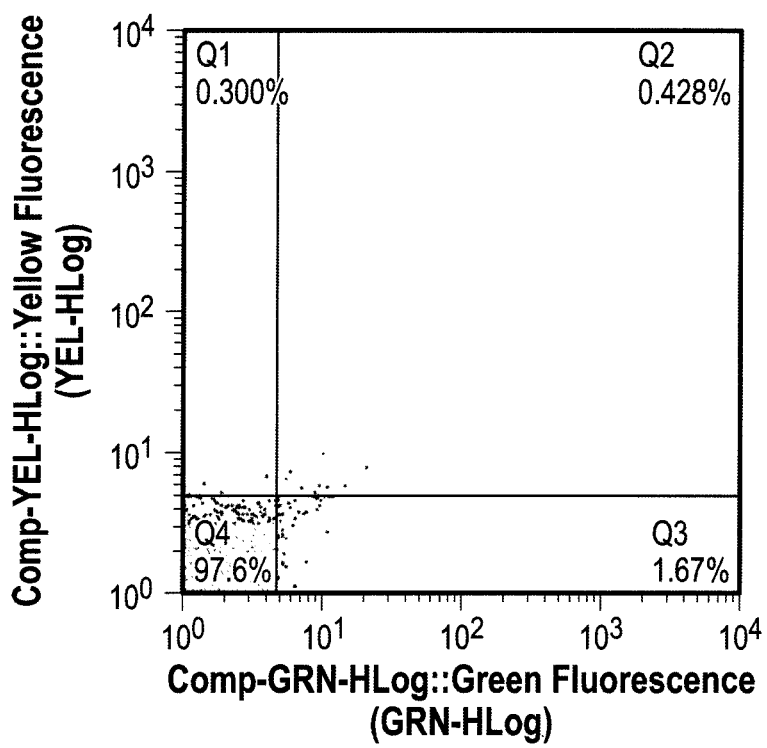
Figure 3C:
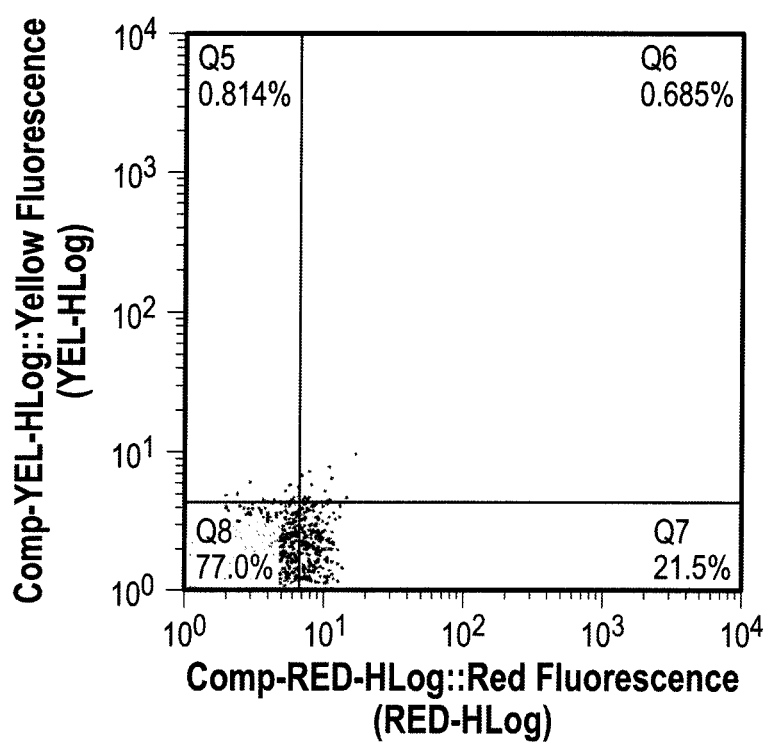
Figure 3C:
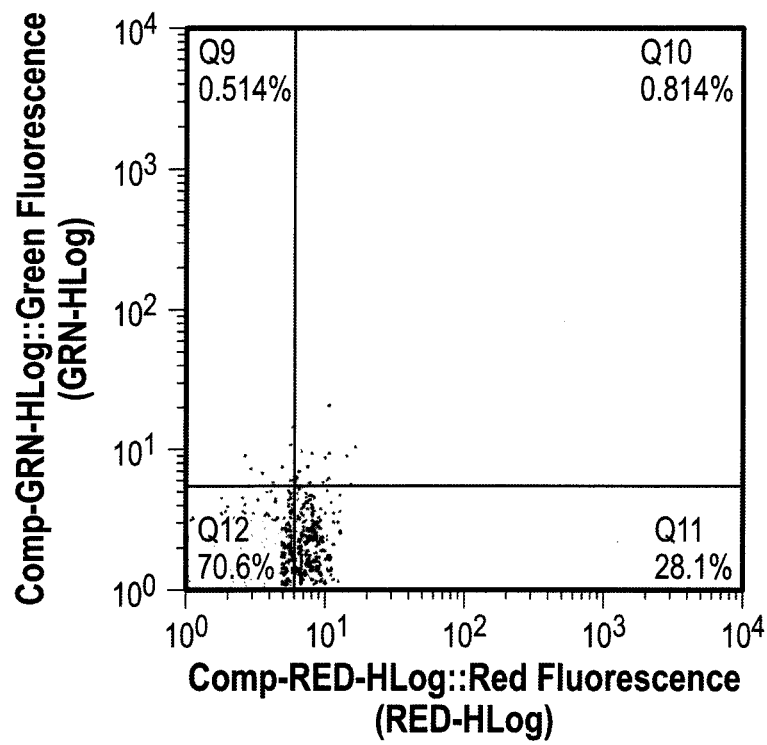
Figure 3D:
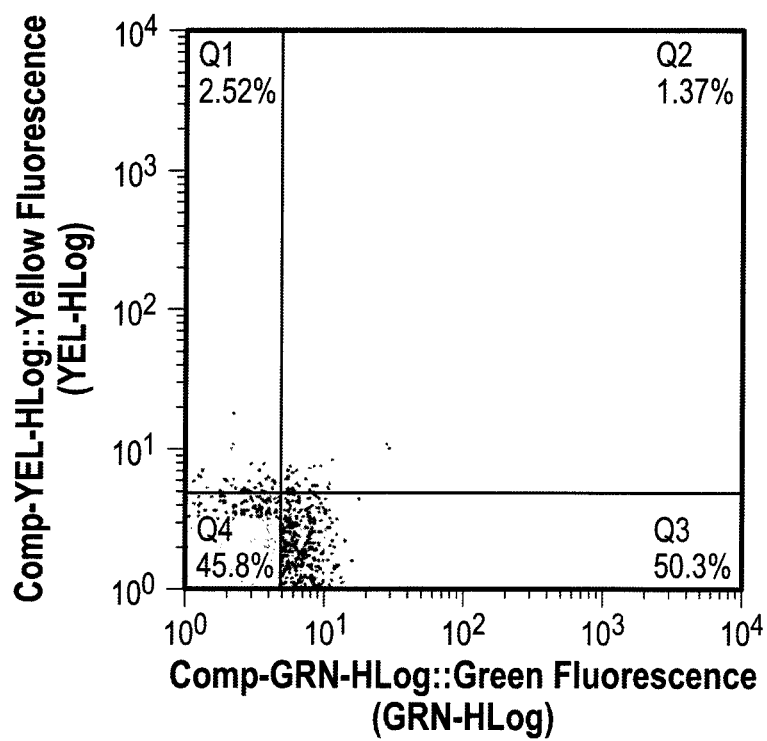
Figure 3D:
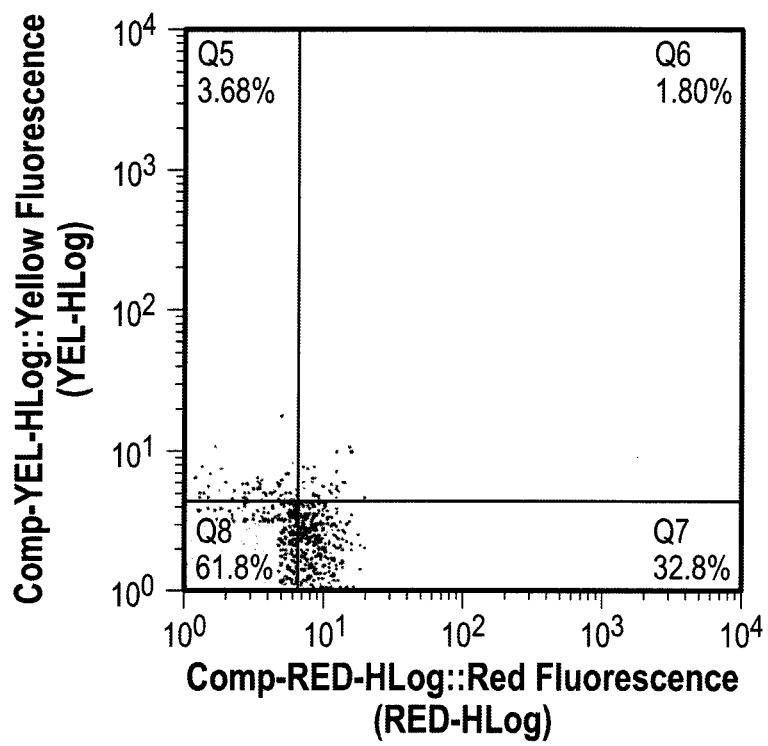
Figure 3D:
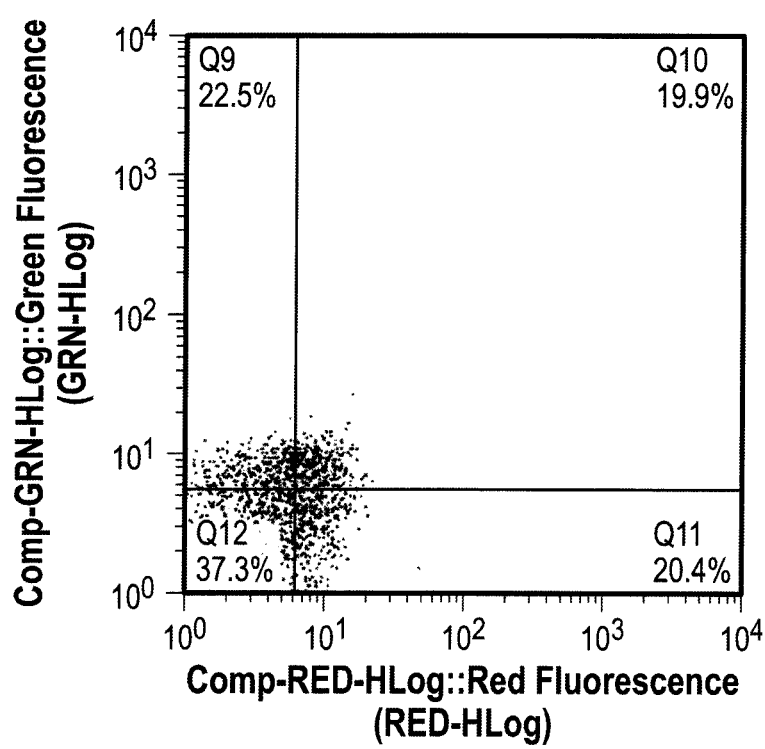
Figure 3E:
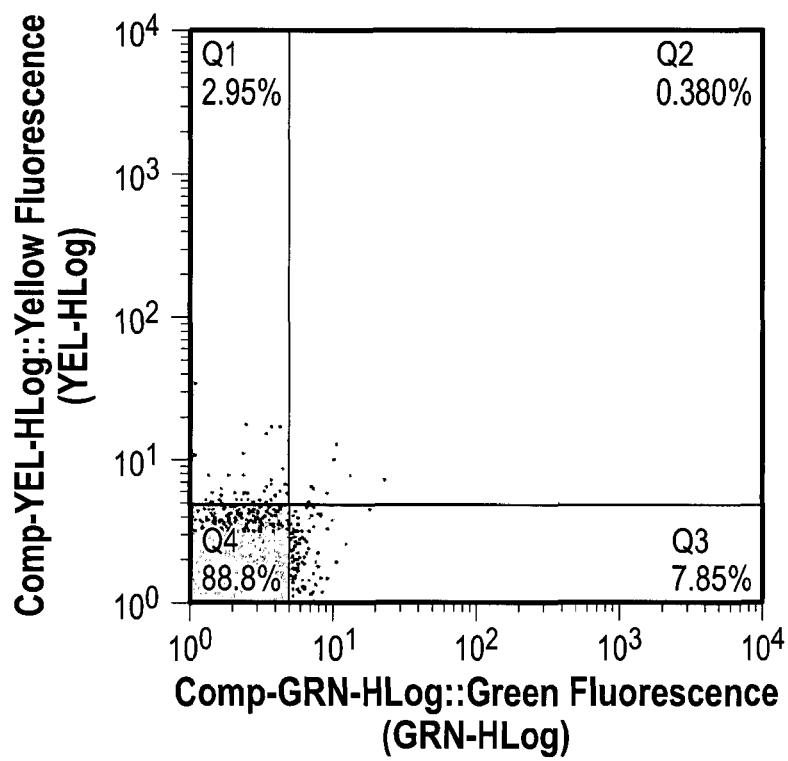
Figure 4A:
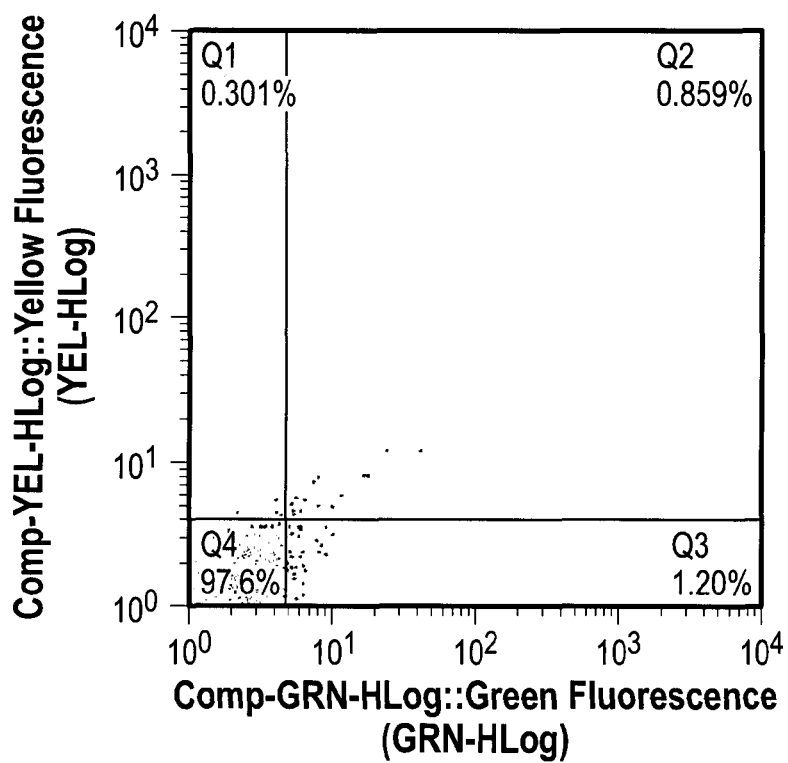
Figure 4A:
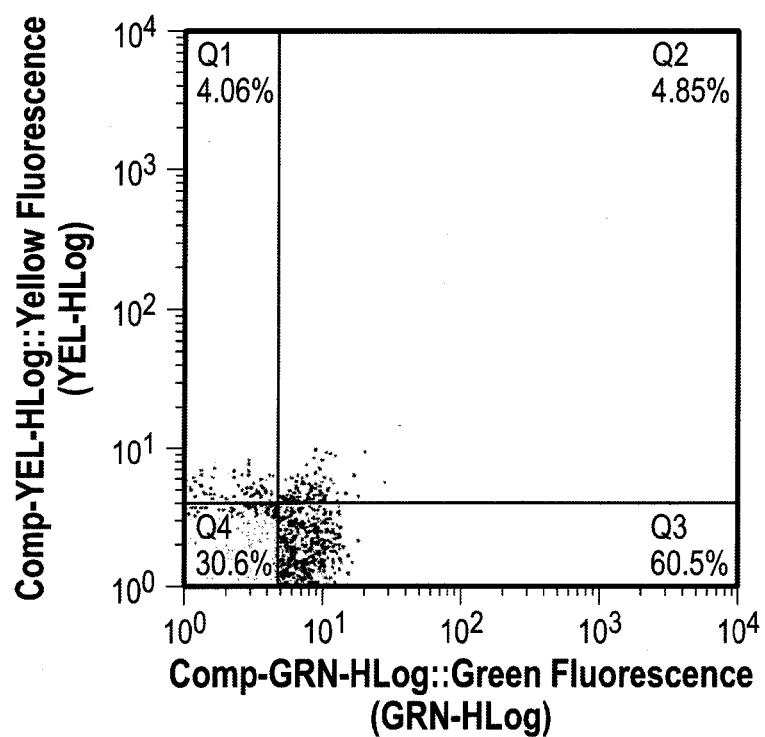
Figure 4A:
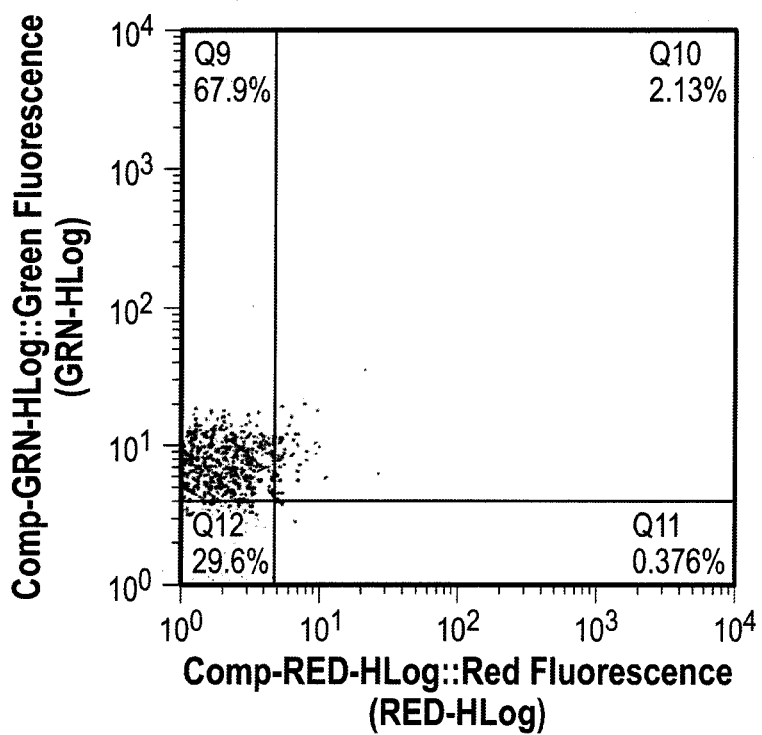
Figure 4A:
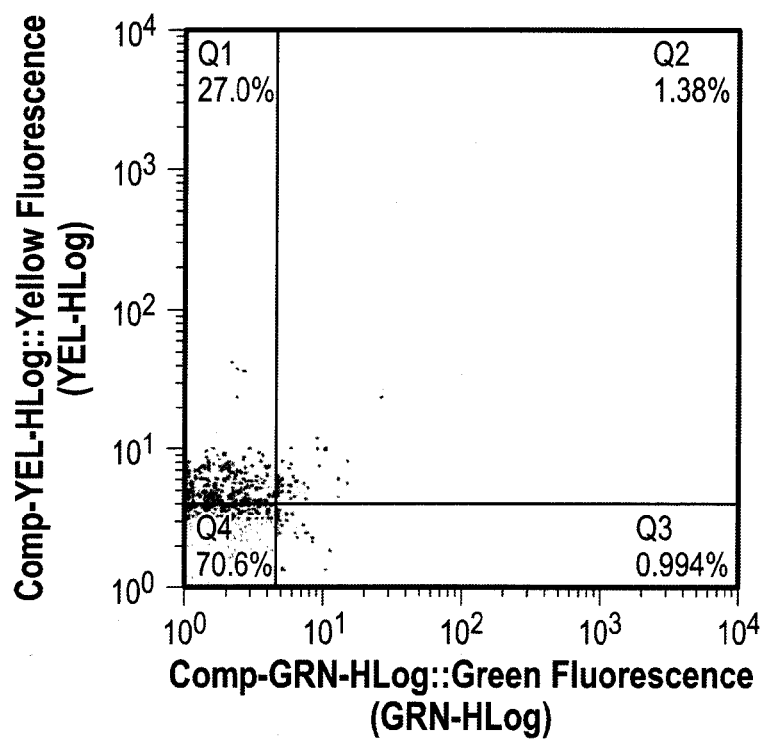
Figure 4A:
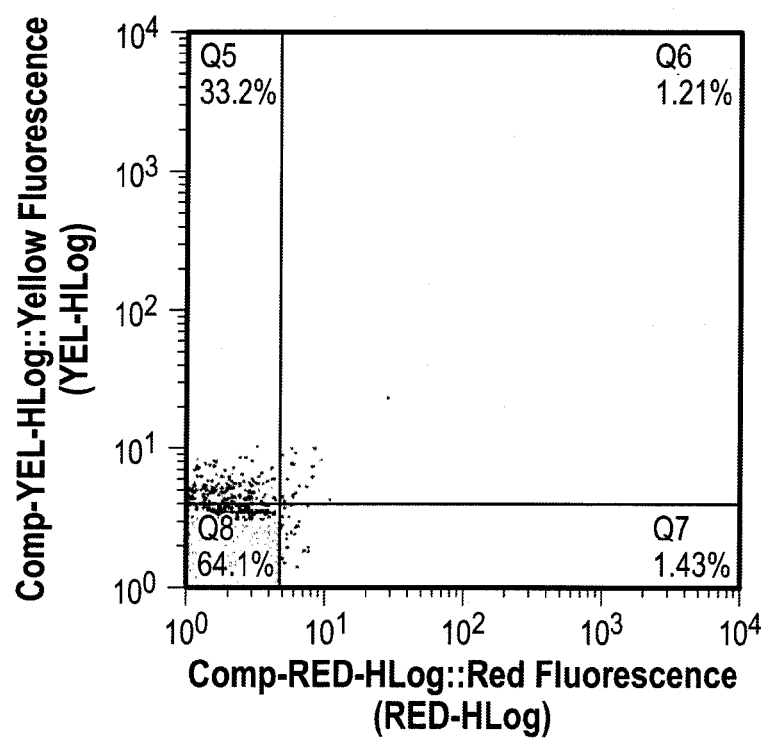
Figure 4A:
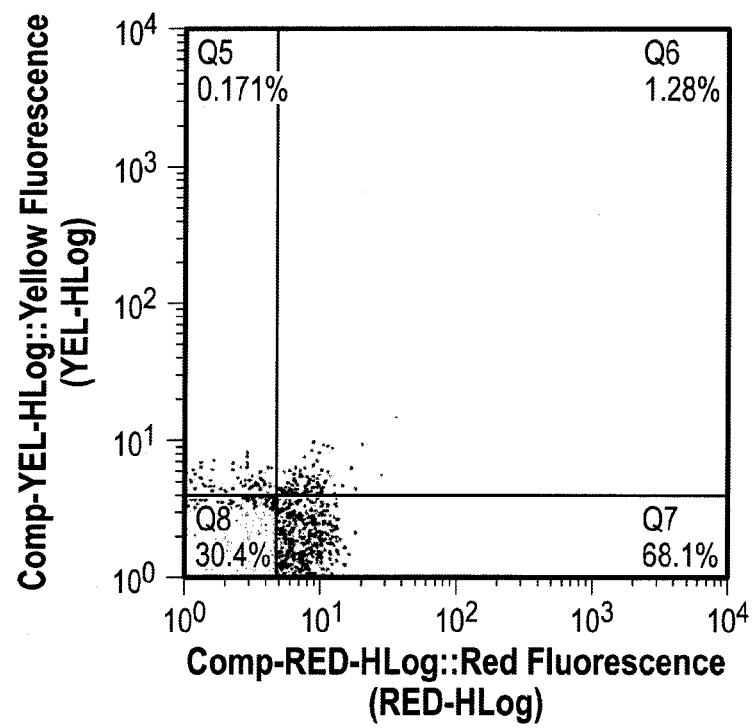
Figure 4A:
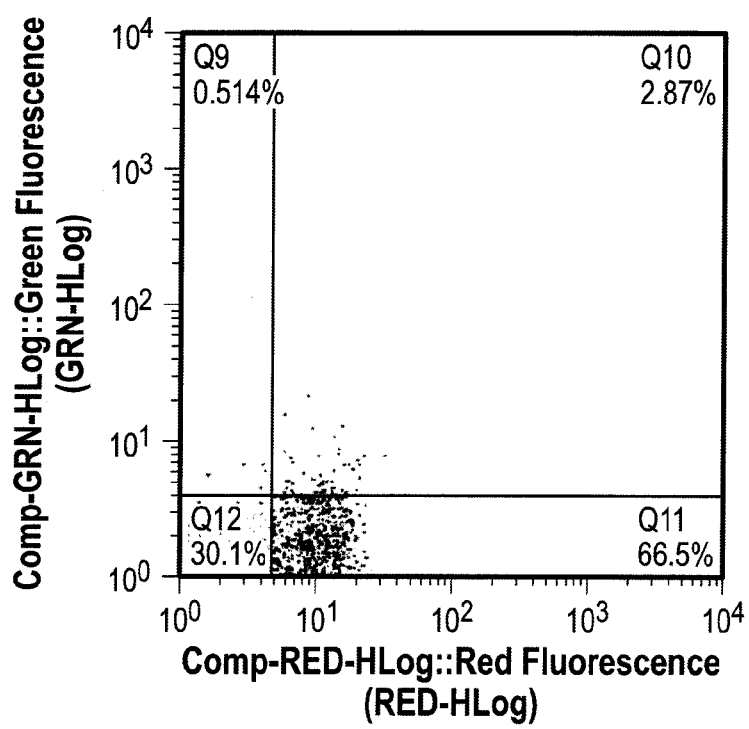
Figure 4B:
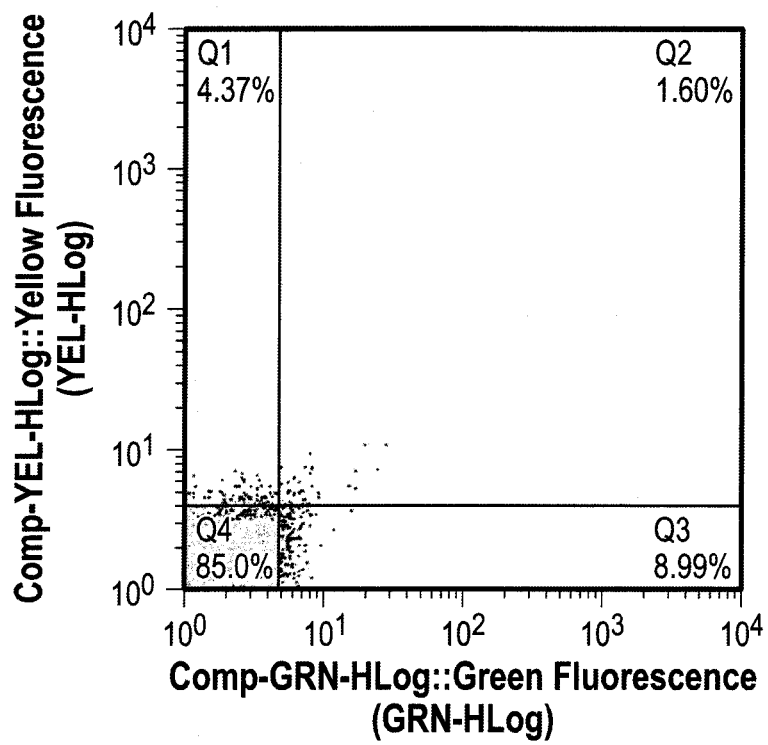
Figure 4B:
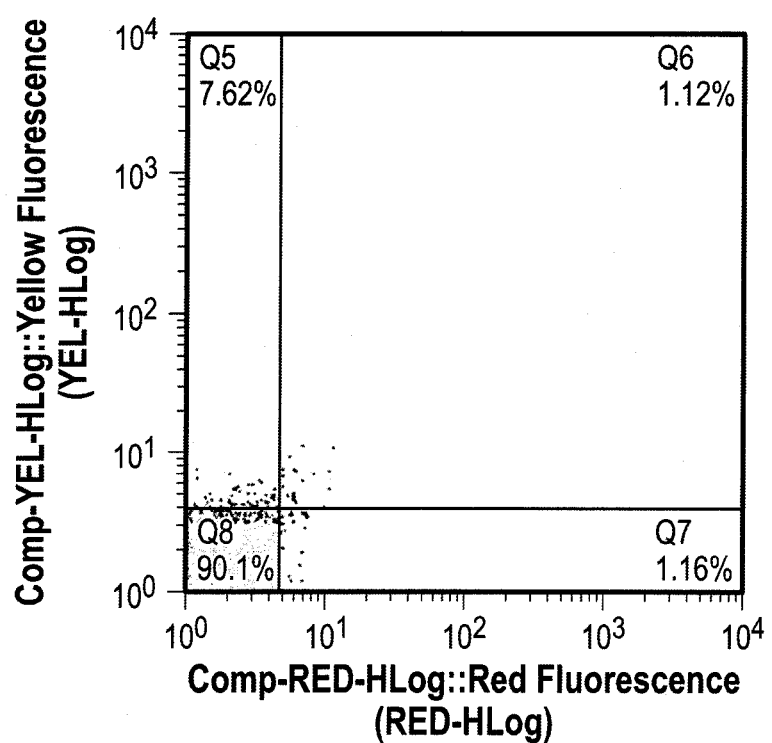
Figure 4B:
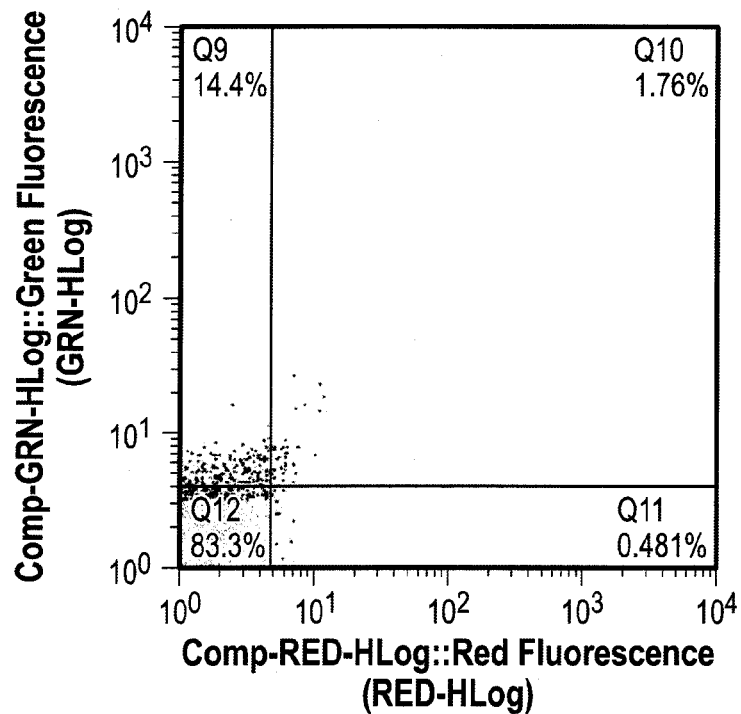
Figure 4C:
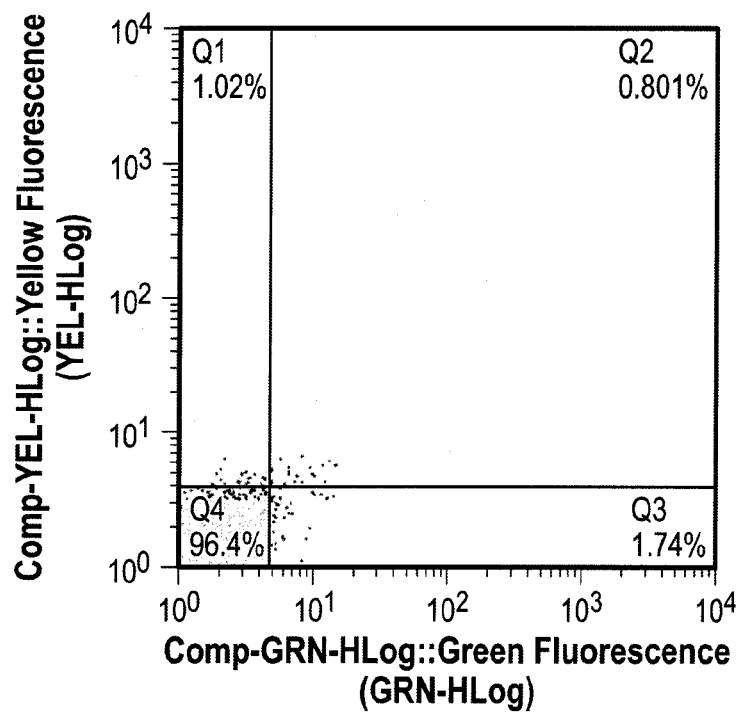
Figure 4C:
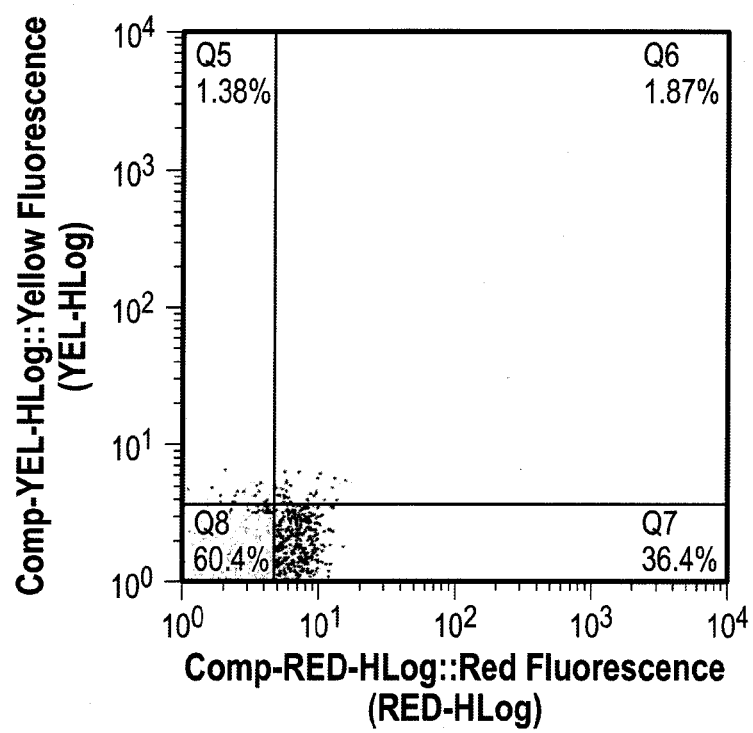
Figure 4C:
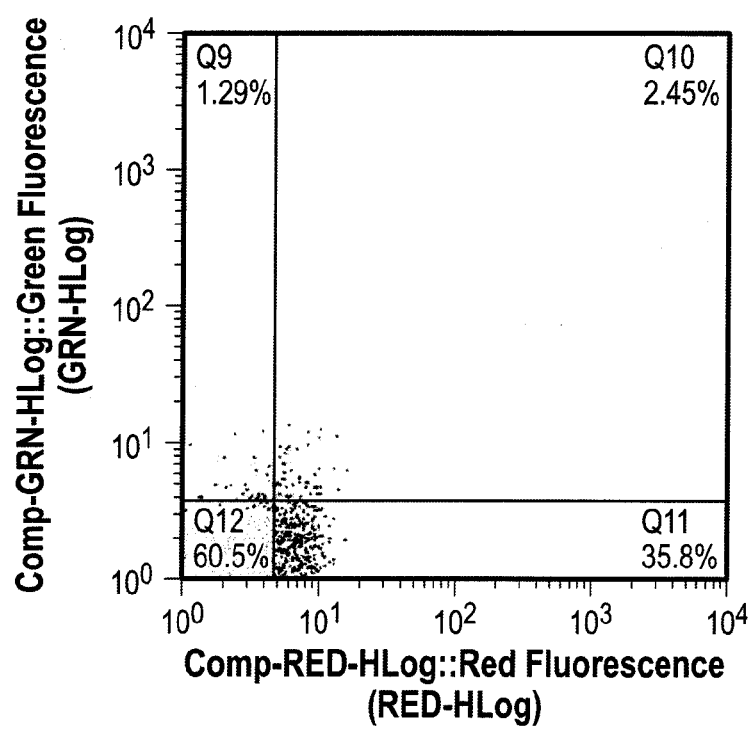
Figure 4D:
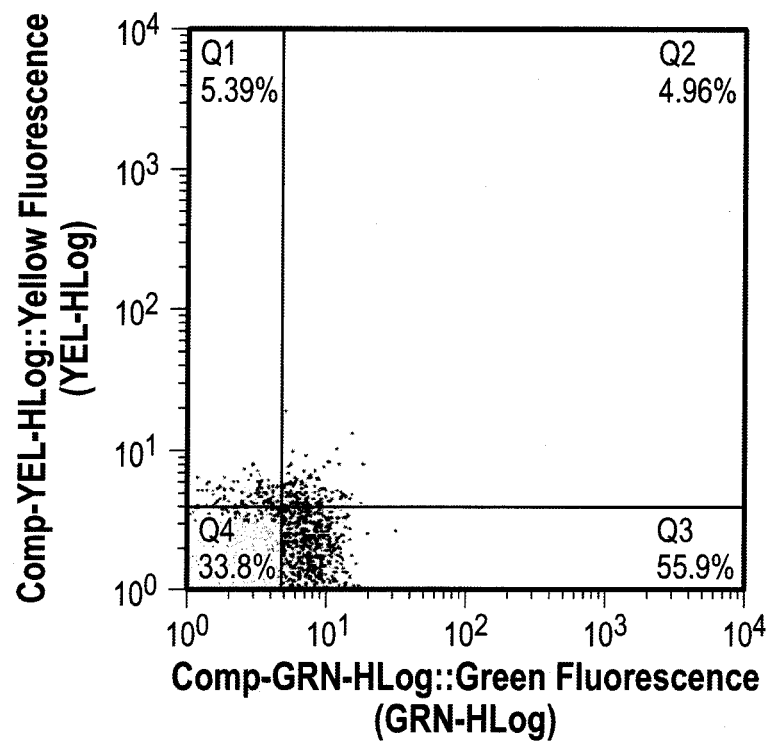
Figure 4D:
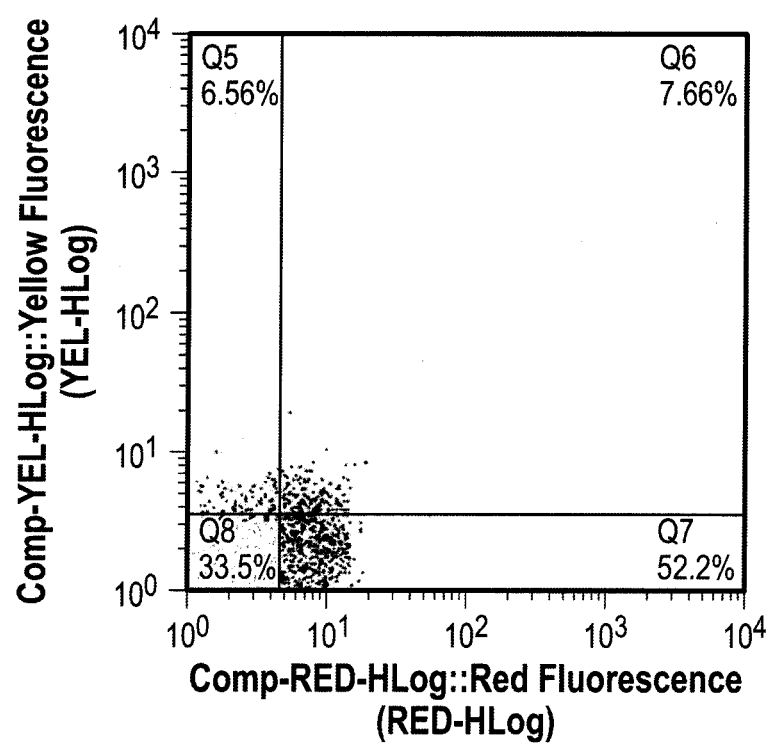
Figure 4D:
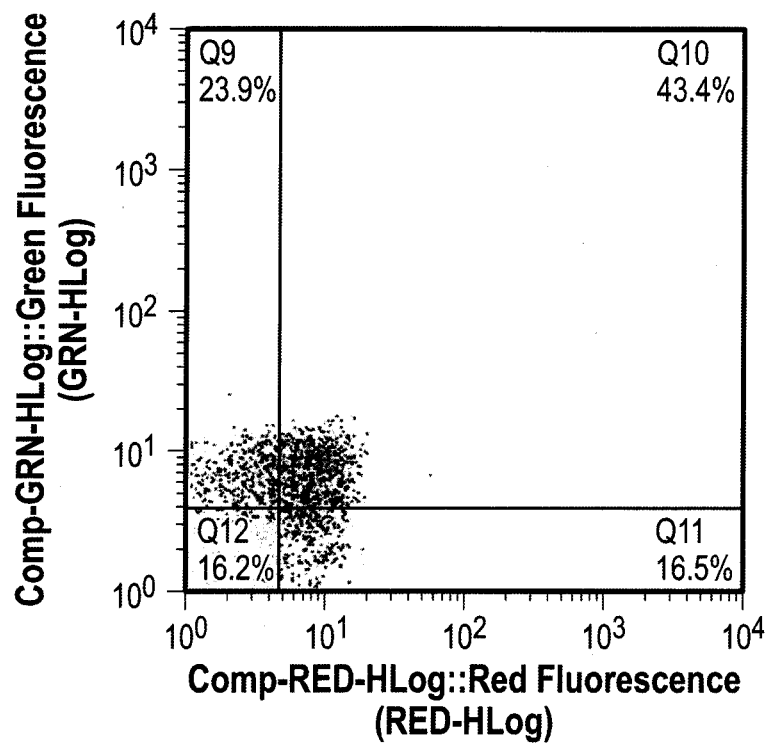
Figure 4E:
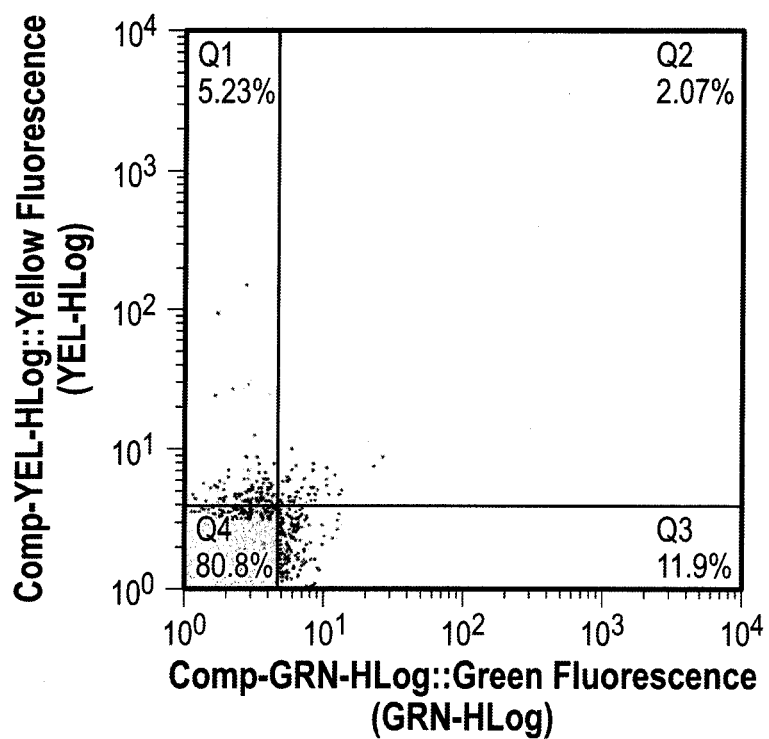
Figure 5A:
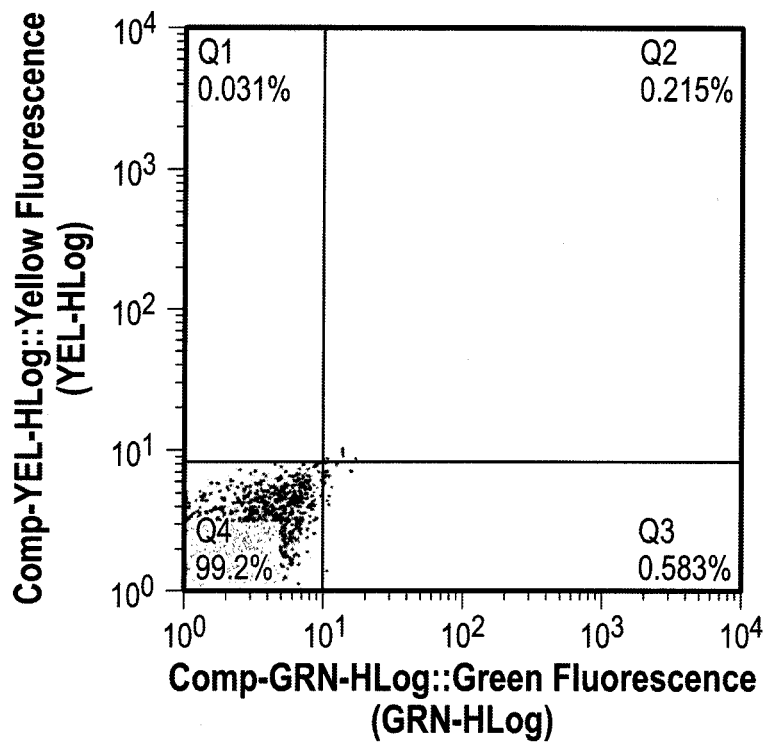
Figure 5A:
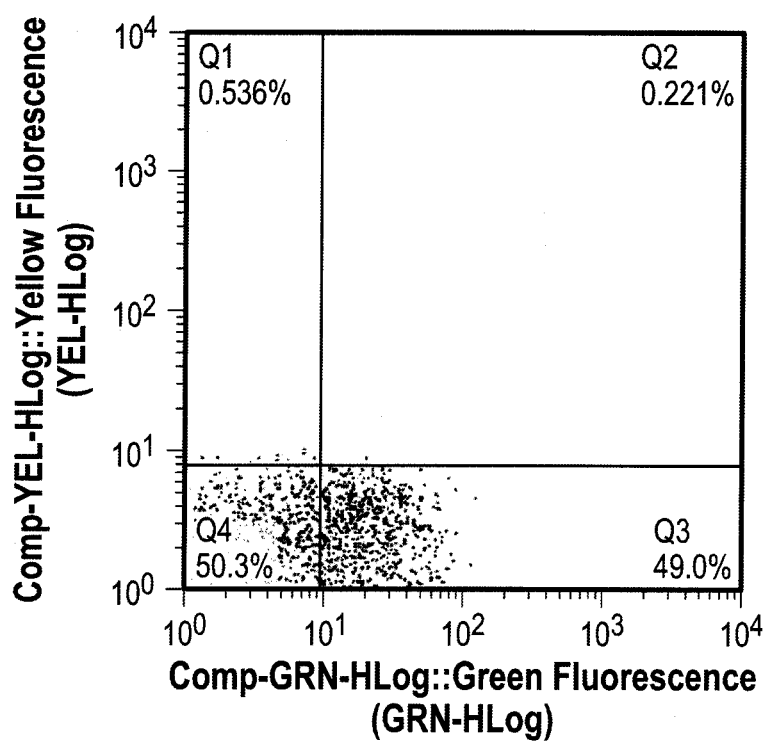
Figure 5A:
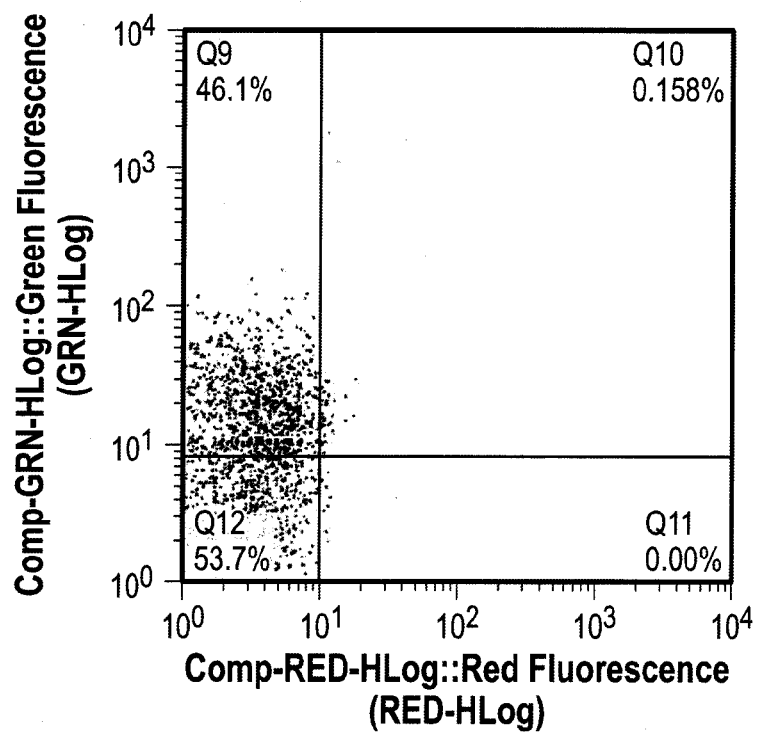
Figure 5A:
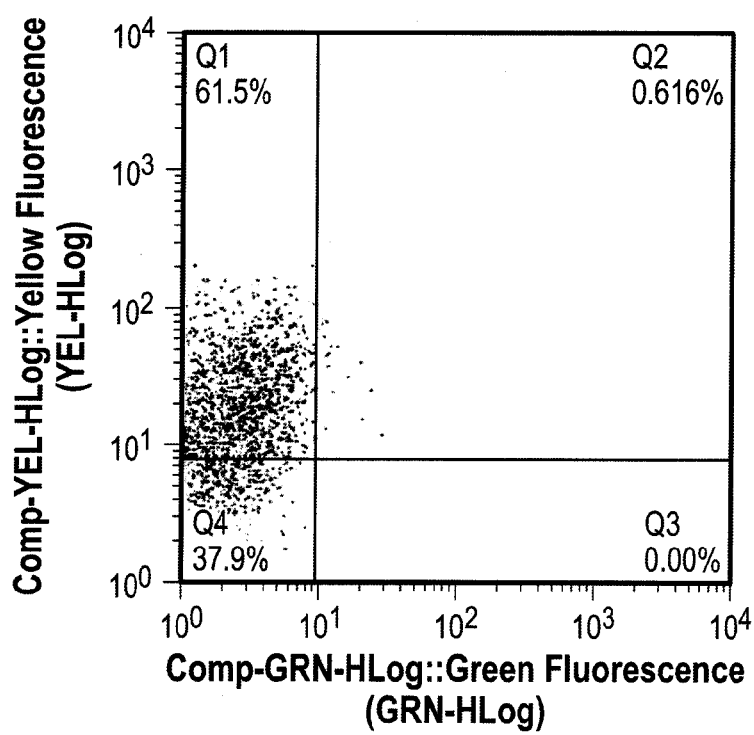
Figure 5A:
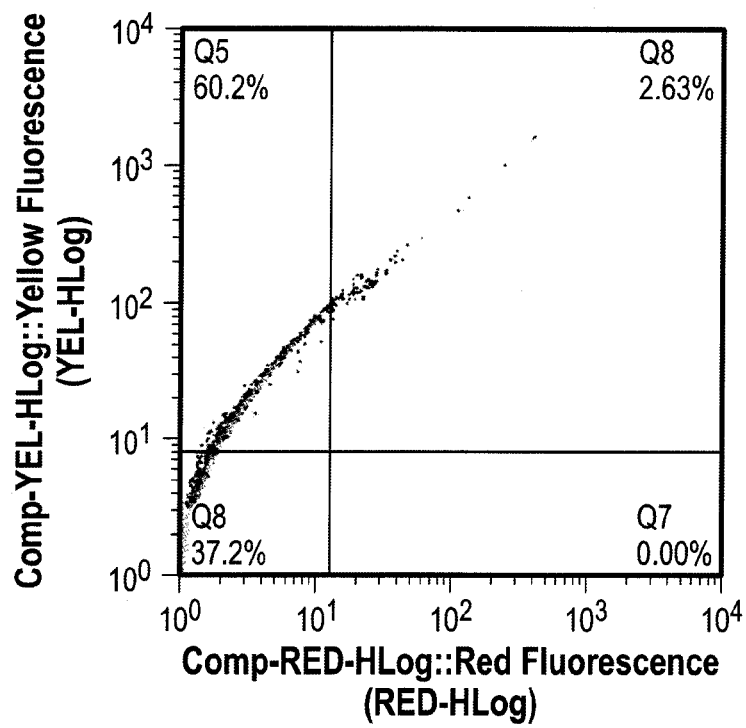
Figure 5A:
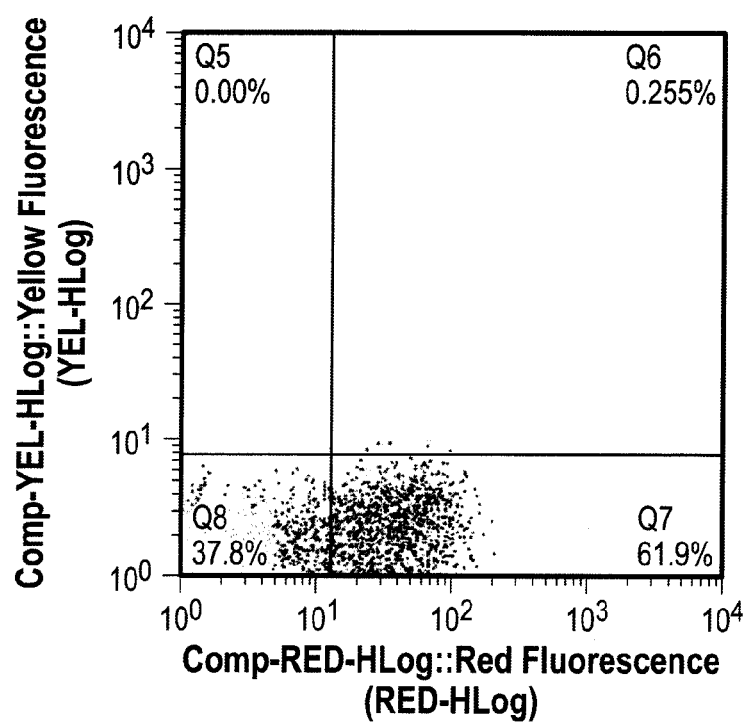
Figure 5A:
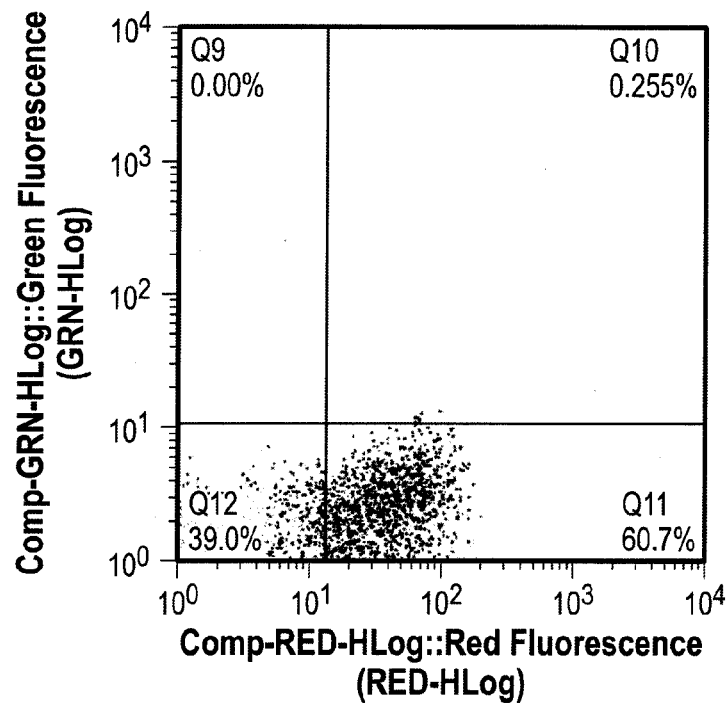
Figure 5B:
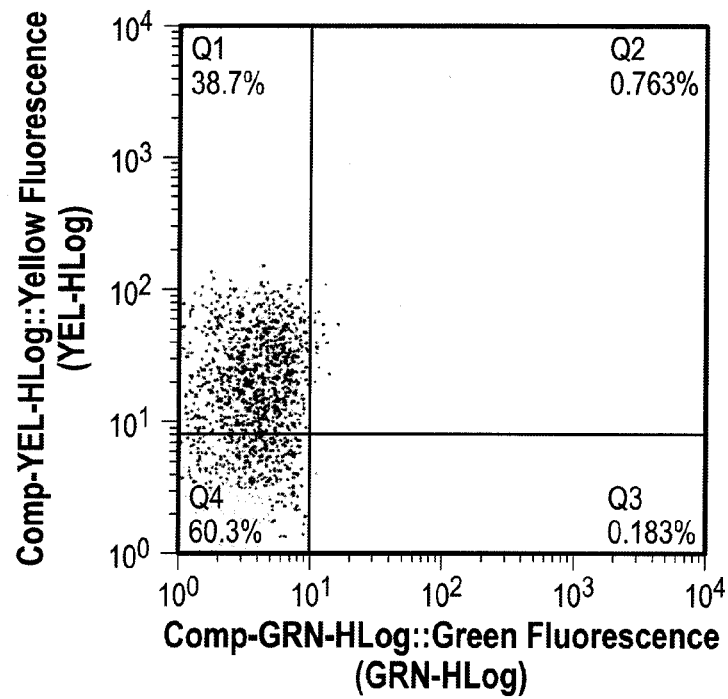
Figure 5B:
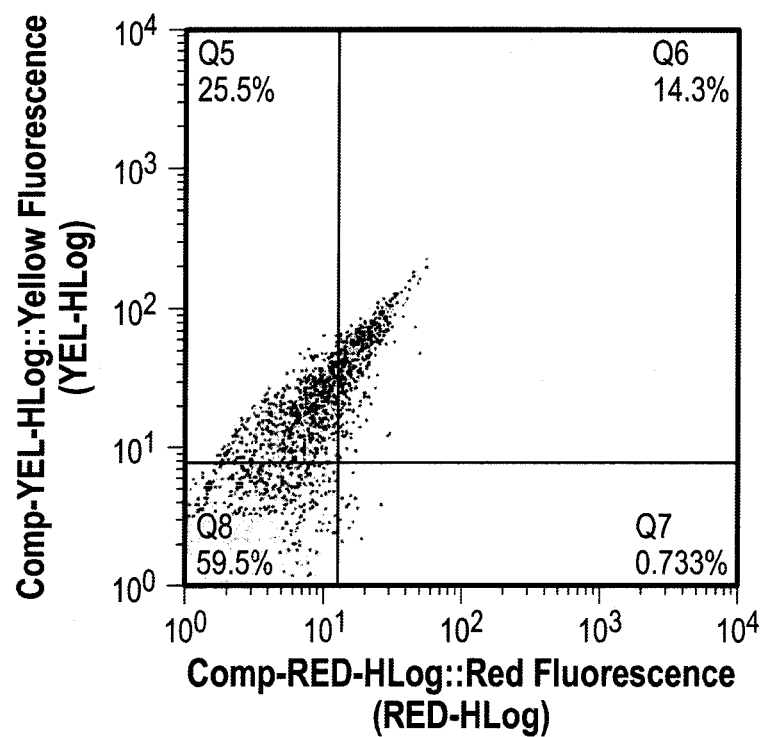
Figure 5B:
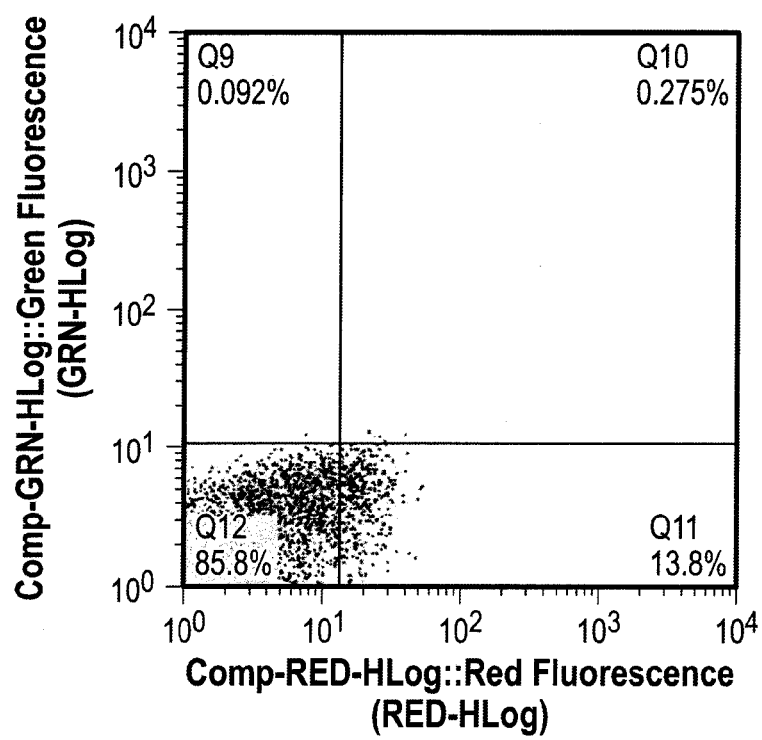
Figure 5C:
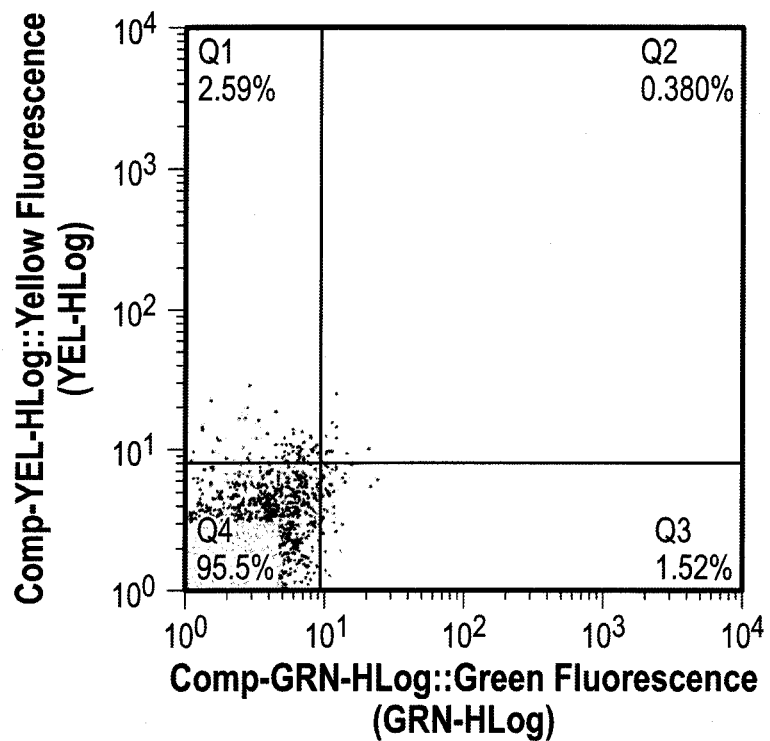
Figure 5C:
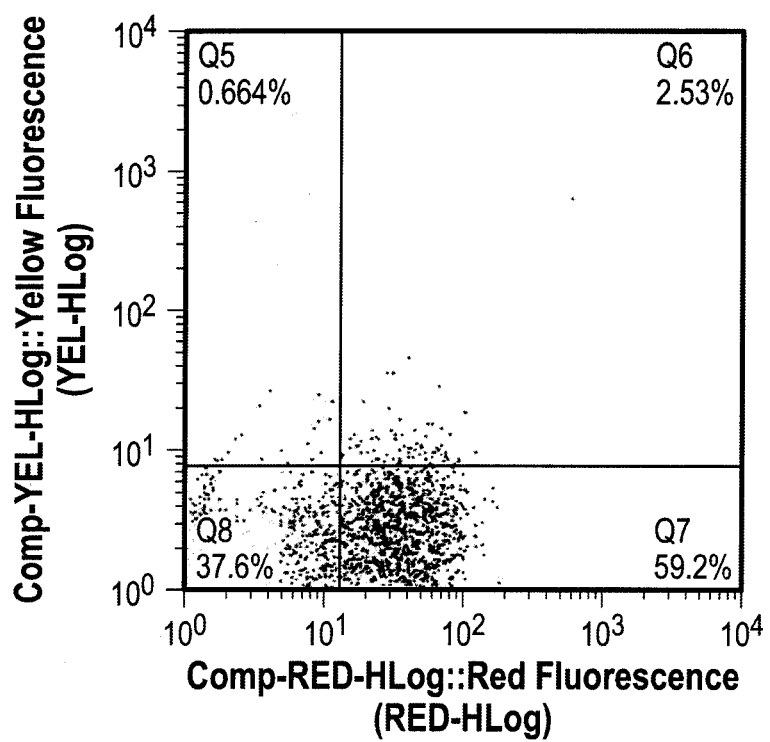
Figure 5C:
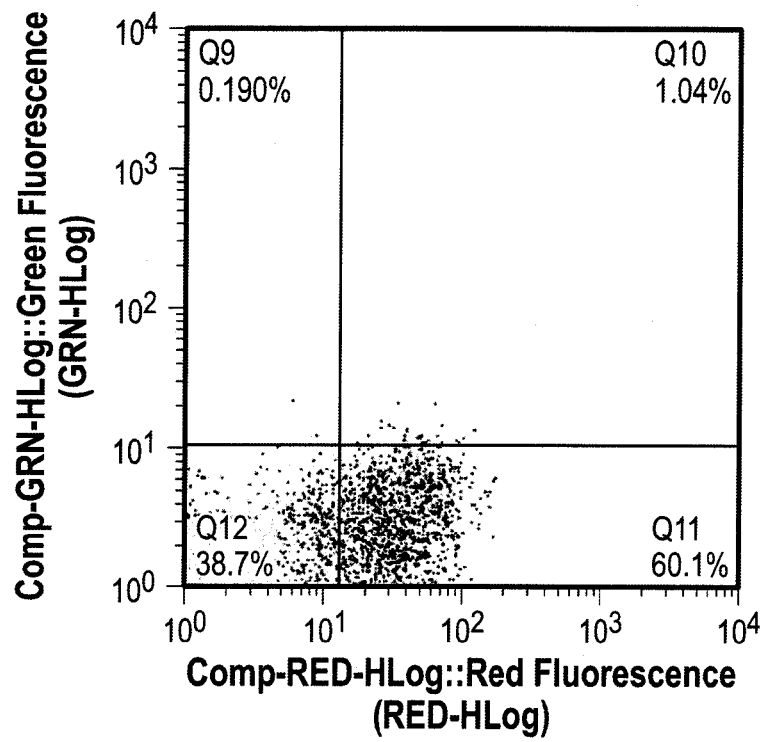
Figure 5D:
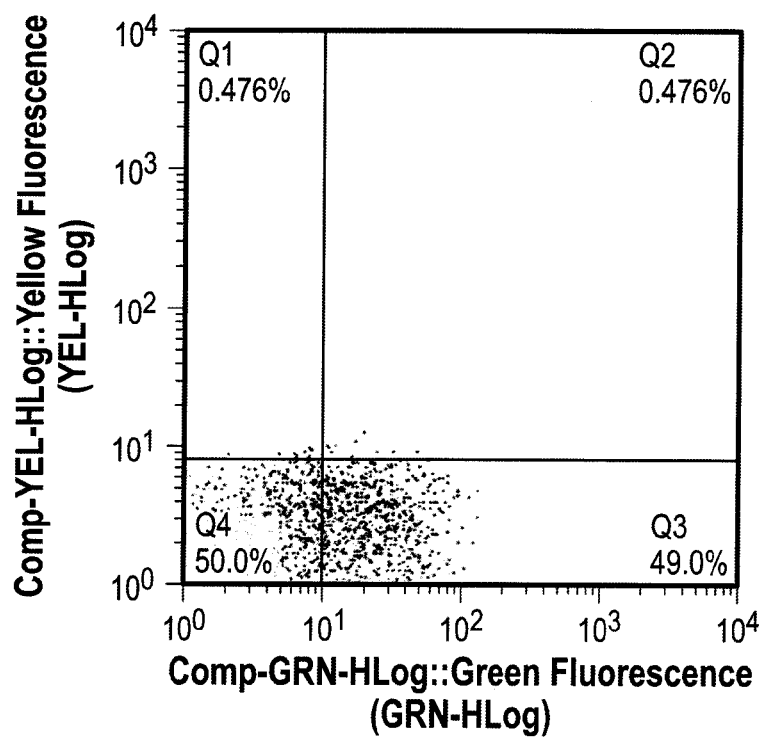
Figure 5D:
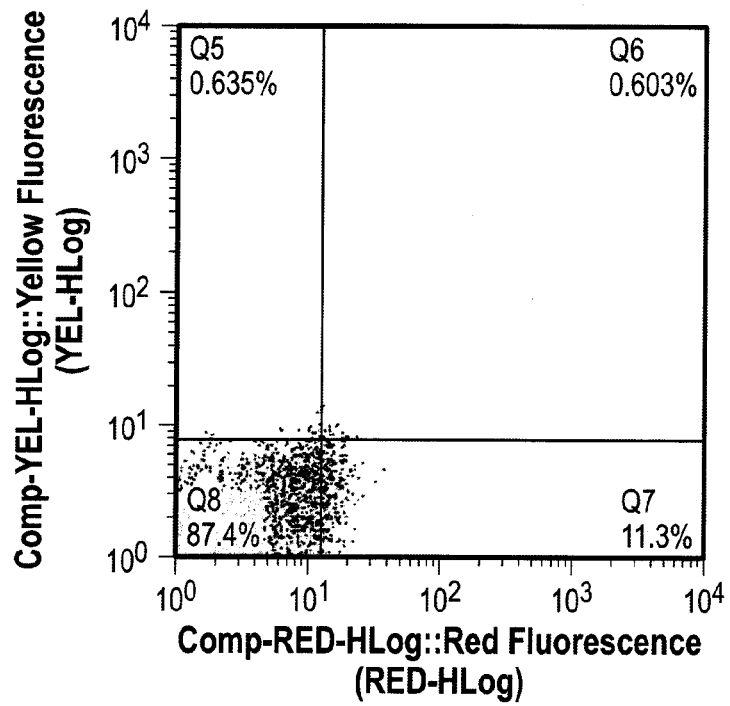
Figure 5D:
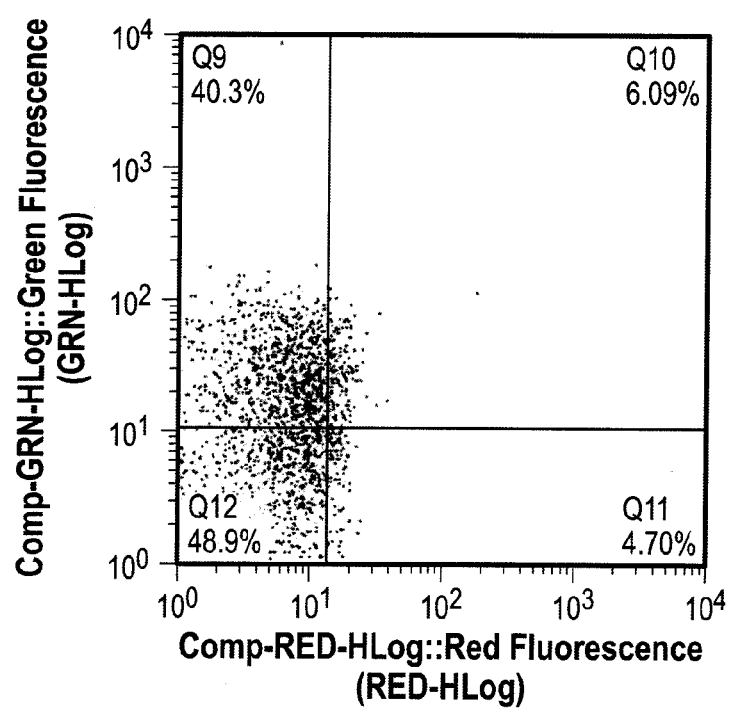
Figure 5E:
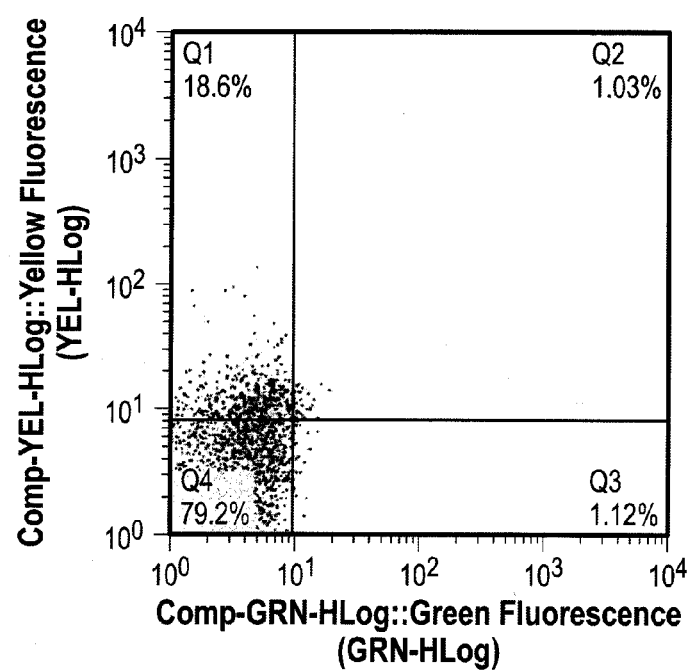

The following laboratory protocol was used to process adipose tissue and derive a stromal vascular fraction containing stem cells from adipose tissue (e.g., collected from patients as taught in the examples). It is to be understood that the protocol is exemplary and that the specifics may be modified by a skilled artisan in order to further optimize. Using this protocol, the inventor has processed hundreds of samples with consistently good results. As disclosed herein, and substantiated by Millipore studies (see FIGS. 1A-E, 2A-E, 3A-E, 4A-E and 5A-E) the subject ultrasonication protocol results in about 10-fold more viable cells than comparable adipose samples treated with collagenase. Also, the inventive methods result in the same cell population and cell types as collagenase isolation procedures, suggesting that the inventive methods preserve the integrity of all the desired stromal vascular fraction cells, and especially the cell types identified herein.

Inventive Protocol for Ultrasonic Cavitation and Processing of Stem Cells from Adipose Tissue Turn on Laminar Flow hood 3 minutes prior to procedure.
Set up Laminar Flow hood with sterile disposable drapes and tubes.
Turn on Millipore Guava and check software.
Check Gauge on Laminar Flow hood.
Attach the probe#14 to the Ultrasonic machine and tighten it with a wrench to be secured in place.
Log in fat into Guava flow cytometer computer.
MAKE SURE ALL TUBES ARE CLEARLY LABELED WITH NAME AND DATE!!!
A timer is used on 10 min. preset.
Place probe into fat (make sure the probe does not touch the plastic)
Slowly increase Cycle and Amplitude once the probe is submerged into syringe with fat, until reach Cycle 0.9 and Amplitude 90%;
After 5 min. stop the ultrasonic process and raise the probe to a level of 40 cc on the syringe; check the sample and make sure that is not overflowing;
Remove specimen from Ultrasonic and pour the contents into a red top sterile conical specimen tube for filtering;
Divide in equal amounts in two sterile red top conical specimen tubes, then add equal amounts of 0.9% Sodium Chloride;
Centrifuge both specimens for 3 min. @500 rpm.

When spinning is complete you will have a specimen that is layered, liquid on the bottom (with a pellet) and fat on top.
Using a 20 cc syringe and metal infusion cannula attachment (spinal needles) submerge to bottom of specimen tube and remove liquid stem cells solution including the pellet; (from this sample take approximately 2 cc of liquid to be used for testing with Fluocitometer).
Test sample with Millipore Flow Cytometer.
Pipette sample SVF into specimen tube.
Pipette Guava reagent into sample and mix.
Place sample into dark for 5-20 minutes.
Place sample into flow cytometer.
Run Guava Soft program
Record all results
Dispose biological waste into BIOLOGICAL WASTE CONTAINERS
CLEAN LAMINAR FLOW HOOD WITH ANTIBACTERIAL AGENT AND THEN CLEAN WITH ANTIMICROBIAL WIPES
CLEAN ALL INSTRUMENTS AND AUTOCLAVE AS PER PROTOCOL.
ALWAYS USE GOOD LAMINAR FLOW HOOD PROTOCOL WHEN HANDLING ALL SPECIMENS AND TUBES

EXAMPLES

Example 1

Preparation of Adipose Tissue from Human Donor

Method 1: Preparation of an Aspirate Containing Adipose Tissue by Liposuction

An excess amount of Tumescent solution (saline containing 0.0001% adrenalin), which exceeds the amount of liposuction to be aspirated prior to the liposuction operation, is infused into hypodermic fat layer (tumescent method), and thereafter cannulae having 2-3 mm of inner diameter (made of metal with aspirator) are used for the liposuction operation. Liposuction operations are well known in the art, and for example, can be referred to in Biyo Seikei Shujutsu Practice 2 (Cosmetic Operation Practice 2), ed. Masanari ICHIDA, Ryusaburo TANINO, and Yoshiaki HOSAKA, published by BUNKODO, pp. 429-469, which is incorporated herein by reference in its entirety.

Aspirated fat is washed with saline. About five to ten liters of washed aspirate was generated, and the resultant adipose tissue derived cellular materials are used for derivation of stromal vascular fractions.

Method 2: Preparation of Adipose Fat Tissue by Surgery

Fat tissue was obtained by surgery from human subjects who had given their informed consent. Separation was conducted with techniques well known in the art. Briefly, human fat tissue was aseptically separated from fat tissue suctioned from human subjects who had given their informed consent. The resultant adipose tissue derived cellular materials are used for derivation of stromal vascular fractions.

Example 2

Preparation of a Stem Cell Suspension from an Aspirate of Liposuction

Adipose tissue derived from liposuction aspirates or surgically as described in the previous example are placed in a suitable tube and a biologic solution if desired (e.g., phosphate buffered saline solution or normal saline solution) and the adipose tissue in the composition is placed contact with the ultrasonic probe of an ultrasonic cavitation device as described in the Materials and Methods section above.

In particular, the Amplitude is set at about 50-100%, typically about 100%, Cycle 1.0 and about 30-60 cc fat lipoaspirate is placed into a tube, 60 cc tube size, 28 mm diameter and 110 mm length and is treated by ultrasonic cavitation for about 10 min, and then adjust up after 5 minutes using a 14 mm ultrasonic rod.

The device may be set at about 50-100% intensity and frequency of about 10-100% for about 5-60 minutes for about 45-60 cc of adipose tissue. This treatment explodes the fat cells and thereby releases the stromal vascular fraction into the biologic solution, e.g., phosphate buffered or normal saline. As noted this treatment does not include the addition of collagenase or equivalent enzyme intended to break down collagen as cell dissociation is instead accomplished by ultrasonic sonication.

Preferably after ultrasonication the resultant solution is allowed to settle over time or is treated by centrifugation. The fat will float to the top. This solution will contain the stromal vascular fraction at the bottom which includes adipose-derived stem cells, endothelial cell precursors and other cells and this fraction is uncontaminated by exogenous enzymes such as collagenases.

The fat containing supernatant may be discarded. In addition as the desired cells may also float, an aspirator may be used to carefully perform suction without damaging the cells.

Example 3

Characterization of Recovered Stem Cells

The stromal vascular fraction containing stem cells recovered in Example 2 and using the Protocol above is characterized by known methods, e.g., flow cytometry or FACS, e.g., using antibodies that detect markers expressed on mesenchymal and stromal adipose derived stem cells. These methods will detect the presence of viable stem cells.

It is to be understood that the protocols disclosed herein are exemplary and that the specifics may be modified by a skilled artisan in order to further optimize. Using the specific protocol reported in the Materials and Methods section above, the applicant has processed over 200 samples with consistently good results. The stem cells resulting therefrom have been used to treat patients. In addition, the applicant has compared the stem cell containing cell samples derived according to the invention to those derived by conventional procedures (collagenase derived samples). More specifically, adipose-derived stem cell samples produced according to the invention were compared to those obtained in a study by Millipore. The comparison revealed that the inventive ultrasonic cavitation procedures result in the same cell population. Unexpectedly, the inventive procedure is much more efficient, i.e., it consistently results in about 10 times the number of cells for the same amount of fat.

Accordingly, those skilled in the art will readily find the industrial applicability of the present invention in pharmaceutical and cosmetic industries and the like.

The invention claimed is:

1. A method for recovering stromal vascular fraction cells from blood vessels contained in or proximate to human adipose tissue comprising treating about 45-60 cc of adipose tissue comprising fat cells, blood vessels, and a stromal vascular fraction in a 60 cc tube with ultrasonic cavitation for about 10 minutes using a 14 mm ultrasonic rod, wherein ultrasonic cavitation is effected by slowly increasing cycle and amplitude once the ultrasonic rod is submerged into the tube containing the adipose tissue, wherein after 5 minutes, the ultrasonic process is stopped and the ultrasonic rod is adjusted up in the tube and continued for the 5 minutes, and wherein the fat cells and blood vessels are exploded, thereby releasing substantial numbers of intact stromal vascular fraction cells while substantially maintaining the viability of the cells constituting the stromal vascular fraction.

2. The method of claim 1, wherein said method does not include the addition of an enzyme that breaks down collagen or a endopeptidase.

3. The method of claim 1, wherein the adipose tissue is obtained from the stromal compartment of the body of a living or non-living donor, mesenchymal compartment of the body of a living or non-living donor, a liposuction derived aspirate, solid fat obtained from a human cadaver, or solid fat obtained from a living donor.

4. The method of claim 1, wherein the adipose tissue is comprised in phosphate buffered saline, normal saline, or another biologically acceptable liquid.

5. The method of claim 1, wherein a high intensity ultrasonic processor or high intensity cavitation device is used.

6. The method of claim 1, wherein after ultrasonic cavitation the resultant composition is allowed to settle or is centrifuged resulting in the separation of fat and stromal vascular fraction cells into a supernatant and a pellet, respectively, optionally, the stromal vascular fraction cells may be isolated from the pellet.

7. The method of claim 1, wherein after ultrasonic cavitation the stromal vascular fraction cells are assayed for the presence of adipose-derived stem cells including CD34 and/or Thy-1 or CD90 expressing stem cells.

8. The method of claim 7, wherein the stromal vascular fraction cells are assayed by flow cytometry.

9. The method of claim 7, wherein after ultrasonic cavitation the stromal vascular fraction cells are fractionated using fluorescence activated cell sorting (FACS) based on cell surface antigens which are specific to adipose-derived stem cells.

10. The method of claim 9, wherein the resultant isolated adipose-derived stem cells are expanded in culture.

11. The method of claim 9, wherein the resultant isolated adipose-derived stem cells are infused into a patient.

12. The method of claim 1, wherein the stromal vascular fraction comprises endothelial cells, endothelial progenitor cells, mesenchymal stem cells, macrophages, dendritic cells, Kupffer cells, platelets, granulocytes, B cells, T cells, NK cells, lymphocytes, megakaryocytes, neutrophil granulocytes, osteoclasts, or neutrophils.

13. The method of claim 1, wherein the stromal vascular fraction and cells derived therefrom are used in a cosmetic surgery application, to promote wound healing, are used in a tissue filler or in association with breast augmentation or reconstruction, tissue engineering, or burn treatment.

14. The method of claim 1, wherein after ultrasonication the stromal vascular fraction cells are poured into a specimen tube for filtering.

15. The method of claim 1, wherein the stromal vascular fraction cells are divided into 2 parts to which optionally are added equal amounts of 0.9% sodium chloride and these parts are centrifuged resulting in a layered sample with liquid on the bottom with a pellet and fat on top.

16. The method of claim 15, wherein centrifugation is effected for about 3 minutes at 500 RPM.

* * * * *